US010722593B2

(12) United States Patent
Vining et al.

(10) Patent No.: US 10,722,593 B2
(45) Date of Patent: Jul. 28, 2020

(54) ANTI-CANCER COMPOUNDS AND CONJUGATES THEREOF

(71) Applicant: SIRENAS LLC, San Diego, CA (US)

(72) Inventors: Oliver Booth Vining, San Diego, CA (US); Venkata Rami Reddy Macherla, San Diego, CA (US); Alexander Wayne Schammel, San Diego, CA (US); Ippei Usui, San Diego, CA (US); Jacob Neal Beverage, San Diego, CA (US); Elizabeth Paige Stout, San Diego, CA (US); Bryan Junn Lee, San Diego, CA (US); Steven Bruce Cohen, San Diego, CA (US); Eduardo Esquenazi, La Jolla, CA (US)

(73) Assignee: SIRENAS LLC, San Diego, CA (US)

( * ) Notice: Subject to any disclaimer, the term of this patent is extended or adjusted under 35 U.S.C. 154(b) by 0 days.

(21) Appl. No.: 15/765,232

(22) PCT Filed: Sep. 27, 2016

(86) PCT No.: PCT/US2016/053991
§ 371 (c)(1),
(2) Date: Mar. 30, 2018

(87) PCT Pub. No.: WO2017/058808
PCT Pub. Date: Apr. 6, 2017

(65) Prior Publication Data
US 2018/0296688 A1 Oct. 18, 2018

Related U.S. Application Data

(60) Provisional application No. 62/236,694, filed on Oct. 2, 2015.

(51) Int. Cl.
C07D 277/22 (2006.01)
A61K 47/68 (2017.01)
C07K 5/02 (2006.01)
A61P 35/00 (2006.01)
C07K 16/28 (2006.01)
C07K 16/30 (2006.01)

(52) U.S. Cl.
CPC .......... *A61K 47/6803* (2017.08); *A61P 35/00* (2018.01); *C07D 277/22* (2013.01); *C07K 5/0205* (2013.01); *C07K 16/2878* (2013.01); *C07K 16/30* (2013.01)

(58) Field of Classification Search
CPC .................................................. C07D 277/22
See application file for complete search history.

(56) References Cited

U.S. PATENT DOCUMENTS

| 5,635,483 A * | 6/1997 | Pettit | C07K 5/0205 514/19.3 |
| 5,767,237 A * | 6/1998 | Sakakibara | C07K 5/0205 514/19.3 |
| 7,659,241 B2 | 2/2010 | Senter et al. | |
| 2013/0129753 A1 * | 5/2013 | Doroski | C07K 7/02 424/179.1 |
| 2014/0127240 A1 | 5/2014 | Lerchen et al. | |
| 2017/0095525 A1 | 4/2017 | Papot et al. | |

FOREIGN PATENT DOCUMENTS

| CA | 2115355 C | 9/2007 |
| WO | WO 2000/002906 A1 | 1/2000 |
| WO | WO 2002/088172 A2 | 11/2002 |
| WO | WO 2005/081711 A2 | 9/2005 |
| WO | WO 2013/072813 A2 | 5/2013 |
| WO | WO 2013/173393 A1 * | 11/2013 |
| WO | WO 2015/118497 A1 | 8/2015 |
| WO | WO 2015/183978 A1 | 12/2015 |
| WO | WO 2016/064749 A2 | 4/2016 |
| WO | WO 2016/145099 A1 | 9/2016 |

OTHER PUBLICATIONS

International Search Report and Written Opinion dated Dec. 9, 2016 for International Application No. PCT/US2016/053991, filed Sep. 27, 2016.
Barker et al.; Fe(III)/NaBH4-Mediated Free Radical Hydrofluorination of Unactivated Alkenes; Journal of the American Chemical Society; (2012) pp. 13588-13591.
Crossley et al.; Simple, Chemoselective, Catalytic Olefin Isomerization; J. Am. Chem. Soc. 2014, 136, 16788-16791.
Dao et al.; Hydromethylation of Unactivated Olefins; J. Am. Chem. Soc. 2015, 137, 8046-8049.
Defieber et al.; Iridium-Catalyzed Synthesis of Primary Allylic Amines from Allylic Alcohols: Sulfamic Acid as Ammonia Equivalent; Angew. Chem. Int. Ed. 2007, 46, 3139-3143.
Gaspar et al.; Catalytic Hydrochlorination of Unactivated Olefins with para-Toluenesulfonyl Chloride; Angew. Chem. Int. Ed. 2008, 47, 5758-5760.
Gajula et al.; A Synthetic Dolastatin 10 Analogue Suppresses Microtubule Dynamics, Inhibits Cell Proliferation, and Induces Apoptotic Cell Death; J. Med. Chem. 2013, 56, 2235-2245.
Gui et al.; Practical olefin hydroamination with nitroarenes; sciencemag.org | Science; May 22, 2015, vol. 348, Issue 6237, pp. 886-891.
Leggans et al.; Iron(III)/NaBH4—Mediated Additions to Unactivated Alkenes: Synthesis of Novel 20'—Vinblastine Analogues; Organic Letters (2012) vol. 14, No. 6, pp. 1428-1431.

(Continued)

*Primary Examiner* — Rebecca L Anderson
(74) *Attorney, Agent, or Firm* — Knobbe, Martens, Olson & Bear, LLP

(57) ABSTRACT

Disclosed are compounds based on dolastatins, drug-conjugates, methods of preparing drug-conjugates, and uses thereof. Also disclosed are pharmaceutical compositions and methods of treatment. The compounds and drug-conjugates disclosed herein can be used to treat diseases such as bladder cancer, breast cancer, colon cancer, rectal cancer, endometrial cancer, kidney cancer, lung cancer, melanoma, non-Hodgkin lymphoma, glioblastoma, pancreatic cancer, prostate cancer, and thyroid cancer.

9 Claims, No Drawings

(56) References Cited

OTHER PUBLICATIONS

Lo et al.; Functionalized olefin cross-coupling to construct carbon-carbon bonds; Article, Dec. 2014, vol. 516, Nature, pp. 343-348.
Luesch et al.; Isolation of Dolastatin 10 from the Marine *Cyanobacterium symploca* Species VP642 and Total Stereochemistry and Biological Evaluation of Its Analogue Symplostatin 1; J. Nat. Prod. 2001, 64, 907-910.
Luesch et al.; Symplostatin 3, a New Dolastatin 10 Analogue from the Marine *Cyanobacterium symploca* sp. VP452; J. Nat. Prod. 2002, 65, 16-20.
Maderna et al.; Recent Advances in the Development of New Auristatins: Structural Modifications and Application in Antibody Drug Conjugates; Mol. Pharmaceutics 2015, 12, 1798-1812.
Miyazaki et al.; Synthesis and Antitumor Activity of Novel Dolastatin 10 Analogs; Chem. Pharm. Bull. vol. 43 (No. 10) 1706-1718 (1995).
Petasis et al.; A New and Practical Synthesis of α-Amino Acids from Alkenyl Boronic Acids; J. Am. Chem. Soc. 1997, 119, 445-446.
Pettit et al.; Antineoplastic agents 365. Dolastatin 10 SAR probes; Anti-Cancer Drug Design (1988), 13, 243-277.
Voica et al.; Guided desaturation of unactivated aliphatics; Nature Chemistry, vol. 4, Aug. 2012, pp. 629-635.
Waser et al.; Cobalt-Catalyzed Hydroazidation of Olefins: Convenient Access to Alkyl Azides; J. Am. Chem. Soc. 2005, 127, pp. 8294-8295.
Yonezawa et al.; Facile Synthesis of L-3,4-Didehydrovaline Constituting an Antibiotic, Phomopsin A; Short Paper; Synthesis 2000, No. 5, 634-636.

\* cited by examiner

ANTI-CANCER COMPOUNDS AND CONJUGATES THEREOF

CROSS REFERENCE TO RELATED APPLICATIONS

This application is a U.S. National Phase of International Application No. PCT/US2016/053991, filed on Sep. 27, 2016 and published on Apr. 6, 2017 as WO 2017/058808, which claims the benefit of U.S. Provisional Application 62/236,694, filed on Oct. 2, 2015.

BACKGROUND

Field

This application relates to the fields of chemistry and medicine, more particularly to anti-cancer compounds and drug-conjugates thereof, pharmaceutical compositions, and methods of treatment.

Description of the Related Technology

Recently, it has been found that an antibody (or antibody fragment such as a single-chain variable fragment) can be linked to a payload drug to form an immunoconjugate that has been termed antibody-drug conjugate, or ADC. The antibody causes the ADC to bind to the target cells. By combining the unique targeting capabilities of monoclonal antibodies with the cancer-killing ability of cytotoxic drugs, antibody-drug conjugates allow sensitive discrimination between healthy and diseased tissue. This means that, in contrast to traditional chemotherapeutic agents, antibody-drug conjugates target and attack the cancer cell so that healthy cells are less severely affected.

In developing antibody-drug conjugates, an anticancer compound is coupled to an antibody that specifically targets a specific marker (e.g. a protein that, ideally, is only to be found in or on tumor cells). The ADC may be absorbed or internalized in the target cell. After the ADC is internalized, the cytotoxic compound may be released to provider an anticancer effect.

Despite the known benefits of ADCs, the highly toxic nature of known payload drugs still results in toxicity issues. For example, some free drug is released systemically from the ADC and the ADC can accumulate in the liver. Thus, there is a need for improved ADCs in which the payloads remain relatively non-cytotoxic upon systemic free drug release, resulting in increased therapeutic windows.

Cytotoxic agents include drugs that are primarily used to treat cancer, frequently as part of a chemotherapy regime.

Cytotoxic agents have an effect of preventing the rapid growth and division of cancer cells. However, cytotoxic agents also affect the growth of other quick dividing cells in the body such as hair follicles and the lining of the digestive system. As a result of the treatment, many normal cells are damaged along with the cancer cells.

Dolastatin 10 is a cytotoxic marine ascidian alkaloid having anticancer activity, for example, in treating patients who have metastatic pancreatic cancer.

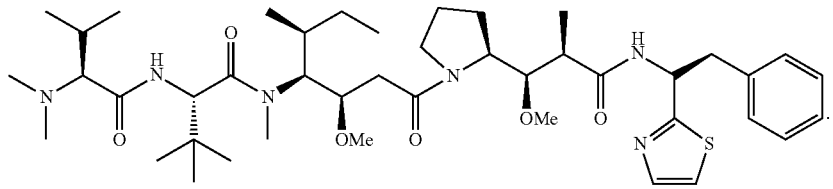

Dolastatin 10

SUMMARY

Some embodiments provide compound-conjugates, methods of preparing compound-conjugates, and uses thereof.

Some embodiments provide a compound having the structure of Formula I:

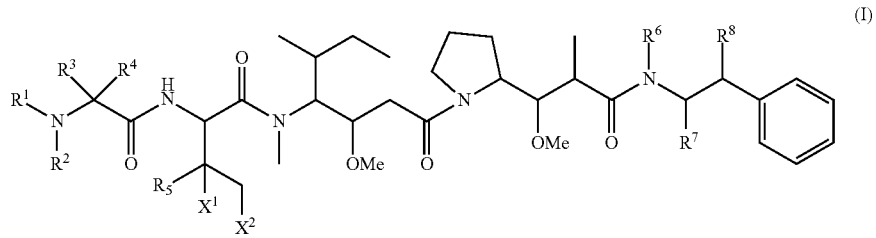

(I)

or pharmaceutically acceptable salts or solvents thereof, wherein:

$R^1$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^2$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^3$ is selected from the group consisting of hydrogen, deuterium, and optionally substituted $C_1$-$C_6$ alkyl, an optionally substituted hydroxyl, an optionally substituted $C_1$-$C_6$ alkoxy, an optionally substituted $C_3$-$C_7$ cycloalkyl, an optionally substituted aryl, and an optionally substituted heteroaryl;

$R^4$ is an optionally substituted $C_1$-$C_6$ alkyl;

$R^5$ is hydrogen, deuterium or an optionally substituted $C_1$-$C_6$ alkyl;

$R^6$ is hydrogen, deuterium or an optionally substituted $C_1$-$C_6$ alkyl;

$X^1$ and $X^2$ are each independently selected from the group consisting of hydrogen, deuterium, an optionally substituted $C_1$-$C_6$ alkyl, an optionally substituted aryl, an optionally substituted heteroaryl, halogen, —CN, —$N_3$, —COOR$^B$, —NR$^A$R$^B$, —OR$^B$, and —SR$^B$, where at least one of $X^1$ and $X^2$ is not hydrogen when $R^5$ is methyl;

$R^A$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^B$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^7$ is an optionally substituted $C_1$-$C_6$ alkyl, an optionally substituted heteroaryl, or —C(=O)R$^C$;

$R^C$ is selected from the group consisting of an optionally substituted $C_1$-$C_6$ alkyl, optionally substituted $C_1$-$C_6$ alkoxy, an optionally substituted $C_3$-$C_7$ cycloalkyl, an optionally substituted aryl, and an optionally substituted heteroaryl, and hydroxyl; and $R^8$ is hydrogen, deuterium or hydroxyl.

Some embodiments provide a compound having the structure of Formula II:

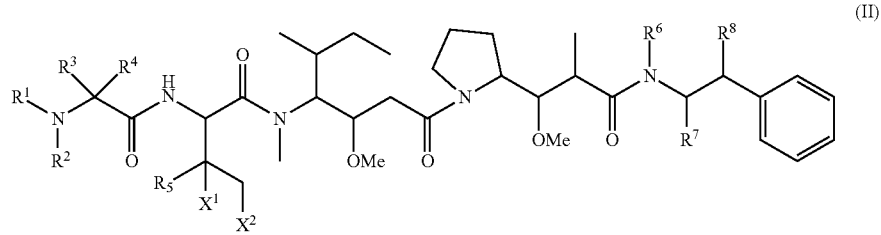

(II)

or pharmaceutically acceptable salts or solvates thereof, wherein:

$R^1$ is selected from the group consisting of an optionally substituted $C_1$-$C_6$ alkyl, an optionally substituted $C_3$-$C_7$ cycloalkyl, an optionally substituted aryl, and an optionally substituted heteroaryl;

$R^2$ is selected from the group consisting of $R^D$, an optionally substituted $C_1$-$C_6$ alkyl, an optionally substituted $C_3$-$C_7$ cycloalkyl, an optionally substituted aryl, and an optionally substituted heteroaryl;

$R^3$ is selected from the group consisting of hydrogen, deuterium, and optionally substituted $C_1$-$C_6$ alkyl, an optionally substituted hydroxyl, an optionally substituted $C_1$-$C_6$ alkoxy, an optionally substituted $C_3$-$C_7$ cycloalkyl, an optionally substituted aryl, and an optionally substituted heteroaryl;

$R^4$ is an optionally substituted $C_1$-$C_6$ alkyl;

$R^5$ is hydrogen, deuterium or an optionally substituted $C_1$-$C_6$ alkyl;

$R^6$ is hydrogen, deuterium or an optionally substituted $C_1$-$C_6$ alkyl;

$X^1$ and $X^2$ are each independently selected from the group consisting of hydrogen, deuterium, an optionally substituted $C_1$-$C_6$ alkyl, an optionally substituted aryl, an optionally substituted heteroaryl, halogen, —CN, —$N_3$, —COOR$^B$, —NR$^A$R$^B$, —OR$^B$, and —SR$^B$, where at least one of $X^1$ and $X^2$ is not hydrogen when $R^5$ is methyl;

$R^A$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^B$ is selected from the group consisting of hydrogen, $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-$L^1$-Val-Cit-PAB-C(O)— or Mal-$L^3$-$L^1$-Val-Cit-PAB-C(O)—;

$R^7$ is an optionally substituted $C_1$-$C_6$ alkyl, an optionally substituted heteroaryl, or —C(=O)R$^C$;

$R^C$ is selected from the group consisting of an optionally substituted $C_1$-$C_6$ alkyl, optionally substituted $C_1$-$C_6$ alkoxy, an optionally substituted $C_3$-$C_7$ cycloalkyl, an optionally substituted aryl, and an optionally substituted heteroaryl, and hydroxyl; and $R^8$ is hydrogen, deuterium, —OR$^D$, or —SR$^D$;

$R^D$ is selected from the group consisting of hydrogen, $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-$L^1$-Val-Cit-PAB-C(O)— and Mal-$L^3$-L-Val-Cit-PAB-C(O)—;

$R^{3A}$ is

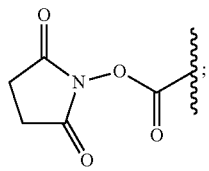 [SMILES: *C(=O)ON1C(=O)CCC1=O]

$R^{4A}$ is a conjugation moiety;

$R^{1A}$ is a conjugated targeting moiety;

$L^1$ is a linker or a bond; and $L^3$ is an alkanoyl.

Some embodiments provide a method of treating a disease selected from the group consisting of uterine sarcoma cancer, bladder cancer, breast cancer, colon cancer, rectal cancer, endometrial cancer, kidney cancer, lung cancer, melanoma, non-Hodgkin lymphoma, leukemia, pancreatic cancer, prostate cancer, and thyroid cancer, comprising administering a compound as disclosed and described herein to a subject in need thereof.

Some embodiments provide a method delivering a compound having the structure of Formula I to an in vivo mammalian cell, the method comprising administering a compound having the structure of Formula II to a mammal comprising the in vivo mammalian cell.

Some embodiments provide use of a compound having the structure of Formula II to provide a compound having the structure of Formula I to a target location.

Also provided herein are the compounds described above conjugated to a targeting moiety with a linker. Also provided herein are the compounds described above with a linker.

DETAILED DESCRIPTION

Some embodiments provide a compound having the structure of Formula I and/or II.

Some embodiments provide a composition including compound having the structure of Formula I and/or II; and a carrier.

Definitions

As used herein, common organic abbreviations are defined as follows:
Ac Acetyl
aq. Aqueous
BOC or Boc tert-Butoxycarbonyl
BrOP bromo tris(dimethylamino) phosphonium hexafluorophosphate
Bu n-Butyl
° C. Temperature in degrees Centigrade
DCM methylene chloride
DEPC Diethylcyanophosphonate
DIC diisopropylcarbodiimide
DIEA Diisopropylethylamine
DMF N,N'-Dimethylformamide
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOAt 1-Hydroxy-7-azabenzotriazole
HOBT N-Hydroxybenzotriazole
HOSu N-Hydroxysuccinimide
HPLC High-performance liquid chromatography
LC/MS Liquid chromatography-mass spectrometry
Mal Maleimido
Mc Maleimidocaproyl
Me Methyl
MeOH Methanol
MeCN Acetonitrile
mL Milliliter(s)
MS mass spectrometry
RP-HPLC reverse phase HPLC
rt room temperature
t-Bu tert-Butyl
TBDPS tert-Butyldiphenylsilyl
TEA Triethylamine
Tert, t tertiary
TFA Trifluoroacetic acid
THF Tetrahydrofuran
THP Tetrahydropyranyl
TLC Thin-layer chromatography
μL Microliter(s)

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$.

As used herein, "PAB" refers to a para-aminobenzyloxy moiety. The PAB moiety is typically depicted as a di-radical (i.e., has two points of attachment to the rest of the molecule), it is to be understood that the PAB amino group provides an amide bond with the adjacent amino acid residue (e.g. citrulline) and the PAB oxygen group provides a carbonate with the adjacent oxycarbonyl or carbamate group with the adjacent aminocarbonyl of the depicted structure. Thus, for example, a substituent depicted as -Cit-PAB-C(O)-Phe- has the following structure:

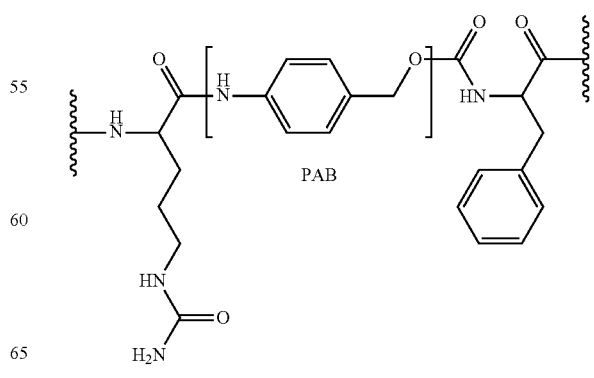

where the PAB moiety is shown within the brackets.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O (oxygen), N (nitrogen) or S (sulfur), and in preferred five membered monocyclic heterocyclyls, the heteroatom(s) are selected from one or two heteroatoms selected from O (oxygen), N (nitrogen) or S (sulfur). Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

As used herein, "alkanoyl" refers to a "carbonyl" substituted with an "alkyl" group, the "alkanoyl" group is covalently bonded to the parent molecule through the carbon of the "carbonyl" group. Non-limiting examples include methanoyl, ethanoyl, and propanoyl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—$OC(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)C(=O)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—$OC(=S)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "urea" group refers to a "—$N(R_A)C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—$N(R_A)C(=S)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—$C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N($R_A$)C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

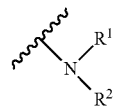

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

where ring E is a heteroaryl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

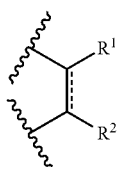

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

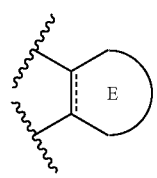

where E is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

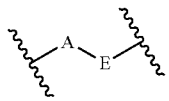

includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "antibody-drug conjugate" refers to molecular entity that includes an antibody linked to a drug moiety, optionally via a chemical linker.

Compounds

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element present in a compound either specifically or generically described herein may include any isotope of said element. For example, in a compound specifically or generically described herein a hydrogen atom may be explicitly disclosed or understood to be present in the compound and each such hydrogen atom is any isotope of hydrogen, including but not limited to hydrogen-1 (protium) and hydrogen-2 (deuterium). Thus, reference herein to a compound encompasses all potential isotopic forms unless the context clearly dictates otherwise.

Utilities and Applications

Some embodiments provide a method of treating a patient in need thereof comprising administering a compound as disclosed and described herein to said patient. In some embodiments, the patient may have cancer. In some embodiments, the compound may have anti-tumor activity.

Structures

Some embodiments provide a compound having the structure of Formula I:

or pharmaceutically acceptable salts or solvents thereof, wherein:

$R^1$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^2$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^3$ is selected from the group consisting of hydrogen, deuterium, and optionally substituted $C_1$-$C_6$ alkyl, an optionally substituted hydroxyl, an optionally substituted $C_1$-$C_6$ alkoxy, an optionally substituted $C_3$-$C_7$ cycloalkyl, an optionally substituted aryl, and an optionally substituted heteroaryl;

$R^4$ is an optionally substituted $C_1$-$C_6$ alkyl;

$R^5$ is hydrogen, deuterium or an optionally substituted $C_1$-$C_6$ alkyl;

$R^6$ is hydrogen, deuterium or an optionally substituted $C_1$-$C_6$ alkyl;

$X^1$ and $X^2$ are each independently selected from the group consisting of hydrogen, deuterium, an optionally substituted $C_1$-$C_6$ alkyl, an optionally substituted aryl, an optionally substituted heteroaryl, halogen, —CN, —N$_3$, —COOR$^B$, —NR$^A$R$^B$, —OR$^B$, and —SR$^B$, where at least one of $X^1$ and $X^2$ is selected from the group consisting of an optionally substituted aryl, an optionally substituted heteroaryl, halogen, —CN, —N$_3$, —COOR$^B$, —NR$^A$R$^B$, —OR$^B$, and —SR$^B$ when $R^5$ is methyl;

$R^A$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^B$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^7$ is an optionally substituted $C_1$-$C_6$ alkyl, an optionally substituted heteroaryl, or —C(=O)R$^C$;

$R^C$ is selected from the group consisting of an optionally substituted $C_1$-$C_6$ alkyl, optionally substituted $C_1$-$C_6$ alkoxy, an optionally substituted $C_3$-$C_7$ cycloalkyl, an optionally substituted aryl, and an optionally substituted heteroaryl, and hydroxyl; and $R^8$ is hydrogen, deuterium or hydroxyl In some embodiments, the compound having the structure of Formula I has the structure Formula Ia:

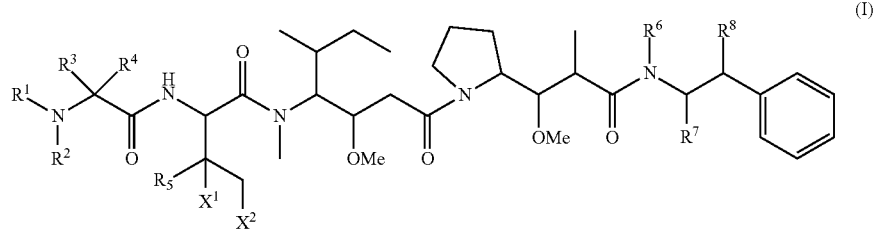

(I)

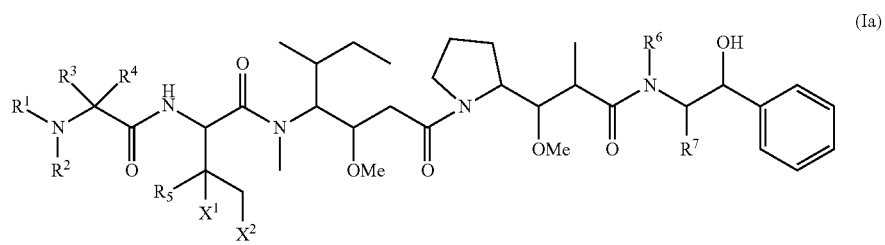

(Ia)

or pharmaceutically acceptable salts or solvates thereof.

In some embodiments, the compound having the structure of Formula I has the structure Formula Ib:

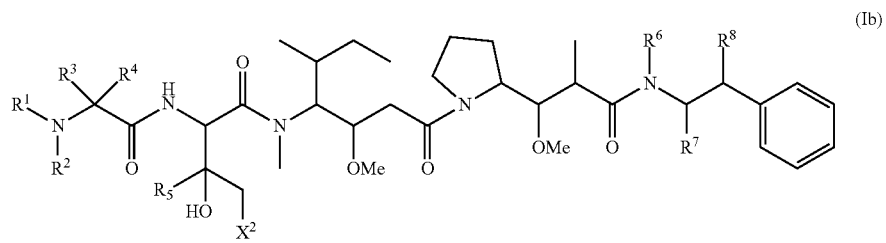

(Ib)

or pharmaceutically acceptable salts or solvates thereof.

In some embodiments, the compound having the structure of Formula I has the structure Formula Ic:

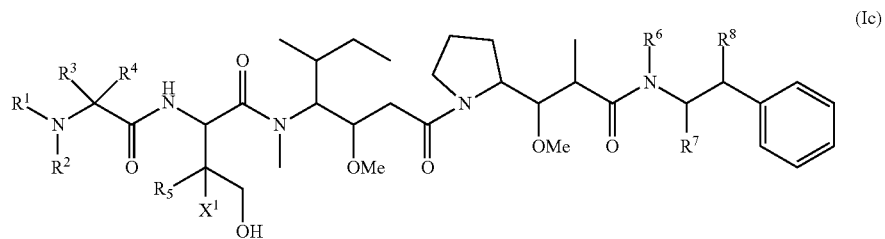

(Ic)

or pharmaceutically acceptable salts or solvates thereof.

Some embodiments provide a compound having the structure of Formula II:

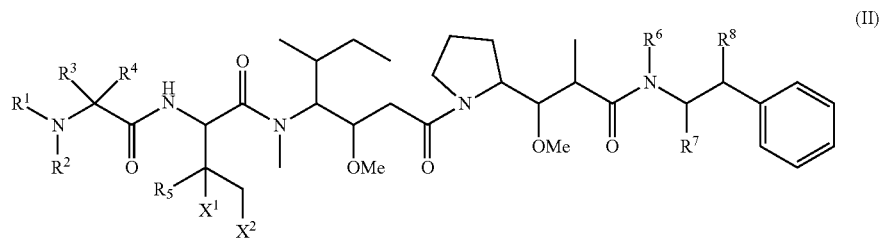

(II)

or pharmaceutically acceptable salts or solvates thereof, wherein:

$R^1$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^2$ is selected from the group consisting of $R^D$, an optionally substituted $C_1$-$C_6$ alkyl, an optionally substituted $C_3$-$C_7$ cycloalkyl, an optionally substituted aryl, and an optionally substituted heteroaryl;

$R^3$ is selected from the group consisting of hydrogen, deuterium, and optionally substituted $C_1$-$C_6$ alkyl, an optionally substituted hydroxyl, an optionally substituted $C_1$-$C_6$ alkoxy, an optionally substituted $C_3$-$C_7$ cycloalkyl, an optionally substituted aryl, and an optionally substituted heteroaryl;

$R^4$ is an optionally substituted $C_1$-$C_6$ alkyl;

$R^5$ is hydrogen, deuterium or an optionally substituted $C_1$-$C_6$ alkyl;

$R^6$ is hydrogen, deuterium or an optionally substituted $C_1$-$C_6$ alkyl;

$X^1$ and $X^2$ are each independently selected from the group consisting of hydrogen, deuterium, an optionally substituted $C_1$-$C_6$ alkyl, an optionally substituted aryl, an optionally substituted heteroaryl, halogen, —CN, —$N_3$, —COOR$^B$, —NR$^4$R$^B$, —OR$^B$, and —SR$^B$, where at least one of $X^1$ and $X^2$ is selected from the group consisting of an optionally substituted aryl, an optionally substituted heteroaryl, halogen, —CN, —$N_3$, —COOR$^B$, —NR$^4$R$^B$, —OR$^B$, and —SR$^B$ when $R^5$ is methyl;

$R^A$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^B$ is selected from the group consisting of hydrogen, $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-$L^1$-Val-Cit-PAB-C(O)— or Mal-$L^3$-$L^1$-Val-Cit-PAB-C(O)—;

$R^7$ is an optionally substituted $C_1$-$C_6$ alkyl, an optionally substituted heteroaryl, or —C(=O)R$^C$;

$R^C$ is selected from the group consisting of an optionally substituted $C_1$-$C_6$ alkyl, optionally substituted $C_1$-$C_6$ alkoxy, an optionally substituted $C_3$-$C_7$ cycloalkyl, an optionally substituted aryl, and an optionally substituted heteroaryl, and hydroxyl; and $R^8$ is hydrogen, deuterium, —OR$^D$, or —SR$^D$;

$R^D$ is selected from the group consisting of hydrogen, $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-L-Val-Cit-PAB-C(O)— and Mal-$L^3$-L-Val-Cit-PAB-C(O)—;

$R^{3A}$ is

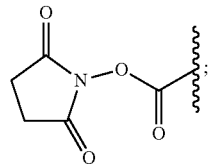 [SMILES: *C(=O)ON1C(=O)CCC1=O]

$R^{4A}$ is a conjugation moiety;
$R^{1A}$ is a conjugated targeting moiety;
$L^1$ is a linker or a bond; and
$L^3$ is an alkanoyl.

In some embodiments, the compound having the structure of Formula II has the structure Formula IIa:

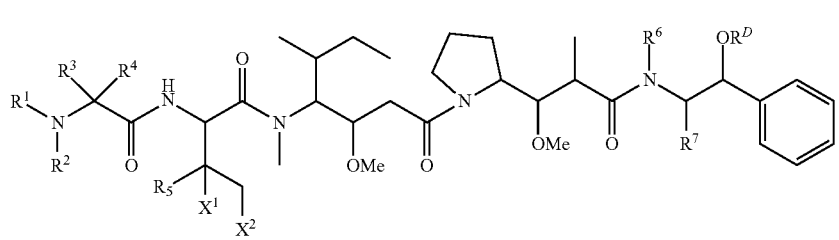

(IIa)

or pharmaceutically acceptable salts or solvates thereof, wherein $R^D$ is selected from the group consisting of $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-L-Val-Cit-PAB-C(O)— and Mal-$L^3$-L-Val-Cit-PAB-C(O)—.

In some embodiments, the compound having the structure of Formula II has the structure Formula IIb:

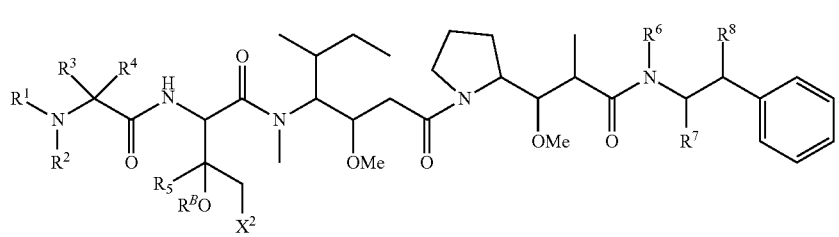

(IIb)

or pharmaceutically acceptable salts or solvates thereof, wherein $R^B$ is selected from the group consisting of $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-L-Val-Cit-PAB-C(O)— and Mal-$L^3$-L-Val-Cit-PAB-C(O)—.

In some embodiments, the compound having the structure of Formula II has the structure Formula IIc:

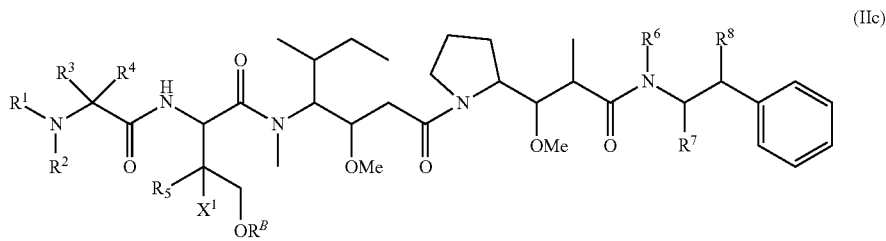

(IIc)

or pharmaceutically acceptable salts or solvates thereof, wherein $R^B$ is selected from the group consisting of $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-L-Val-Cit-PAB-C(O)— and Mal-$L^3$-$L^1$-Val-Cit-PAB-C(O)—.

In some embodiments, the compound having the structure of Formula II has the structure Formula IId:

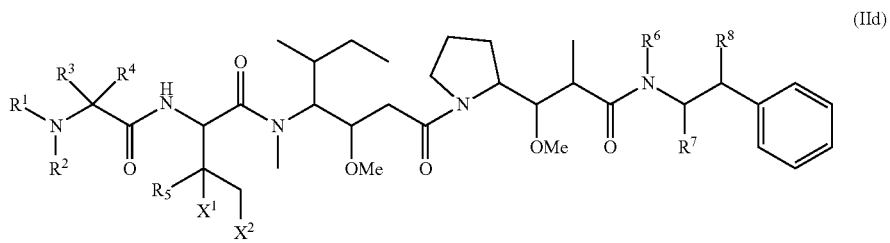

(IId)

or pharmaceutically acceptable salts or solvates thereof, wherein $R^D$ is selected from the group consisting of $R^{1A}$-$L^1$-, $R^{3A}$-$L^1$-, $R^{4A}$-$L^1$-, Mc-$L^1$-, Mal-$L^3$-$L^1$-, $R^{1A}$-Mal-$L^3$-$L^1$-Val-Cit-PAB-C(O)— and Mal-$L^3$-$L^1$-Val-Cit-PAB-C(O)—.

In some embodiments of a compound having the structure of Formula II, IIa and IId, $R^D$ is $R^{1A}$-Mc-Val-Cit-PAB-C(O)— or $R^{1A}$-Mal-$L^3$-Val-Cit-PAB-C(O)—. In some embodiments of a compound having the structure of Formula II, IIb and IIc, $R^B$ is $R^{1A}$-Mc-Val-Cit-PAB-C(O)— or $R^{1A}$-Mal-$L^3$-Val-Cit-PAB-C(O)—. In some embodiments of a compound having the structure of Formula II, IIa and IId, $R^D$ is Mc-Val-Cit-PAB-C(O)— or Mal-$L^3$-Val-Cit-PAB-C(O)—. In some embodiments of a compound having the structure of Formula II, IIb and IIc, $R^B$ is Mc-Val-Cit-PAB-C(O)— or Mal-$L^3$-Val-Cit-PAB-C(O)—.

In some embodiments of a compound having the structure of Formula II, IIa and IId, $R^D$ may be

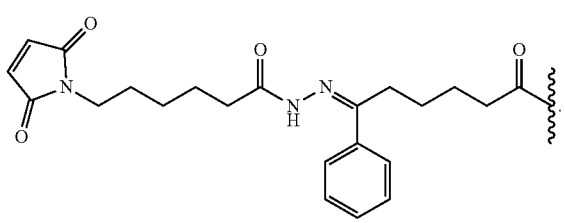 [SMILES: *C(=O)CCCC/C(=N/NC(=O)CCCCCN1C(=O)C=CC1=O)c1ccccc1]

In some embodiments of a compound having the structure of Formula II, IIb and IIc, $R^B$ may be In some embodiments of a compound having the structure of Formula II, IIa and IId, $R^D$ may be

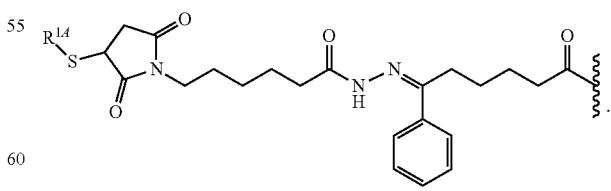

In some embodiments of a compound having the structure of Formula II, IIb and IIc, $R^B$ may be

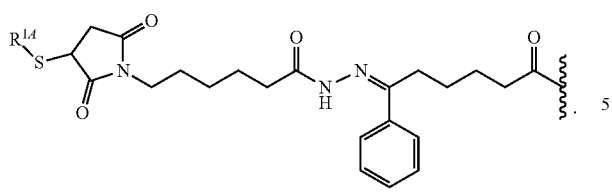

In some embodiments, the targeting moiety binds to one or more tumor-associated antigens or cell surface receptors selected from the group consisting of CD19, CD22, CD30, CD33, CD56, CD70, CD79b, CD74, CD138, HER2, GPNMB, PSMA, SLC44A4, CA6, CA-IX, Mesothelin, CD66e, CEACAM5, and Nectin-4.

In some embodiments, the $R^{14}$ comprises a targeting moiety selected from the group consisting of brentuximab, inotuzumab, gemtuzumab, milatuzumab, trastuzumab, glembatumomab, lorvotuzumab, or labestuzumab, or derivatives thereof.

In some embodiments, the targeting moiety is a monoclonal antibody (mAB). In some embodiments, the targeting moiety is an antibody fragment, surrogate, or variant. In some embodiments, the targeting moiety is a protein ligand. In some embodiments, the targeting moiety is a protein scaffold. In some embodiments, the targeting moiety is a peptide, cysteine-engineered antibody or antibody-like protein. In some embodiments, the targeting moiety is a small molecule ligand or nucleic acid aptamer.

In some embodiments, $L^1$ may be $-(CHR^{13})-CH_2-(CR^{14}R^{15})-S-S-(CR^{16}R^{17})-((CH_2)_n(CO)_r-$; n is 1, 2, 3, 4, or 5; r is 0 or 1; $R^{13}$ is hydrogen or $SO_3H$; and $R^{14}$, $R^{15}$, $R^{16}$ and $R^{17}$ are each independently hydrogen or an optionally substituted $C_1$-$C_6$ alkyl. In some embodiments, $L^1$ comprises

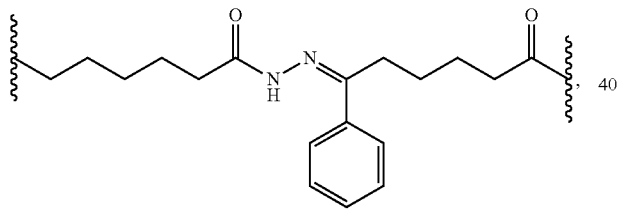

In some embodiments, $L^1$ comprises a dipeptide selected from the group consisting of -Phe-Lys-, -Val-Ala-, -Val-Lys-; -Ala-Lys-, -Val-Cit-, -Phe-Cit-, -Leu-Cit-, -Ile-Cit-, -Phe-Arg-, and -Trp-Cit-. In some embodiments, $R^{14}$-$L^1$- is

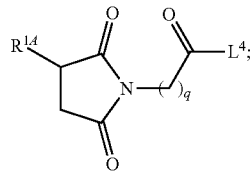

q is 0 to 6; and $L^4$ is a linker. In some embodiments, $R^{14}$-$L^1$- is

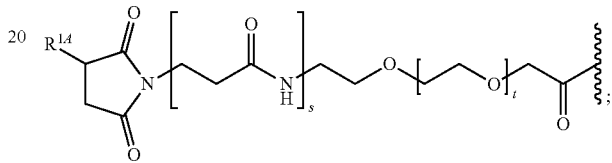

s is 0 or 1; and t is 0 to 30. In some embodiments, $L^1$- comprises

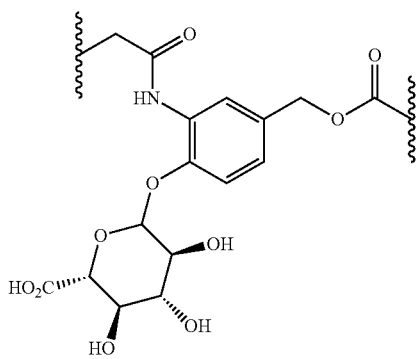 [SMILES: *CC(=O)Nc1cc(COC(*)=O)ccc1OC1O[C@@H](C(=O)O)[C@H](O)[C@@H](O)[C@@H]1O]

In some embodiments, $R^{14}$-$L^1$- is

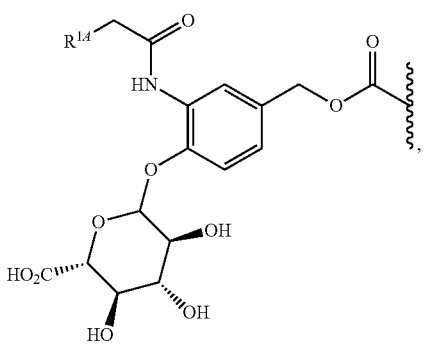

-continued
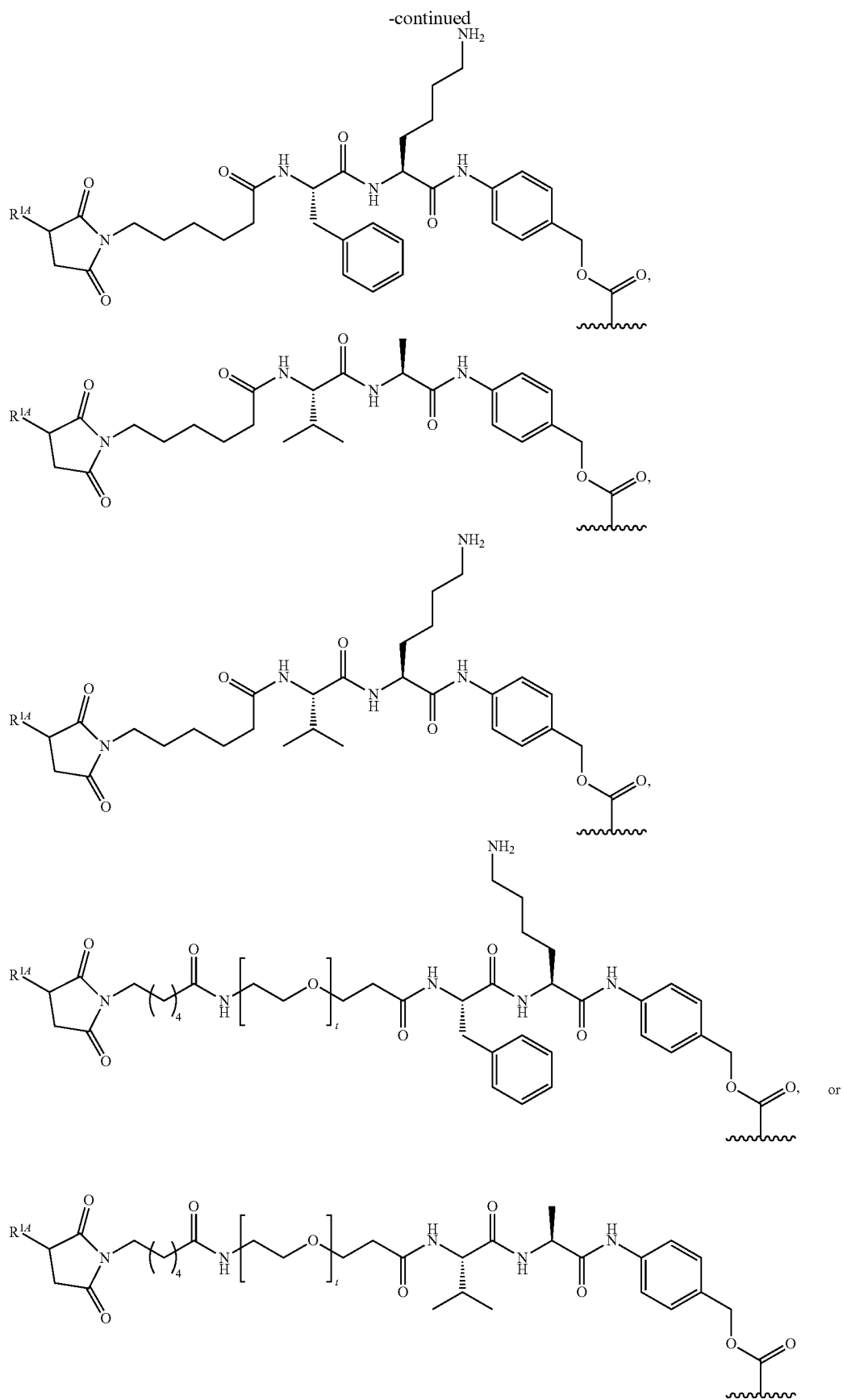

where t is 0 to 30. In some embodiments, $R^{4A}$— is

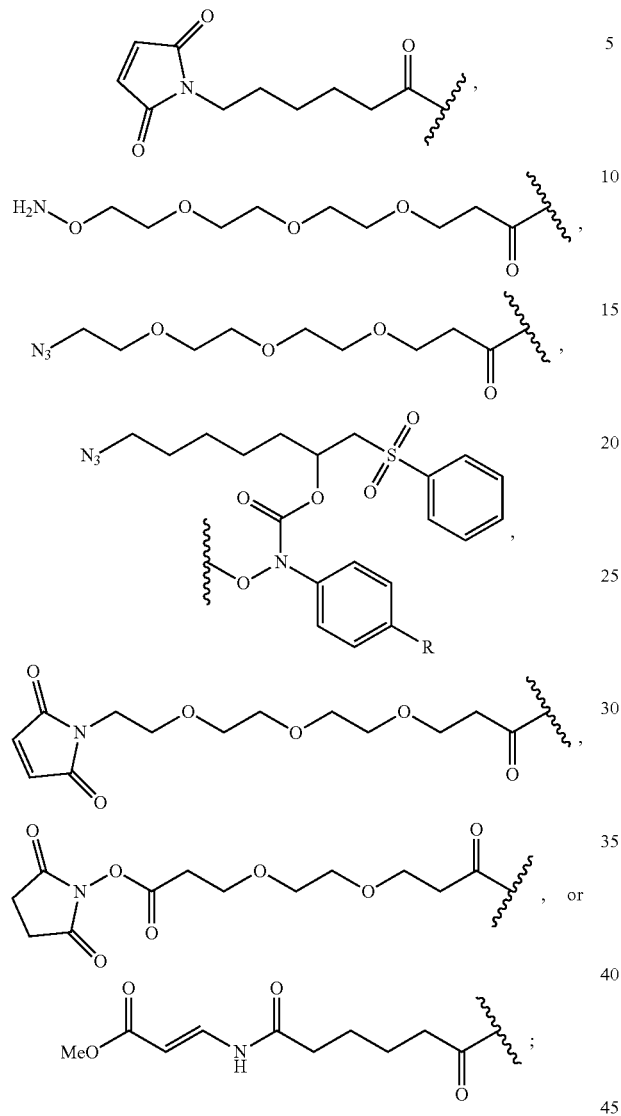

and

R is hydrogen, —C(=O)N(CH$_2$CH$_3$)$_2$, or —SO$_2$N(CH$_2$CH$_2$)$_2$O.

In some embodiments, $R^{4A}$— is

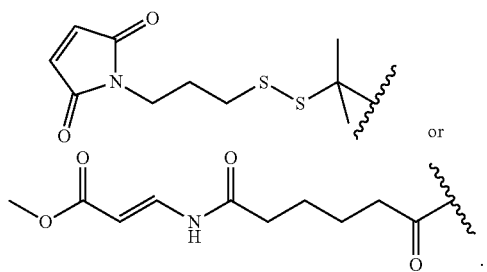

In some embodiments, $L^1$ is $L^{1A}$-$L^{2A}$; $L^{1A}$ comprises at least one moiety selected from the group consisting of

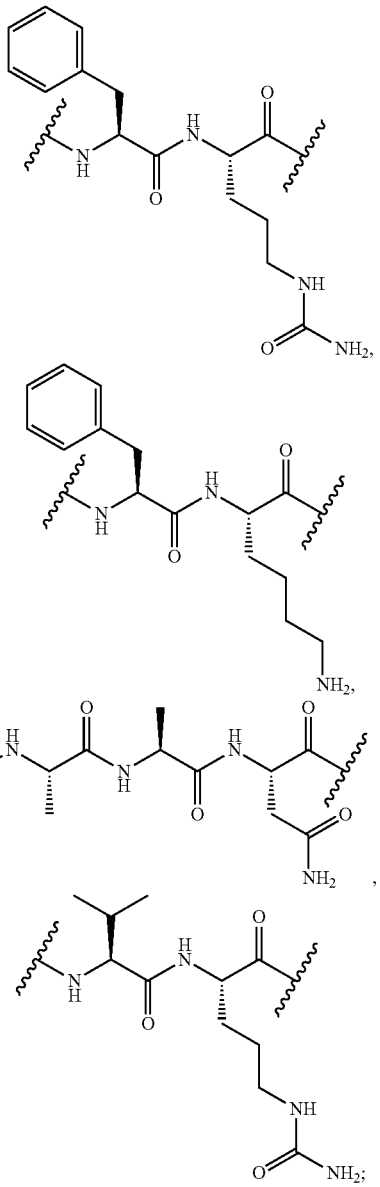

$L^{2A}$ comprises at least one moiety selected from the group consisting of

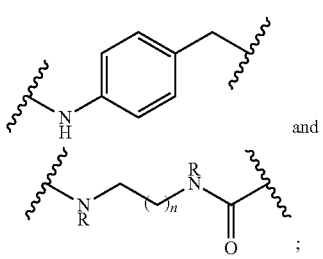

n is 0 or 1; and R is hydrogen or alkyl.

In some embodiments of a compound having the structure of Formula II, $R^1$ is $R^D$.

In some embodiments, the compound having the structure of Formula I is not

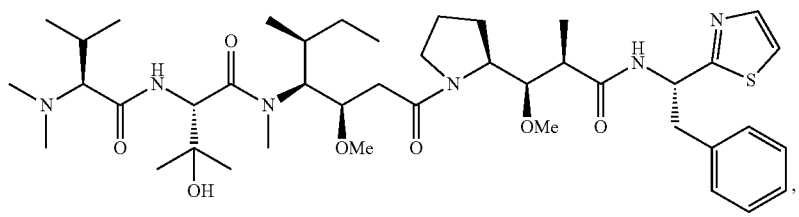 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C)C(C)(C)O]

or a pharmaceutically acceptable salt thereof.

In some embodiments, the compound having the structure of Formula I is

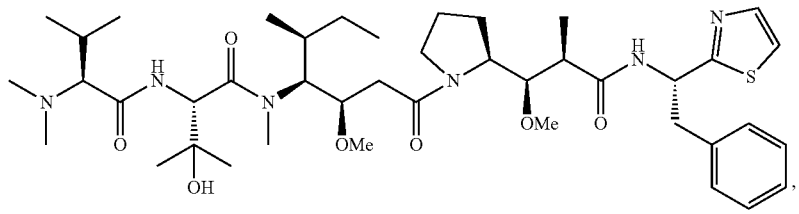 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C)C(C)(C)O]

or a pharmaceutically acceptable salt thereof.

Also provided herein are the compounds described above conjugated to a targeting moiety with a linker. Also provided herein are the compounds described above with a linker.

In some embodiments, the compound is conjugated to a targeting moiety.

In some embodiments, the targeting moieties can be an antibody, antibody fragment, antibody-like protein or nucleic acid aptamer.

In some embodiments, the targeting moiety includes a monoclonal antibody (mAB). In some embodiments, the compound includes a spacer or a linker.

Conjugation Methods, Spacers and Linkers Involved

Some embodiments provide a method of conjugating of a targeting moiety through a linker.

In some embodiments, the method includes a single-step or sequential conjugation approach. In some embodiments, the compound includes a linker. In some embodiments, the linker may include a noncleavable or cleavable unit such as peptides.

In some embodiments of a compound represented by Formula II, $R^{14}$-$L^1$- has a structure selected from:

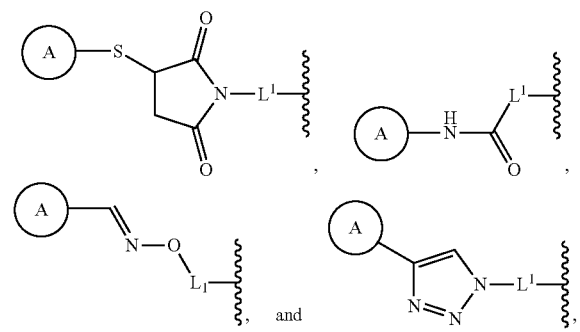

wherein A is the targeting moiety. In some embodiments, $L^1$ may be —(CH$_2$O)$_n$ (where n is 1, 2, 3, 4, 5, 6, or 7), optionally substituted $C_1$-$C_8$ alkyl, optionally substituted $C_3$-$C_5$ cycloalkyl, optionally substituted $C_1$-$C_8$ alkoxy, optionally substituted aryl, optionally substituted heteroaryl, optionally substituted heterocyclyl, or combination thereof.

In some embodiments, $L^1$ is an optionally substituted $C_1$-$C_8$ alkyl. In some embodiments, $L^5$ is $C_1$-$C_8$ alkyl.

In some embodiments of a compound represented by Formula II, $R^{14}$-$L^1$- has a structure selected from:

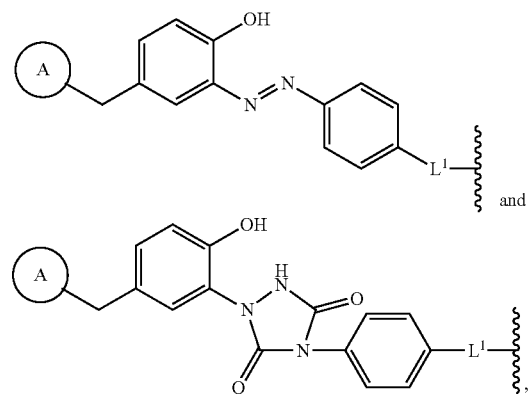

wherein A is the targeting moiety. In some embodiments, $L^1$ may be —(CH$_2$O) (where n is 1, 2, 3, 4, 5, 6, or 7), optionally substituted $C_1$-$C_8$ alkyl, optionally substituted $C_3$-$C_8$ cycloalkyl, optionally substituted $C_1$-$C_8$ alkoxy, optionally substituted aryl, optionally substituted heteroaryl, optionally substituted heterocyclyl, or combination thereof.

In some embodiments, $L^1$ is an optionally substituted $C_1$-$C_8$ alkyl. In some embodiments, $L^5$ is $C_1$-$C_8$ alkyl.

In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide, cysteine-engineered antibody or antibody-like protein. In some embodiments, the targeting moiety may be RNA or DNA. In some embodiments, the targeting moiety may be a RNA or DNA fragment.

In some embodiments, $L^1$ may be a peptide. In some embodiments, $L^1$ may include —$(CH_2)_n$— where n is 1, 2, 3, 4, 5, 6, 7, 8, 9, or 10. In some embodiments, $L^1$ may include —$(CH_2CH_2O)_n$— where n is 1, 2, 3, 4, 5, 6, 7, 8, 9, or 10. In some embodiments, $L^1$ may include Val-Ala-, Phe-Lys-, D-Val-Leu-Lay, Gly-Gly-Arg, Ala-Ala-Asn-, or the like. In some embodiments, $L^1$ may include any combination of peptide, oligosaccharide, —$(CH_2)_n$—, —$(CH_2CH_2O)_n$—, Val-Ala-, Phe-Lys-, D-Val-Leu-Lay, Gly-Gly-Arg, Ala-Ala-Asn-, and the like. In some embodiments, the $L^1$ may include a peptide. In some embodiments, $L^1$ may be —$(CHR^{13})$—$CH_2$—$(CR^{14}R^{15})$—S—S—$(CR^{16}R^{17})$—$(CH_2)_n(CO)_r$—; n may be 1, 2, 3, 4, or 5; r may be 0 or 1; $R^{13}$ may be hydrogen or $SO_3H$; and $R^{14}$, $R^{15}$, $R^{16}$ and $R^{17}$ may each be independently hydrogen or an optionally substituted $C_1$-$C_6$ alkyl.

In some embodiments, $L^1$ may comprise

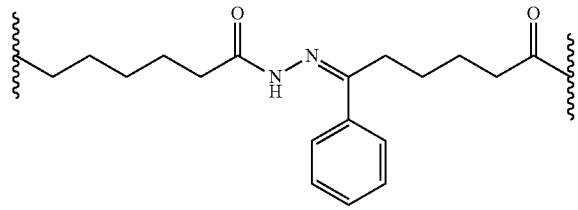

In some embodiments, the compound-conjugates may include one or more components selected from the group consisting of an amino acid, an amino acid residue, an amino acid analog, and a modified amino acid. In some embodiments of a compound represented by Formula II, L comprises a dipeptide selected from the group consisting of -Phe-Lys-, -Val-Ala-, -Val-Lys-; -Ala-Lys-, -Val-Cit-, -Phe-Cit-, -Leu-Cit-, -Ile-Cit-, -Phe-Arg-, and -Trp-Cit-.

In some embodiments of a compound represented by Formula II, $L^1$ comprises at least one selected from the group consisting of: an optionally substituted alkyl, optionally substituted alkenyl, optionally substituted alkynyl, an optionally substituted alkoxy, an optionally substituted cycloalkyl, an optionally substituted aryl, optionally substituted heterocycly, and an optionally substituted heteroaryl.

In some embodiments of a compound represented by Formula II, $L^1$ comprises at least one selected from the group consisting of: a disulfide, an ester, a carbamate, a ketal, a urea and a urethane.

In some embodiments of a compound represented by Formula II, $R^{14}$-$L^1$- is

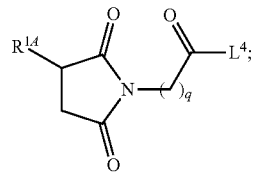

q is 0 to 6; and $L^4$ is a linker.

In some embodiments of a compound represented by Formula II, $R^{14}$-$L^1$- is

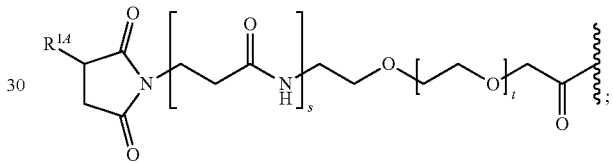

s is 0 or 1; and t is 0 to 30.

In some embodiments of a compound represented by Formula II, $R^{14}$-$L^1$- is

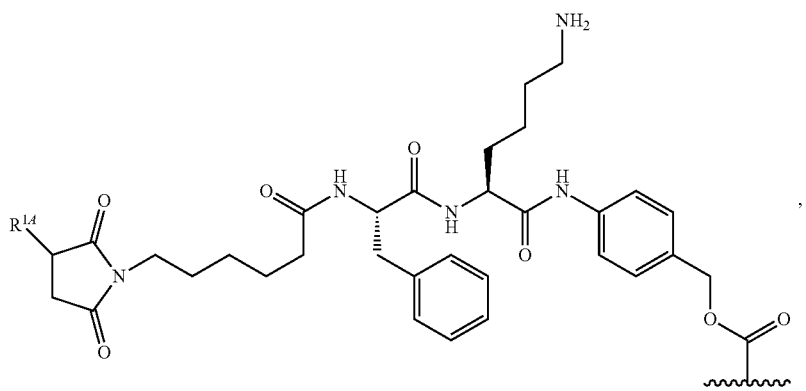

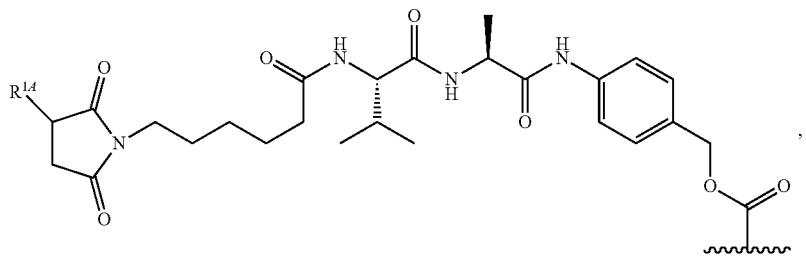

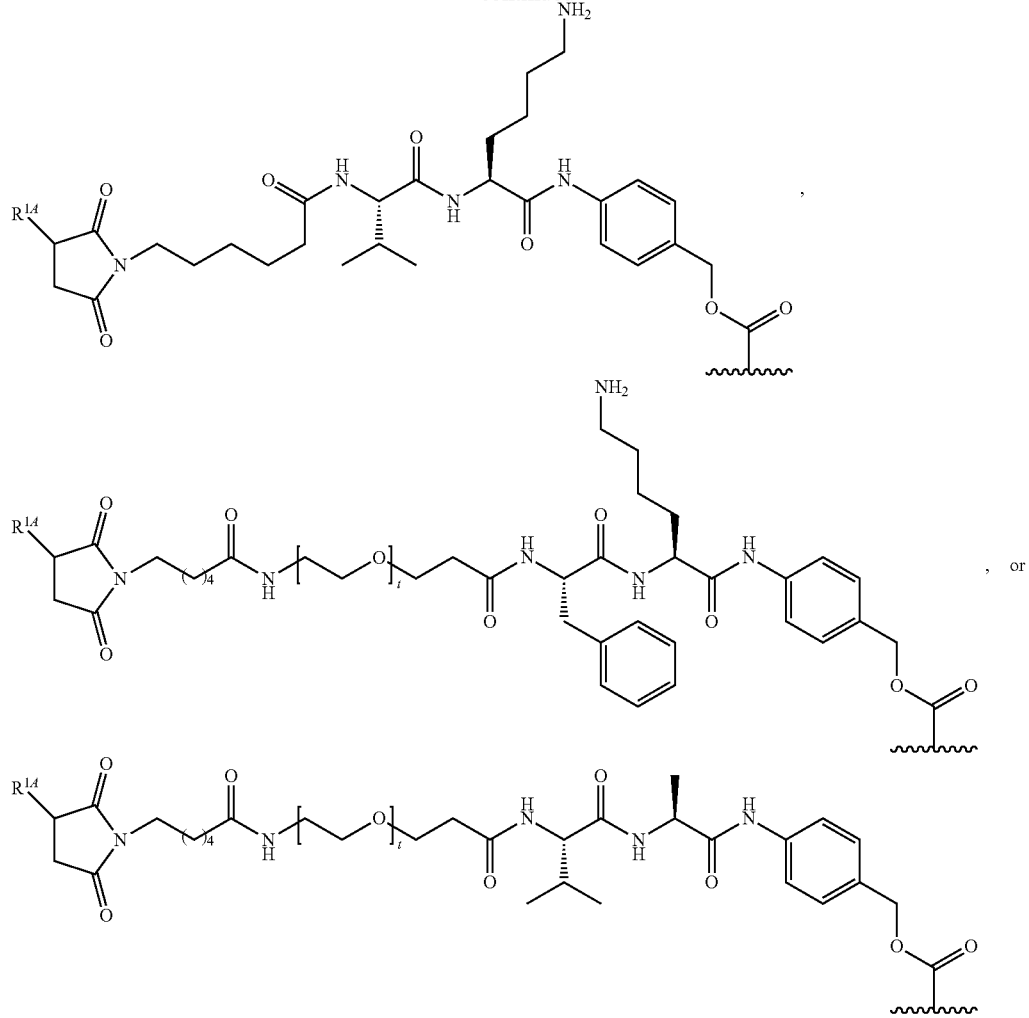

where t is 0 to 30. In some embodiments, $R^{14}$ may be an antibody fragment, surrogate, or variant. In some embodiments, $R^{14}$ may be a monoclonal antibody (mAB). In some embodiments, $R^{14}$ may be a targeting moiety selected from the group consisting of brentuximab, inotuzumab, gemtuzumab, milatuzumab, trastuzumab, glembatumomab, lorvotuzumab, or labestuzumab, or derivatives thereof.

As used herein, the term "peptide" refers to a structure including one or more components each individually selected from the group consisting of an amino acid, an amino acid residue, an amino acid analog, and a modified amino acid. The components are typically joined to each other through an amide bond.

As used herein, the term "amino acid" includes naturally occurring amino acids, a molecule having a nitrogen available for forming an amide bond and a carboxylic acid, a molecule of the general formula $NH_2$—CHR—COOH or the residue within a peptide bearing the parent amino acid, where "R" is one of a number of different side chains. "R" can be a substituent found in naturally occurring amino acids. "R" can also be a substituent referring to one that is not of the naturally occurring amino acids.

As used herein, the term "amino acid residue" refers to the portion of the amino acid which remains after losing a water molecule when it is joined to another amino acid.

As used herein, the term "amino acid analog" refers to a structural derivative of an amino acid parent compound that often differs from it by a single element.

As used herein, the term "modified amino acid" refers to an amino acid bearing an "R" substituent that does not correspond to one of the twenty genetically coded amino acids.

As used herein, the abbreviations for the genetically encoded L-enantiomeric amino acids are conventional and are as follows: The D-amino acids are designated by lower case, e.g. D-proline=p, etc.

TABLE 1

| Amino Acids | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |

TABLE 1-continued

| Amino Acids | One-Letter Symbol | Common Abbreviation |
|---|---|---|
| Lysine | K | Lys |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Certain amino acid residues in the compound-conjugate can be replaced with other amino acid residues without significantly deleteriously affecting, and in many cases even enhancing, the activity of the peptides. Thus, also contemplated by the preferred embodiments are altered or mutated forms of the active agent-conjugate wherein at least one defined amino acid residue in the structure is substituted with another amino acid residue or derivative and/or analog thereof. It will be recognized that in preferred embodiments, the amino acid substitutions are conservative, i.e., the replacing amino acid residue has physical and chemical properties that are similar to the amino acid residue being replaced.

For purposes of determining conservative amino acid substitutions, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into nonpolar and aromatic amino acids. The definitions of the various categories of amino acids are as follows:

The term "hydrophilic amino acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gln (Q), Asp (D), Lys (K) and Arg (R).

The term "hydrophobic amino acid" refers to an amino acid exhibiting a hydrophobicity of greater than zero according to the normalized consensus hydrophobicity scale of Eisenberg, 1984, J. Mol. Biol. 179:1.25-142. Genetically encoded hydrophobic amino acids include Pro (P), Ile (I), Phe (F), Val (V), Leu (L), Trp (W), Met (M), Ala (A), Gly (G) and Tyr (Y).

The term "acidic amino acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

The term "basic amino acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

The term "polar amino acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

The term "nonpolar amino acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Leu (L), Val (V), Ile (I), Met (M), Gly (G) and Ala (A).

The term "aromatic amino acid" refers to a hydrophobic amino acid with a side chain having at least one aromatic or heteroaromatic ring. In some embodiments, the aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

The term "aliphatic amino acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the preferred embodiments Cys (C) is categorized as a polar hydrophilic amino acid, notwithstanding the general classifications defined above.

As used herein, the term "conjugation moiety" refers to a molecular entity that includes a group that forms a covalent bond by reacting with a function group of a targeting moiety. In some embodiments, the conjugation moiety may react with an amino acid functional group of a monoclonal antibody (mAB).

As used herein, the term "targeting moiety" refers to a structure that binds or associates with a biological moiety or fragment thereof.

In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide. In some embodiments, the targeting moiety may be RNA or DNA. In some embodiments, the targeting moiety may be a RNA or DNA fragment. In some embodiments, the targeting moiety may be a small molecule ligand or nucleic acid aptamer.

In some embodiments, the targeting moiety may be an antibody fragment described in Janthur et al., "Drug Conjugates Such as Antibody Drug Conjugates (ADCs), Immunotoxins and Immunoliposomes Challenge Daily Clinical Practice," *Int. J. Mol. Sci.* 2012, 13, 16020-16045, the disclosure of which is incorporated herein by reference in its entirety. In some embodiments, the targeting moiety may be an antibody fragment described in Trail, P A, "Antibody Drug Conjugates as Cancer Therapeutics," *Antibodies* 2013, 2, 113-129, the disclosure of which is incorporated herein by reference in its entirety.

In some embodiments, the targeting moiety may be an anti-HER2 antibody. In some embodiments, the targeting moiety may be an anti-EGFR antibody.

In some embodiments, the targeting moiety may be HuM195-Ac-225, HuM195-Bi-213, Anyara (naptumomab estafenatox; ABR-217620), AS1409, Zevalin (ibritumomab tiuxetan), BIIBO15, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544. In some embodiments, the targeting moiety may comprise, consist of, or consist essentially of the antibody portion of HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544.

In some embodiments, the targeting moiety may be Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of the antibody portion of Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of Brentuximab, Inotuzumab, Gemtuzumab, Milatuzumab, Trastuzumab, Glembatumomab, Lorvotuzumab, or Labestuzumab.

As used herein, the term "linker" refers to a moiety that connects two or more components to each other.

In some embodiments, the linker may be a linker disclosed in Janthur et al., "Drug Conjugates Such as Antibody Drug Conjugates (ADCs), Immunotoxins and Immunoliposomes Challenge Daily Clinical Practice," *Int. J. Mol. Sci.* 2012, 13, 16020-16045. In some embodiments, the linker may be a linker disclosed in Trail, P A, "Antibody Drug Conjugates as Cancer Therapeutics," *Antibodies* 2013, 2, 113-129. In some embodiments, the linker may be a linker disclosed in U.S. Pat. No. 7,829,531.

In some embodiments, the linker may comprise, consist of, or consist essentially of the linker portion of HuM195-Ac-225, HuM195-Bi-213, Anyara (naptumomab estafenatox; ABR-217620), AS1409, Zevalin (ibritumomab tiuxetan), BIIBO15, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544.

In some embodiments, the linker may comprise, consist of, or consist essentially of the linker portion of Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

While the above-defined categories have been exemplified in terms of the genetically encoded amino acids, the amino acid substitutions need not be, and in certain embodiments preferably are not, restricted to the genetically encoded amino acids. In some embodiments, the active agent-conjugate may contain genetically non-encoded amino acids. Thus, in addition to the naturally occurring genetically encoded amino acids, amino acid residues in the active agent-conjugate may be substituted with naturally occurring non-encoded amino acids and synthetic amino acids.

Certain commonly encountered amino acids which provide useful substitutions for the active agent-conjugates include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); omithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-phenylphenylalanine, 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH$_2$)); N-methyl valine (Me-Val); homocysteine (hCys), homophenylalanine (hPhe) and homoserine (hSer); hydroxyproline (Hyp), homoproline (hPro), N-methylated amino acids and peptoids (N-substituted glycines).

Other amino acid residues not specifically mentioned herein can be readily categorized based on their observed physical and chemical properties in light of the definitions provided herein.

The classifications of the genetically encoded and common non-encoded amino acids according to the categories defined above are summarized in Table 2, below. It is to be understood that Table 2 is for illustrative purposes only and does not purport to be an exhaustive list of amino acid residues and derivatives that can be used to substitute the active agent-conjugate described herein.

TABLE 2

CLASSIFICATIONS OF COMMONLY ENCOUNTERED AMINO ACIDS

| Classification | Genetically Encoded | Non-Genetically Encoded |
|---|---|---|
| Hydrophobic | | |
| Aromatic | F, Y, W | Phg, Nal, Thi, Tic, Phe (4-Cl), Phe (2-F), Phe (3-F), Phe (4-F), hPhe |
| Nonpolar | L, V, I, M, G, A, P | t-BuA, t-BuG, MeIle, Nle, MeVal, Cha, McGly, Aib |
| Aliphatic | A, V, L, I | b-Ala, Dpr, Aib, Ahx, MeGly, t-BuA, t-BuG, MeIle, Cha, Nle, MeVal |

TABLE 2-continued

CLASSIFICATIONS OF COMMONLY ENCOUNTERED AMINO ACIDS

| Classification | Genetically Encoded | Non-Genetically Encoded |
|---|---|---|
| Hydrophilic | | |
| Acidic | D, E | |
| Basic | H, K, R | Dpr, Orn, hArg, Phe(p-NH$_2$), Dbu, Dab |
| Polar | C, Q, N, S, T | Cit, AcLys, MSO, bAla, hSer |
| Helix-Breaking | P, G | D-Pro and other D-amino acids (in L-peptides) |

Other amino acid residues not specifically mentioned herein can be readily categorized based on their observed physical and chemical properties in light of the definitions provided herein.

While in most instances, the amino acids of the compound-conjugate will be substituted with L-enantiomeric amino acids, the substitutions are not limited to L-enantiomeric amino acids. In some embodiments, the peptides may advantageously be composed of at least one D-enantiomeric amino acid. Peptides containing such D-amino acids are thought to be more stable to degradation in the oral cavity, gut or serum than are peptides composed exclusively of L-amino acids.

Examples of compounds of Formula I include, but are not limited to, the following compounds:

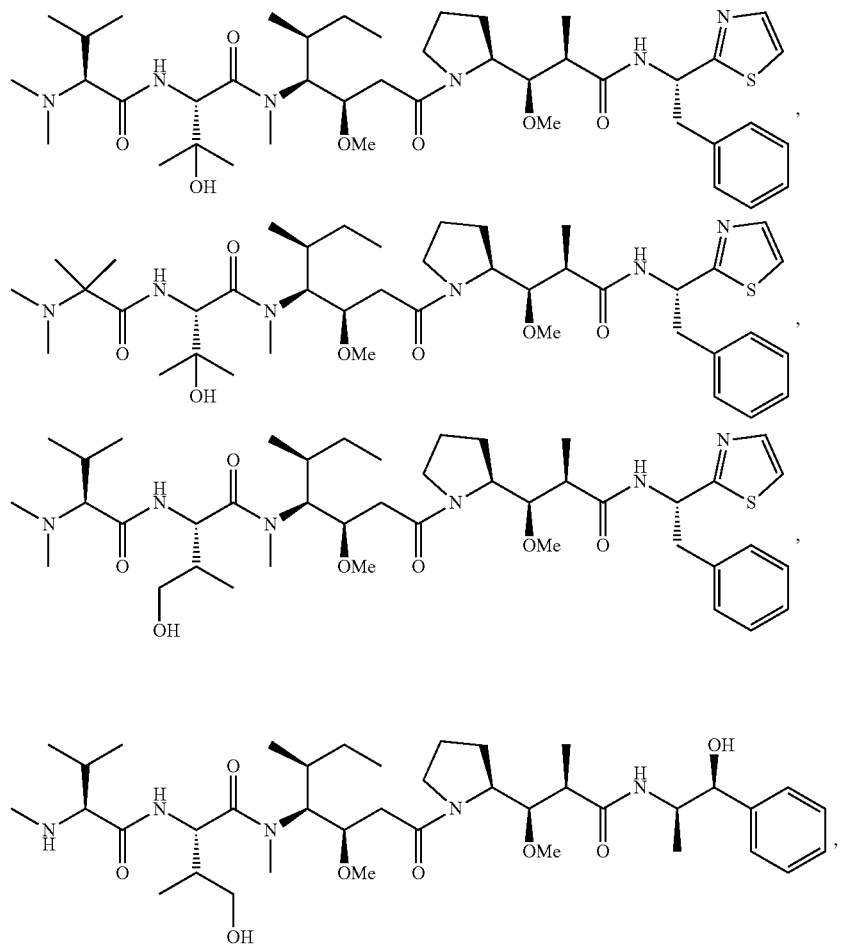

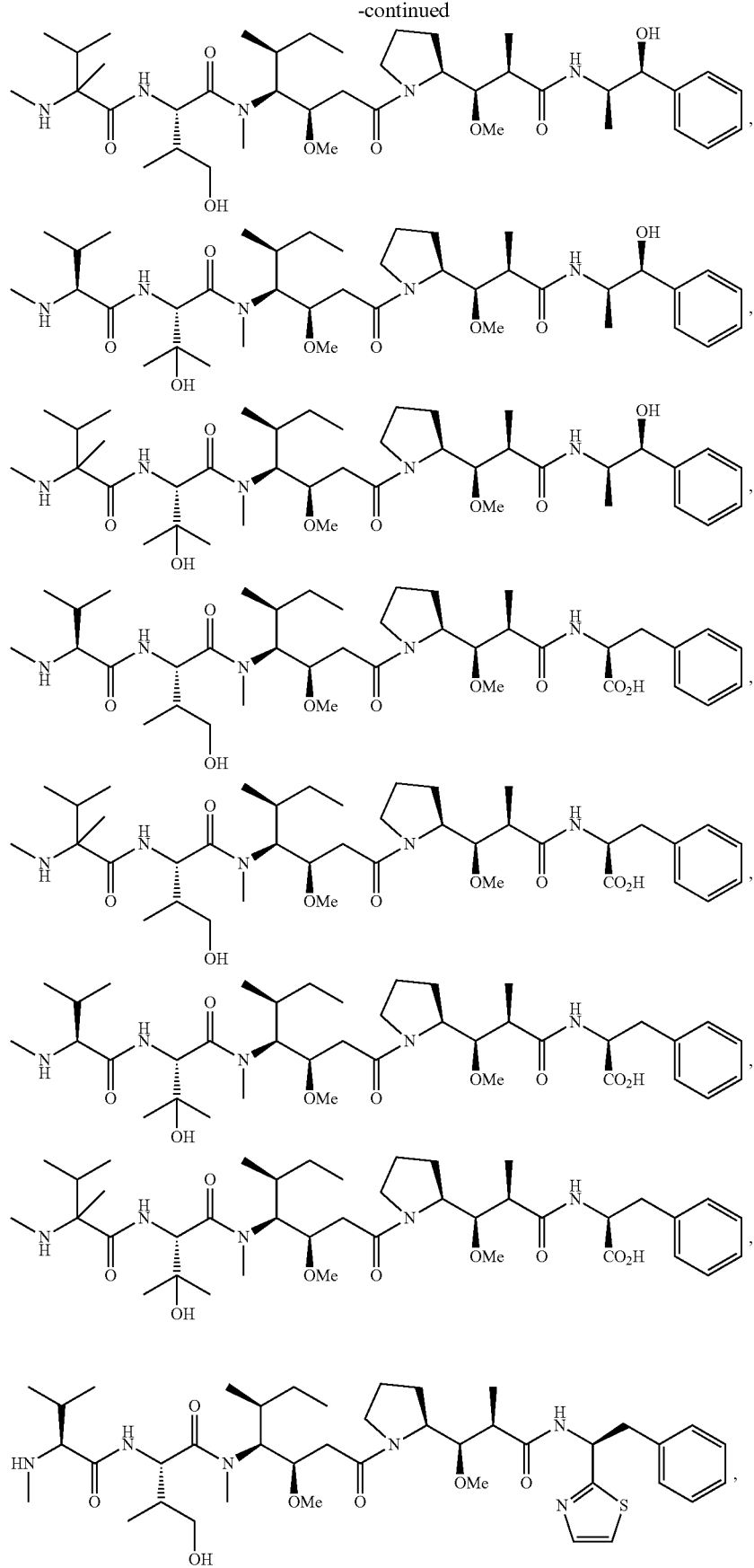

-continued
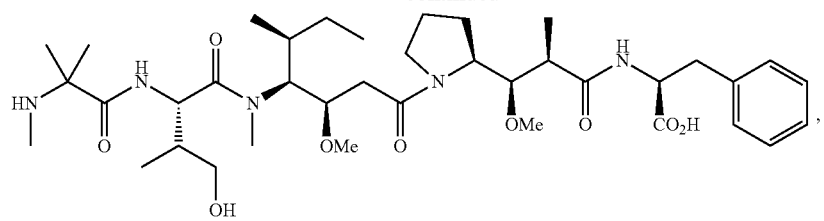,
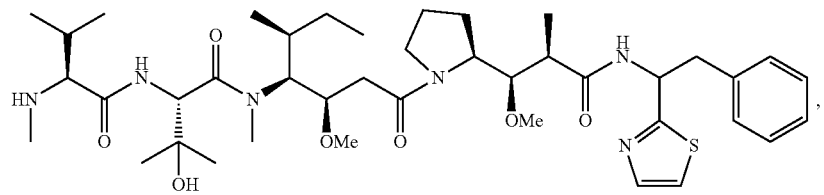,
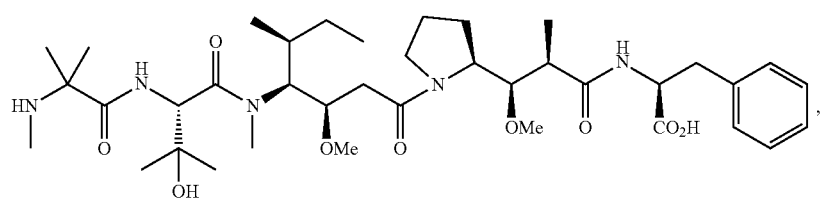,
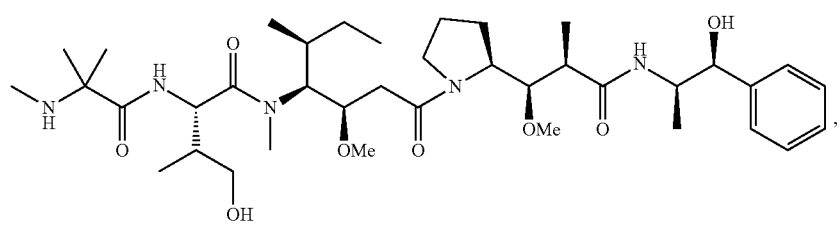,
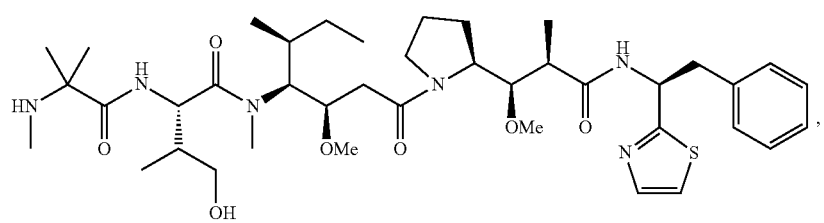,
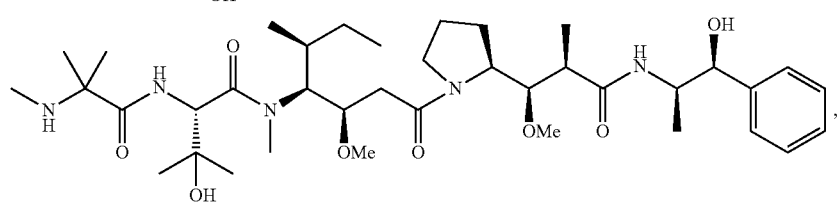,
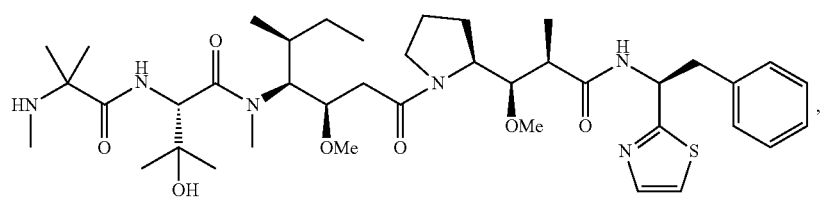,
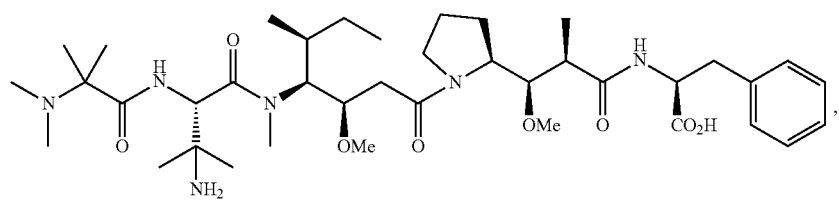,

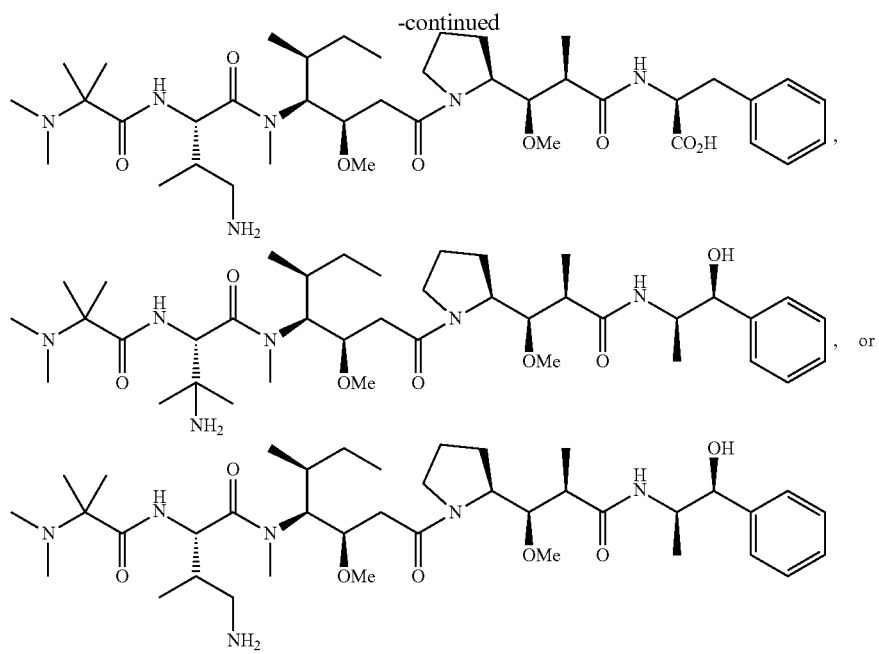

or pharmaceutically acceptable salts or solvates thereof.

Pharmaceutical Compositions

In some embodiments, the compounds disclosed herein are used in pharmaceutical compositions. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents can be provided in the pharmaceutical composition. For example, sodium benzoate, ascorbic acid and esters of p-hydroxybenzoic acid can be added as preservatives. In addition, antioxidants and suspending agents can be used.

The compositions can be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

To formulate the compounds of Formulae I and II as an anti-cancer agent, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing preferred ingredients, sweeteners, fragrances, colorants, preservatives and the like can be added to the administered formulation of the compound produced by the method of the embodiment, particularly when the compound is to be administered orally.

When used as an anti-cancer compound, for example, the compounds of Formulae I and II or compositions including compounds of Formulae I and II can be administered by either oral or non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like.

In one embodiment, the anti-cancer agent can be mixed with additional substances to enhance their effectiveness.

Methods of Administration

In an alternative embodiment, the disclosed compounds and the disclosed pharmaceutical compositions are administered by a particular method as an anti-cancer, or anti-inflammatory agent. Such methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery. As further examples of such modes of administration and as further disclosure of modes of administration, disclosed herein are various methods for administration of the disclosed compounds and pharmaceutical compositions including modes of administration through intraocular, intranasal, and intraauricular pathways.

The pharmaceutically effective amount of the compositions that include the described compounds required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. In a typical embodiment, a compound represented by Formulae I and II can be administered to a patient in need of an anti-cancer agent, until the need is effectively reduced or preferably removed.

In practicing the methods of the embodiment, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages can be between about 10 mg/kg and 100 mg/kg body weight, preferably between about 100 mg/kg and 10 mg/kg body weight. Alternatively dosages can be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above can be used in veterinary medicine.

Depending on the specific conditions being treated, such agents can be formulated and administered systemically or locally. A variety of techniques for formulation and administration can be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the embodiment can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the embodiment into dosages suitable for systemic administration is within the scope of the embodiment. With proper choice of carrier and suitable manufacturing practice, the compositions disclosed herein, in particular, those formulated as solutions, can be administered parenterally, such as by intravenous injection. The compounds can be formulated readily using pharmaceutically acceptable carriers well known in the art into dosages suitable for oral administration. Such carriers enable the compounds of the embodiment to be formulated as tablets, pills, capsules, liquids, gels, syrups, slurries, suspensions and the like, for oral ingestion by a patient to be treated.

Agents intended to be administered intracellularly can be administered using techniques well known to those of ordinary skill in the art. For example, such agents can be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration can be in the form of tablets, dragees, capsules, or solutions. The pharmaceutical compositions can be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, can be determined using known methods. The efficacy of a particular compound can be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfunction, and infectious diseases. Similarly, acceptable animal models can be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

As will be understood by one of skill in the art, "need" is not an absolute term and merely implies that the patient can benefit from the treatment of the anti-cancer agent in use. By "patient" what is meant is an organism that can benefit by the use of an anti-cancer agent.

"Therapeutically effective amount," "pharmaceutically effective amount," or similar term, means that amount of drug or pharmaceutical agent that will result in a biological or medical response of a cell, tissue, system, animal, or human that is being sought. In a preferred embodiment, the medical response is one sought by a researcher, veterinarian, medical doctor, or other clinician.

In one embodiment, a described compound, preferably a compound of any one of Formula I and/or II, including those as described herein, is considered an effective anti-cancer agent if the compound can influence 10% of the cancer cells, for example. In a more preferred embodiment, the compound is effective if it can influence 10 to 50% of the cancer cells. In an even more preferred embodiment, the compound is effective if it can influence 50-80% of the cancer cells. In an even more preferred embodiment, the compound is effective if it can influence 80-95% of the cancer cells. In an even more preferred embodiment, the compound is effective if it can influence 95-99% of the cancer cells. "Influence" is defined by the mechanism of action for each compound.

Some embodiments include methods of delivering a drug molecule to an in vivo mammalian cell by administering to the mammal an antibody-drug conjugate comprising a drug moiety. In some embodiments the administration is parenteral (e.g., intravenously). In other embodiments, the administration is oral. In some embodiments, that antibody-drug conjugate comprises an antibody, a chemical linker as described herein, and the drug moiety.

Methods of Treatment

Some embodiments include methods of treating cancer by administering a compound of any one of Formula I and/or II to a subject in need of cancer therapy. Non-limiting cancers that can be treated using the compounds described herein include bladder cancer, breast cancer, colon cancer, rectal cancer, endometrial cancer, kidney cancer, lung cancer, melanoma, non-Hodgkin lymphoma, glioblastoma, pancreatic cancer, prostate cancer, and thyroid cancer.

Some embodiments include the treatment of cancer including, but not limited to a carcinoma, a sarcoma, a lymphoma, a leukemia, and a blastoma. Non-limiting cancers that can be treated using the compounds described herein include bladder cancer, breast cancer, colon cancer, rectal cancer, endometrial cancer, kidney cancer, lung cancer, melanoma, non-Hodgkin lymphoma, leukemia, glioblastoma, pancreatic cancer, prostate cancer, and thyroid cancer.

Some embodiments include the treatment of cancer including, but not limited to a carcinoma, a sarcoma, a lymphoma, a leukemia, and a blastoma. Non-limiting cancers that can be treated using the compounds described herein include bladder cancer, breast cancer, colon cancer, rectal cancer, endometrial cancer, kidney cancer, lung cancer, melanoma, non-Hodgkin lymphoma, leukemia, glioblastoma, pancreatic cancer, prostate cancer, and thyroid cancer.

Some embodiments provide a method of treating a cancer comprising administering a compound of Formula I or II, or a pharmaceutically acceptable salt thereof to a subject in need thereof. In some embodiments, the cancer is leukemia. In some embodiments, the cancer is multiple myeloma.

Some embodiments provide a method of treating melanoma, comprising administering a compound of Formula I or II, or a pharmaceutically acceptable salt thereof to a subject in need thereof. Some embodiments provide a method of treating multiple myeloma, comprising administering a compound of Formula I or II, or a pharmaceutically acceptable salt thereof to a subject in need thereof.

Some embodiments provide a use of a compound of Formula II to provide a chemical entity to a target location, where the chemical entity has the following structure:

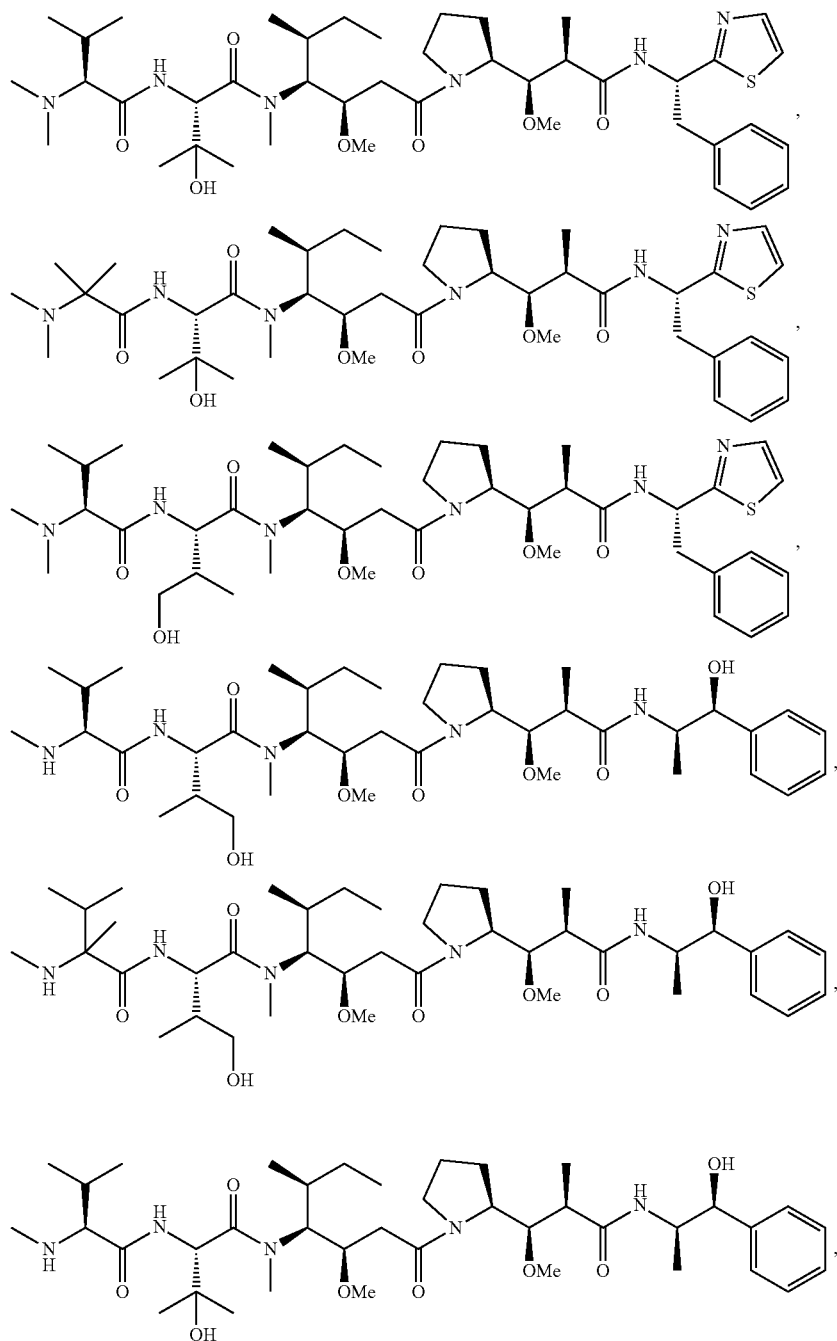

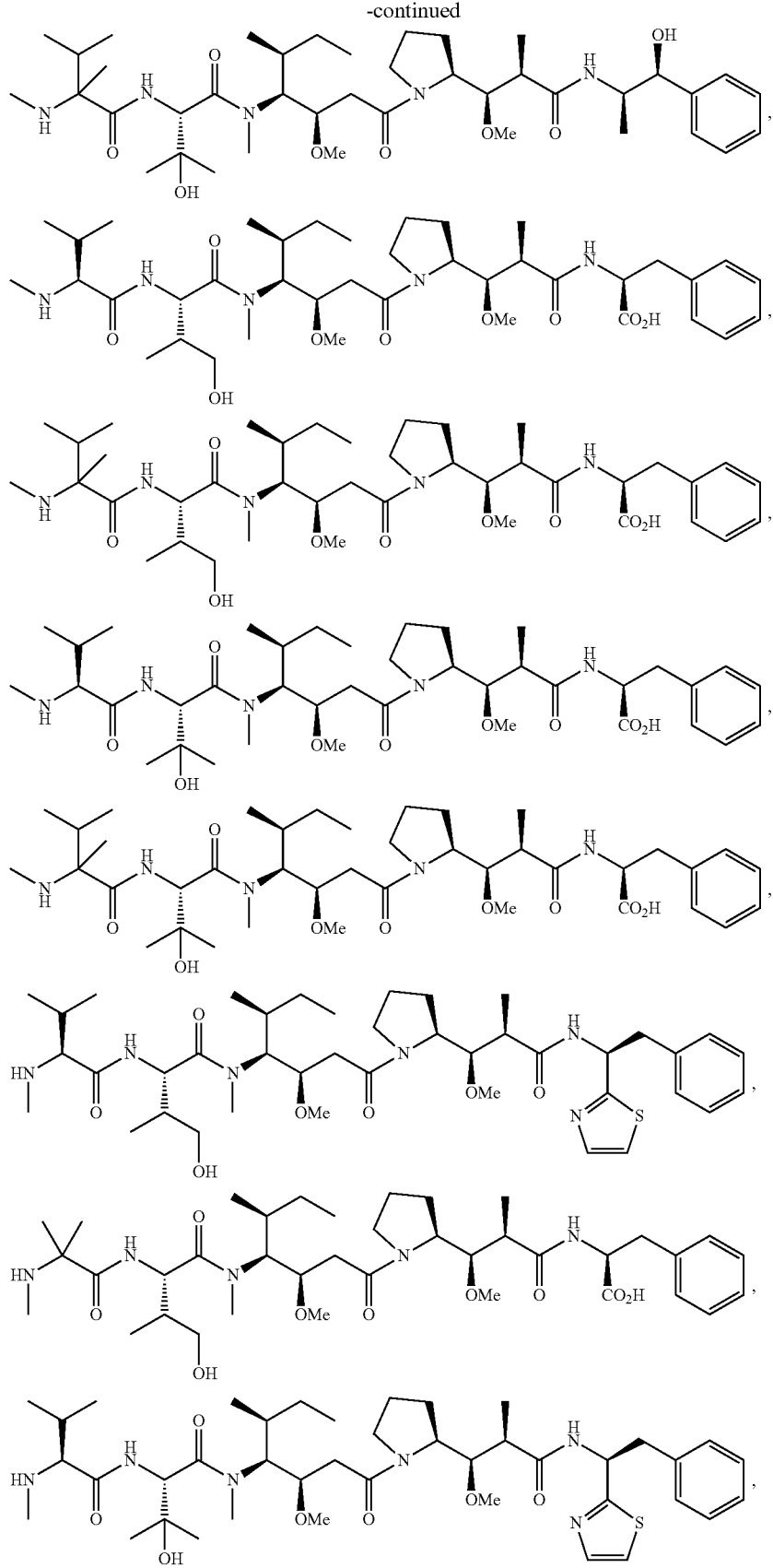

-continued

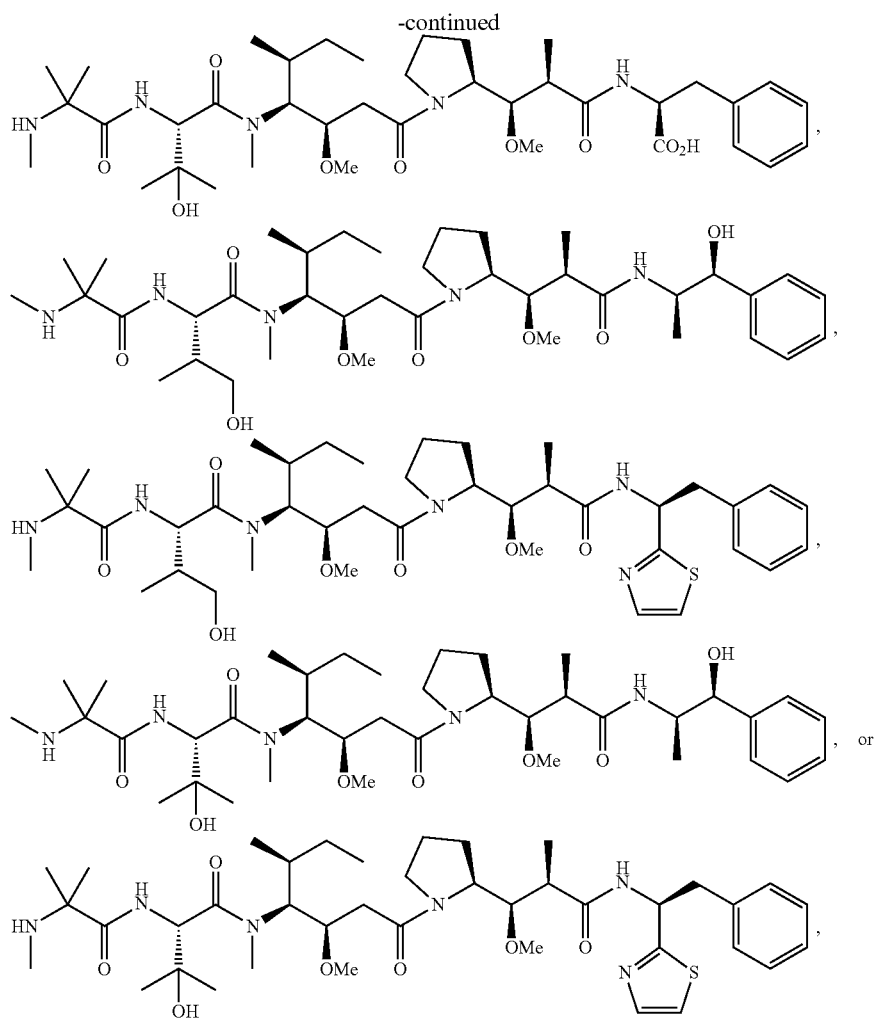

or pharmaceutically acceptable salts or solvates thereof.

In some embodiments, the subject is a human.

Some embodiments provide a method delivering a compound having the structure of Formula I to an in vivo mammalian cell, the method comprising administering a compound having the structure of Formula II to a mammal comprising the in vivo mammalian cell. In some embodiments, the antibody-drug conjugate is administered parenterally. In some embodiments, the antibody-drug conjugate is administered intravenously. In some embodiments, the antibody-drug conjugate is administered orally.

Some embodiments provide use of a compound having the structure of Formula II to provide a compound having the structure of Formula I to a target location.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

The term "patient" includes human and animal subjects.

The term "contacting" refers to bringing two or more materials into close enough proximity that they may interact. In certain embodiments, contacting can be accomplished in a vessel such as a test tube, a petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may dead. Cells may or may not be intact.

EXAMPLES

The following examples are set forth merely to assist in understanding the embodiments and should not be construed as limiting the embodiments described and claimed herein in any way. Variations of the invention, including the substitution of all equivalents now known or later developed, which would be within the purview of those skilled in the art, and changes in formulation or minor changes in experimental design, are to be considered to fall within the scope of the invention incorporated herein.

Example 1

General Procedure A—Synthesis of Compounds of Formula I

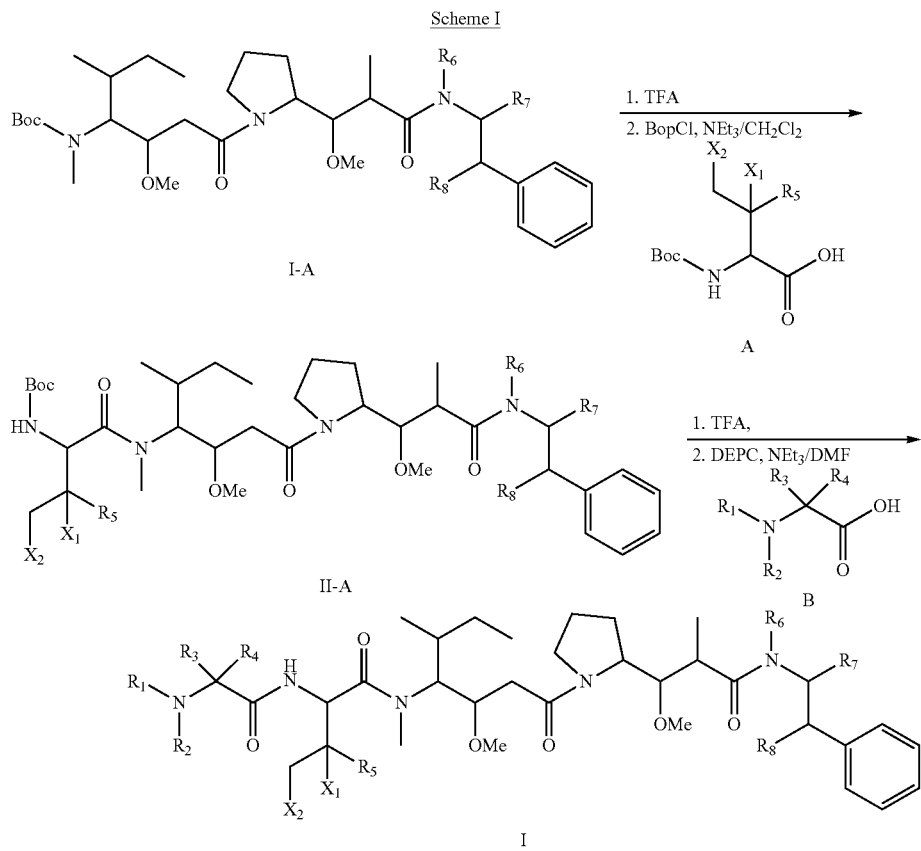

A compound of General Formula I may be synthesized following procedures known in the art with appropriate modifications such as disclosed in Hamada et al., "Efficient stereoselective synthesis of dolastatin 10, an antineoplastic peptide from a sea hare," Tetrahedron Lett., 1991, 32(7): 931-934. For example, a compound of General Formula I-A may be treated with TFA to afford a secondary amine intermediate that may be reacted with a compound of General Formula A under coupling conditions, such as BopCl, $NEt_3/CH_2Cl_2$, to afford a compound of General Formula II-A. A compound of General Formula II-A may be then treated with TFA to afford a primary amine intermediate that may be reacted with a compound of General Formula B under coupling conditions, such as DEPC, $NEt_3/DMF$, to afford a compound of General Formula I.

Synthesis of General Formula A

Synthesis of Amino Acid with Olefin Intermediate

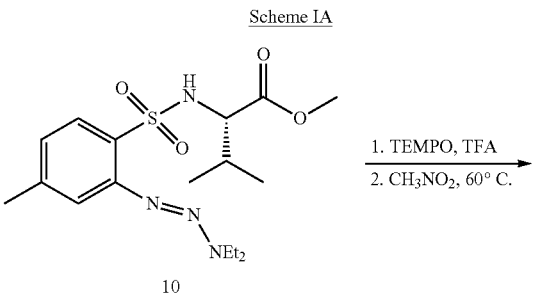

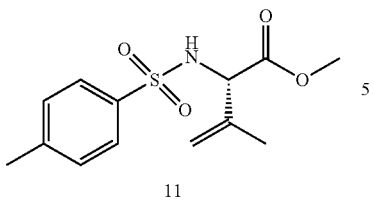

11

Compound 11 may be made according to the procedure disclosed in Voica, et al., "Guided desaturation of unactivated aliphatics," Nature Chemistry, 2012, 4: 629-635.

Scheme IB

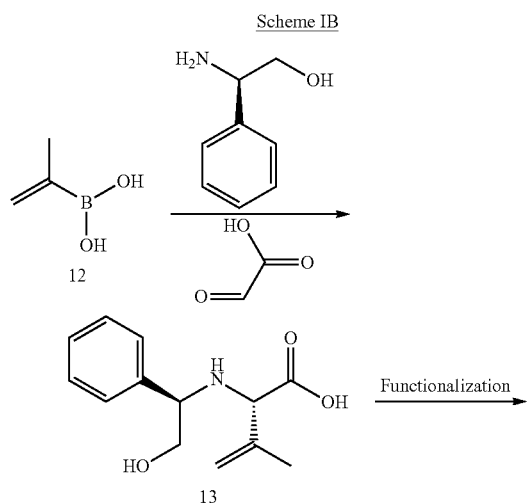

Compound 13 may be synthesized following procedures known in the art with appropriate modifications such as disclosed in Petasis, et al., "A New and Practical Synthesis of α-Amino Acids from Alkenyl Boronic Acids," J. Am. Chem. Soc., 1997, 119, 445-446. Compound 13 may be further functionalized by methods known in the art to afford a compound of General Formula IB-1. The compound of General Formula IB-1 may be subjected to hydrogenation to afford a compound of General Formula IB-2. The compound of General Formula IB-2 may be treated with (Boc)₂O under the appropriate conditions to afford a compound of General Formula A.

Synthesis of Halogen Compounds of General Formula A

Scheme IC

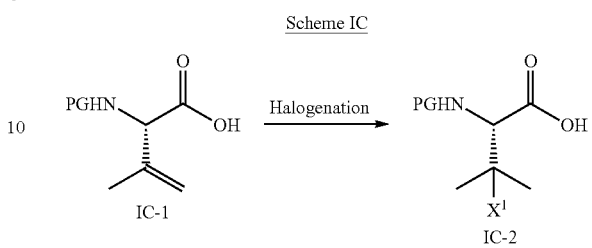

A compound of General Formula IC-2 (where PG is a protecting group such as Boc or as shown in Scheme IA and Scheme IB) may be synthesized from a compound of General Formula IC-1 (where PG is a protecting group such as Boc or as shown in Scheme IA and Scheme IB), for example compound 11 or compound 13, following procedures known in the art with appropriate modifications such as disclosed in Barker, et al., "Fe(III)/NaBH₄-Mediated Free Radical Hydrofluorination of Unactivated Alkenes," J. Am. Chem. Soc., 2012, 134, 13588-13591 ($X^1$=F) or Gaspar, et al., "Catalytic Hydrochlorination of Unactivated Olefins with para-Toluenesulfonyl Chloride," Angew. Chem. Int. Ed, 2008, 47, 5778-5760 ($X^1$=Cl).

Synthesis of Azide or Amine Compounds of General Formula A

Scheme ID

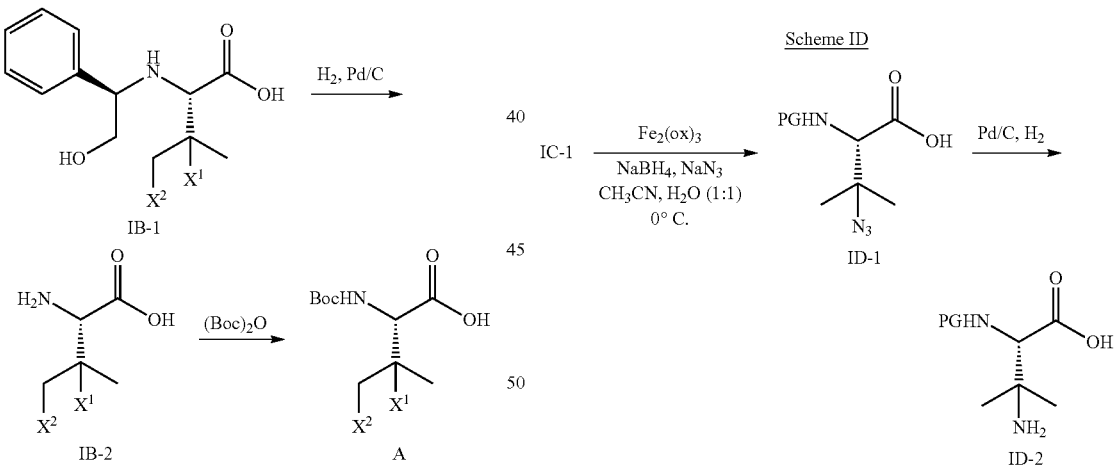

A compound of General Formula ID-1 (where PG is a protecting group such as Boc) or General Formula ID-2 (where PG is a protecting group such as Boc) may be synthesized from a compound of General Formula IC-1, for example compound 11 or compound 13, following procedures known in the art with appropriate modifications such as disclosed in Leggans, et al., "Iron(III)/NaBH4-Mediated Additions to Unactivated Alkenes: Synthesis of Novel 20'-Vinblastine Analogues," Org. Lett., 2012, 14, 1428-1431 or Waser, et al., "Cobalt-Catalyzed Hydroazidation of Olefins: Convenient Access to Alkyl Azides," J. Am. Chem. Soc., 2005, 127, 8294-8295.

Synthesis of Hydroxy Compounds of General Formula A

Scheme IE

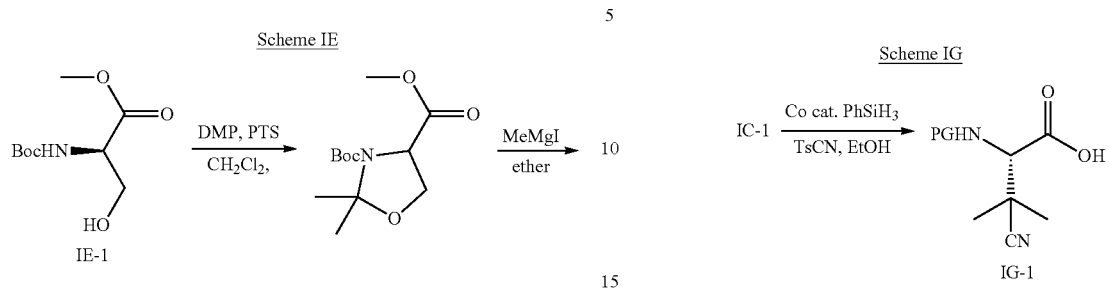

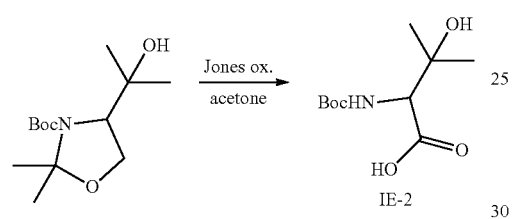

A compound of General Formula IE-2 may be synthesized from a compound of General Formula IE-1 following the procedure disclosed in Yonezawa, et al., "Facile Synthesis of L-3,4-Didehydrovaline Constituting an Antibiotic, Phomopsin A," Synthesis, 2000, 5, 634-636.

Scheme 1F

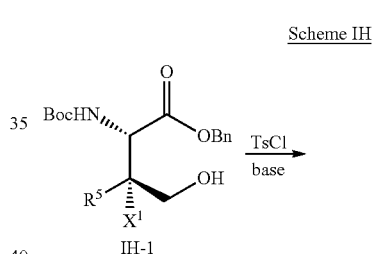

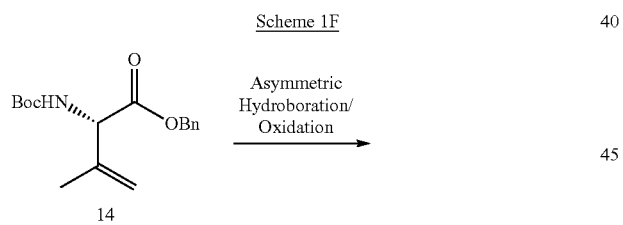

Compounds 15 and 16 may be synthesized from compound 14 following procedures known in the art.

Synthesis of Cyano Compounds of General Formula A

Scheme IG

IC-1 $\xrightarrow[\text{TsCN, EtOH}]{\text{Co cat. PhSiH}_3}$ PGHN — ... — OH, CN

IG-1

A compound of General Formula IG-1 (where PG is a protecting group such as Boc) may be synthesized from a compound of General Formula IC-1 following procedures known in the art with appropriate modifications such as disclosed in Gaspar, et al., "Catalytic Hydrochlorination of Unactivated Olefins with para-Toluenesulfonyl Chloride," Angew. Chem. Int. Ed, 2008, 47, 5778-5760 and references cited therein.

Synthesis of Compounds of General Formula G

Scheme IH

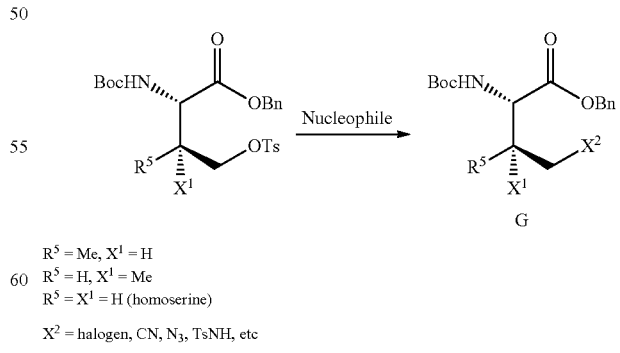

$R^5 = Me, X^1 = H$
$R^5 = H, X^1 = Me$
$R^5 = X^1 = H$ (homoserine)

$X^2$ = halogen, CN, N$_3$, TsNH, etc

Compounds of General Formula G may be synthesized from a compound of General Formula IH-1 following procedures known in the art with appropriate modifications.

Synthesis of Compound 101

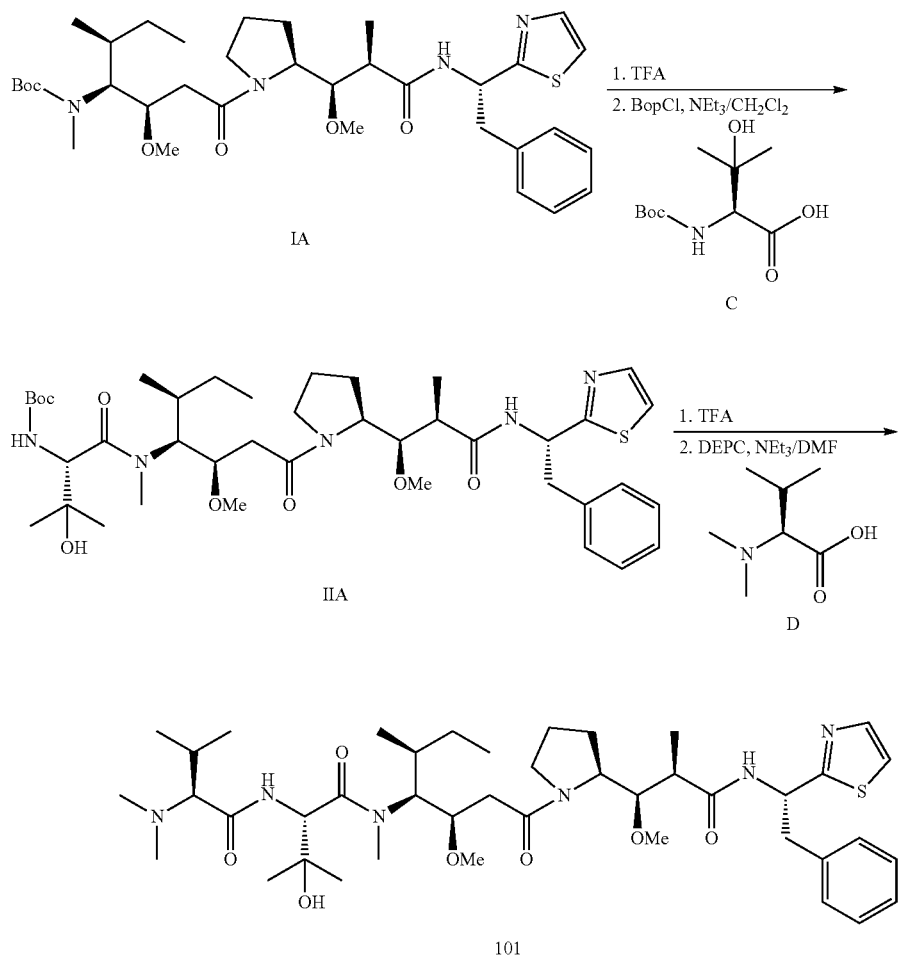

Compound 101 was synthesized using a procedure similar to Scheme I-A above and following procedures known in the art with appropriate modifications such as disclosed in Hamada et al., "Efficient stereoselective synthesis of dolastatin 10, an antineoplastic peptide from a sea hare," Tetrahedron Lett., 1991, 32(7): 931-934. For example, compound IA may be treated with TFA to afford a secondary amine intermediate that may be reacted with a compound C under coupling conditions, such as BopCl, NEt$_3$/CH$_2$Cl$_2$, to afford compound IIA. Compound IIA may be then treated with TFA to afford a primary amine intermediate that may be reacted with compound D under coupling conditions, such as DEPC, NEt$_3$/DMF, to afford a compound 101. The MS2 fragmentation pattern of compound 101 was measured and determined to be similar to that of Dolastatin10 and Symplostatin-1, which confirms the structure of compound 101.

Synthesis of Compound 102

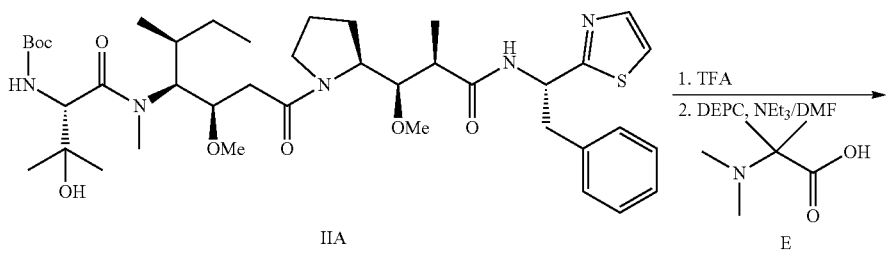

-continued

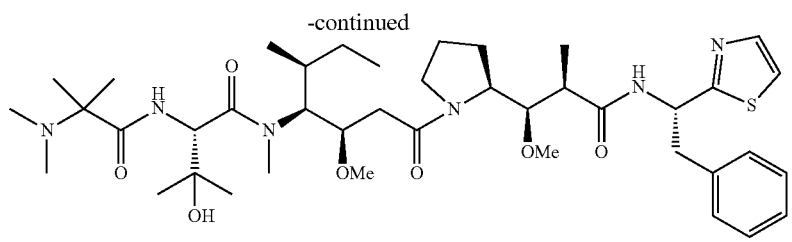

102

Compound 102 may be synthesized following procedures known in the art with appropriate modifications such as disclosed in Hamada et al., "Efficient stereoselective synthesis of dolastatin 10, an antineoplastic peptide from a sea hare," Tetrahedron Lett., 1991, 32(7): 931-934. For example, compound IIA may be then treated with TFA to afford a primary amine intermediate that may be reacted with compound E under coupling conditions, such as DEPC, NEt$_3$/DMF, to afford a compound 102.

Synthesis of Compound 103

Scheme I-C

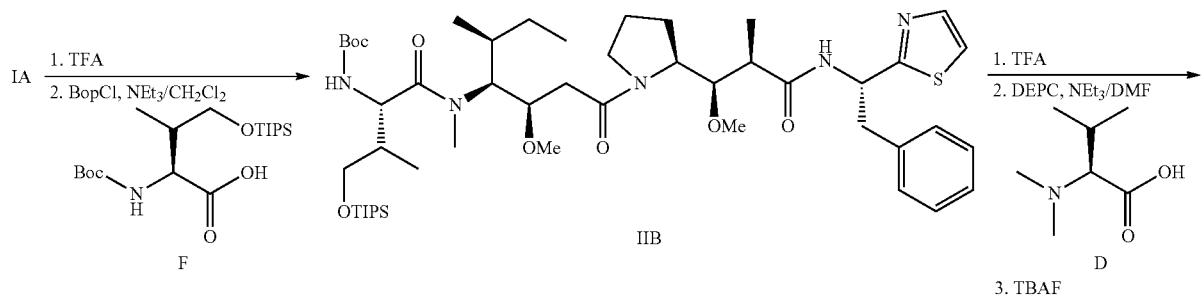

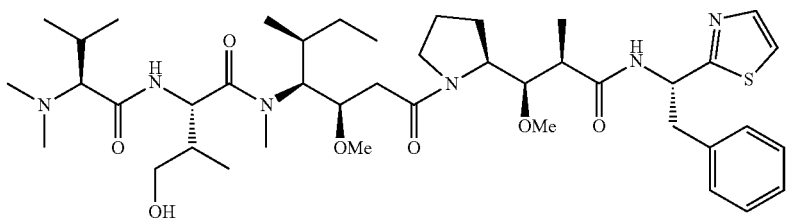

103

Compound 103 may be synthesized following procedures known in the art with appropriate modifications such as disclosed in Hamada et al., "Efficient stereoselective synthesis of dolastatin 10, an antineoplastic peptide from a sea hare," Tetrahedron Lett., 1991, 32(7): 931-934. For example, compound IA may be treated with TFA to afford a secondary amine intermediate that may be reacted with a compound F under coupling conditions, such as BopCl, NEt$_3$/CH$_2$Cl$_2$, to afford compound IIB. Compound IIB may be then treated with TFA to afford an intermediate that may be reacted with compound D under coupling conditions, such as DEPC, NEt$_3$/DMF, to afford a compound 103.

Synthesis of Compound 101, 104, 105 and 106
Scheme I-A1:
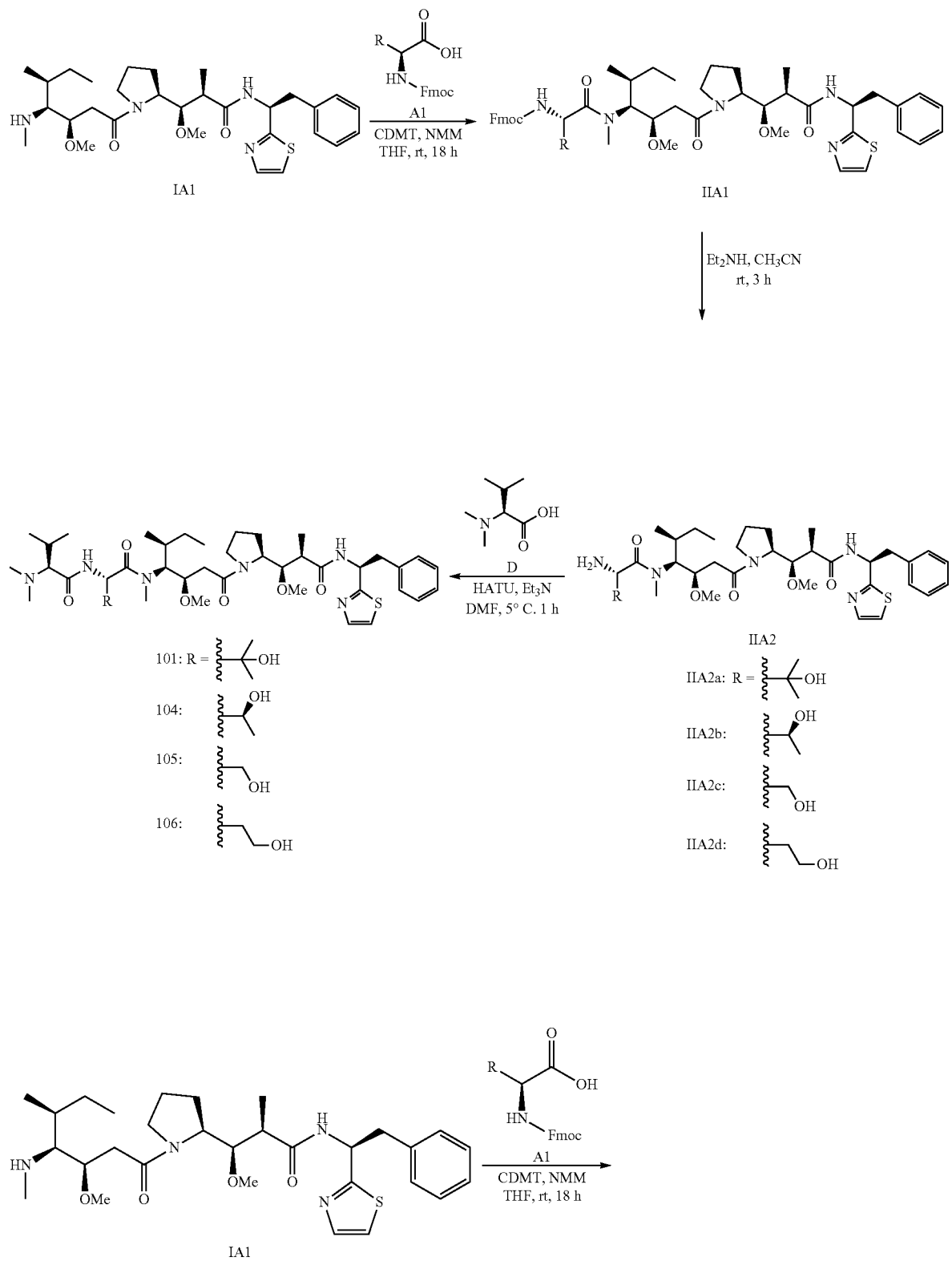

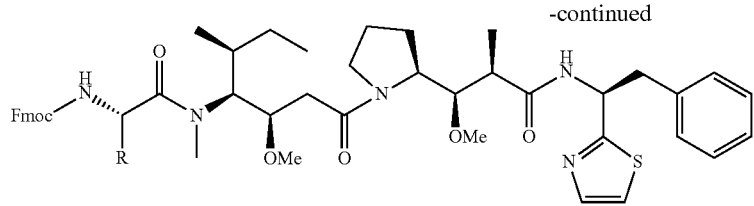

IIA1

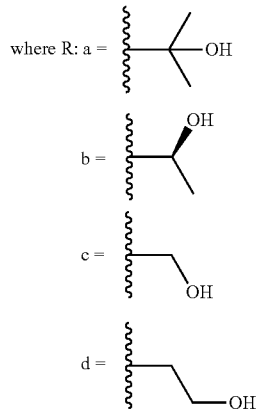

A reaction chamber equipped with magnetic stirbar was charged with IA1 (0.1 mmol), Fmoc-(S)-amino acid (0.2 mmol, 2.0 equiv.), and CDMT (2-chloro-4,6-dimethoxy-1,3,5-triazine, 0.2 mmol, 2.0 equiv.). The reaction chamber was flushed with Ar and the materials were dissolved in anhydrous THF (0.05 M) followed by slow addition of N-methylmorpholine (0.35 mmol, 3.5 equiv.) over 2 min. The pale yellow solution was allowed to stir at rt under Ar for 18 h. Subsequently, the crude mixture was loaded onto HP20ss (2 g), and purified via CombiFlash Rf (C18 15.5 g, 30 mL/min, $CH_3CN/H_2O$ linear gradient from 35-100% $CH_3CN$ over 12 min ramp). The desired products (IIA1a to IIA1d) were isolated as a colorless oil (55-70% yields).

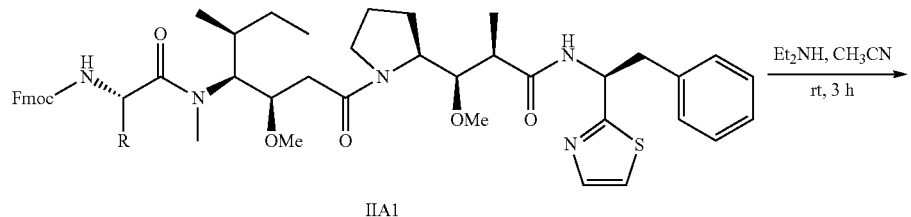

IIA1

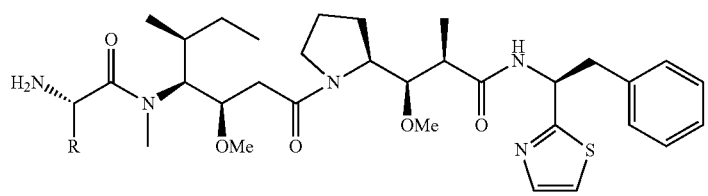

IIA2 where R: a = 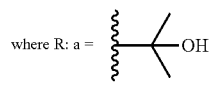

b = 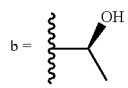

c = 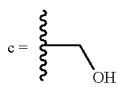

d = 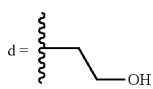

A reaction chamber equipped with magnetic stirbar was charged with Fmoc-tetrapeptide, IIA1 (0.05 mmol). The material was dissolved in $CH_3CN$ (0.01 M) followed by diethylamine (1.25 mmol, 25 equiv.) addition at rt and the resulting mixture was allowed to stir for 3 h. The mixture was extracted with pentane (3×3 mL) and concentrated to yield crude material as oil. The crude material was subjected to next step without further purification (90-94% yields).

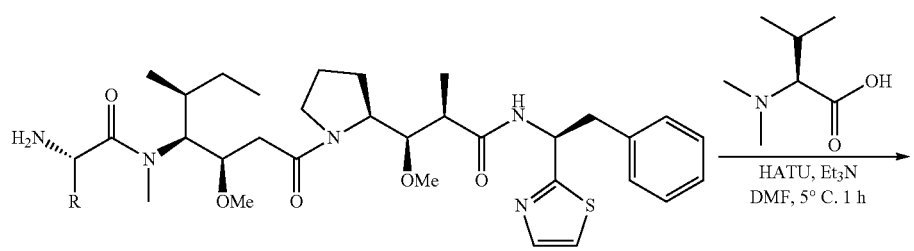

IIA2 where R: a = 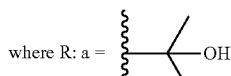

b = 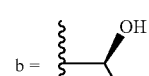

c = 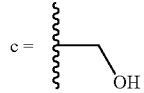

d = 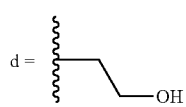

-continued

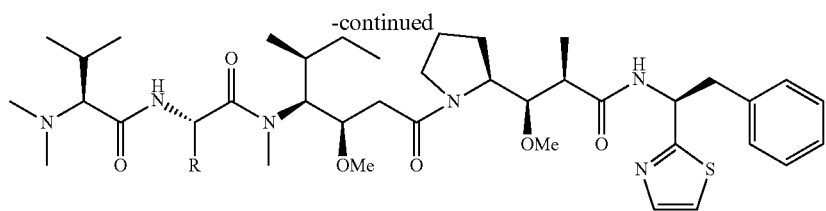

IIA2

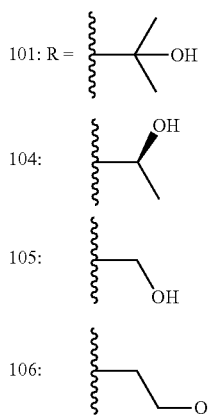

A reaction chamber equipped with magnetic stirbar was charged with tetrapeptide, IIA2 (0.05 mmol) and N,N-dimethyl-L-valine (0.1 mmol, 2 equiv.). The materials were dissolved in anhydrous DMF (0.05 M) and cooled in an ice bath (~5° C.) under Ar followed by triethylamine (0.11 mmol, 2.2 equiv.) addition and the resulting mixture was allowed to stir for 5 min at 5° C. A solution of HATU (0.075 mmol, 1.5 equiv.) in anhydrous DMF (0.25 M) was slowly added into the mixture at 5° C. The resulting mixture was allowed to stir in an ice bath for additional 45 min. The mixture was then loaded onto HP20ss (2 g) and purified via CombiFlash Rf (C18 5.5 g, 18 mL/min, $CH_3CN/H_2O$ linear gradient from 30-100% $CH_3CN$ over 14 min ramp). The desired products were isolated as an amorphous solid (80-90% yields). Observed ESI HRMS for compound 101: m/z 801.49798 $[M+H]^+$, compound 104: m/z 787.4815 $[M+H]^+$, compound 105: m/z 773.4662 $[M+H]^+$, and compound 106: m/z 787.4790 $[M+H]^+$.

Synthesis of Compound 107

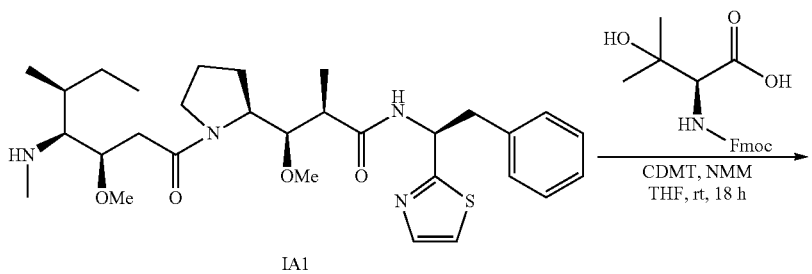

IA1

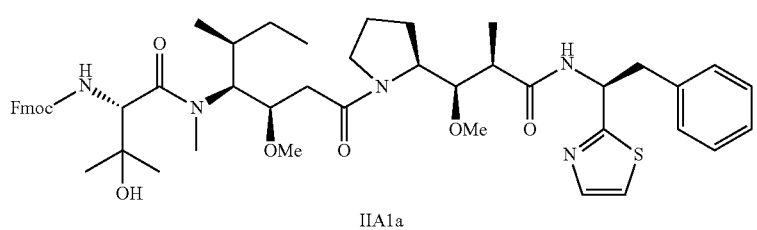

IIA1a

A reaction chamber equipped with magnetic stirbar was charged with IA1 (90 mg, 0.161 mmol), Fmoc-(S)-2-amino-3-hydroxy-3-methylbutanoic acid (114 mg, 0.322 mmol, 2.0 equiv.), and CDMT (2-chloro-4,6-dimethoxy-1,3,5-triazine, 57 mg, 0.322 mmol, 2.0 equiv.). The reaction chamber was flushed with Ar and the materials were dissolved in anhydrous THF (5.0 mL, 0.03 M) followed by slow addition of N-methylmorpholine (62 μL, 0.564 mmol, 3.5 equiv.) over 2 min. The pale yellow solution was allowed to stir at rt under Ar for 18 h. Subsequently, the crude mixture was loaded onto HP20ss (2.5 g), and purified via CombiFlash Rf (C18 15.5 g, 30 mL/min, $CH_3CN/H_2O$ linear gradient from 35-100% $CH_3CN$ over 12 min ramp). The desired product was isolated as a colorless oil (77 mg, 0.086 mmol, 53%).

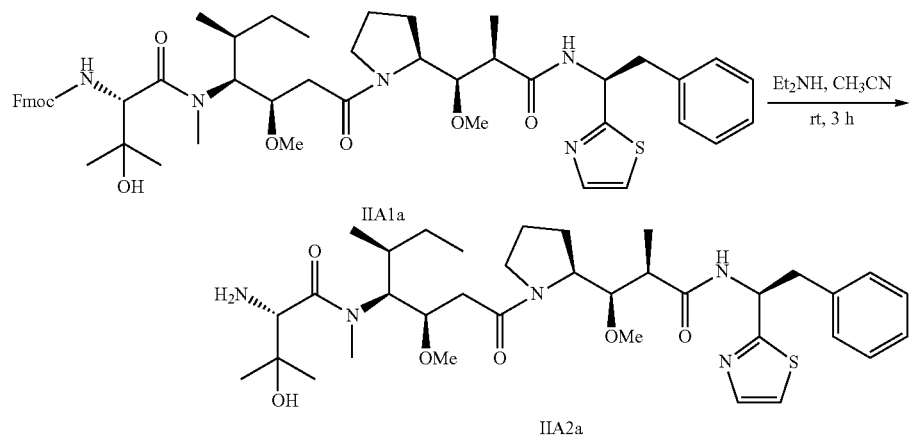

A reaction chamber equipped with magnetic stirbar was charged with Fmoc-tetrapeptide IIA1a (75 mg, 0.084 mmol). The material was dissolved in $CH_3CN$ (4.5 mL) followed by diethylamine (0.219 mL, 2.092 mmol, 25 equiv.) addition at rt and the resulting mixture was allowed to stir for 3 h. The mixture was extracted with pentane (3×3 mL) and concentrated to yield crude material as oil. The crude material was subjected to next step without further purification (53 mg, 0.078 mmol, 94%).

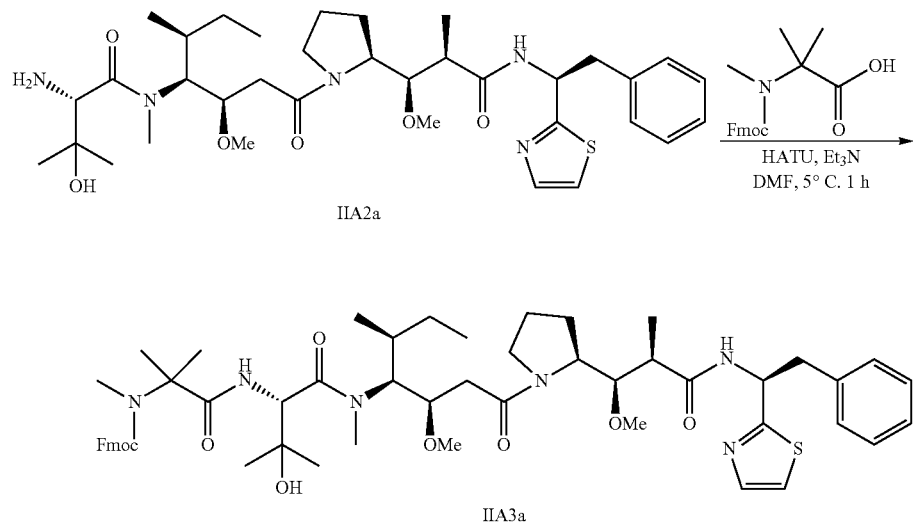

A reaction chamber equipped with magnetic stirbar was charged with free base tetrapeptide (IIA2a, 50 mg, 0.074 mmol) and Fmoc-2-methylaminoisobutyric acid (50 mg, 0.148 mmol, 2 equiv.). The materials were dissolved in anhydrous DMF (1.25 mL) and cooled in an ice bath (~5° C.) under Ar followed by triethylamine (23 μL, 0.163 mmol, 2.2 equiv.) addition and the resulting mixture was allowed to stir for 5 min at 5° C. A solution of HATU (42 mg, 0.111 mmol, 1.5 equiv.) in anhydrous DMF (0.5 mL) was slowly added into the mixture at 5° C. The mixture turned pale yellow and was allowed to stir in an ice bath for additional 45 min. Subsequently, the crude mixture was loaded onto HP20ss (2.5 g) and purified via CombiFlash Rf (C18 5.5 g, 18 mL/min, $CH_3CN/H_2O$ linear gradient from 30-100% $CH_3CN$ over 14 min ramp). The desired product IIA3a was isolated as an amorphous solid (60 mg, 0.06 mmol, 82%).

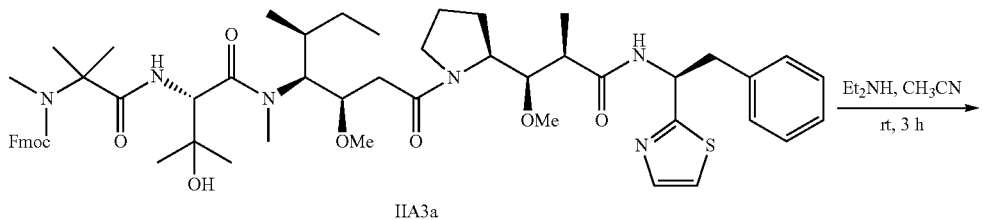

IIA3a

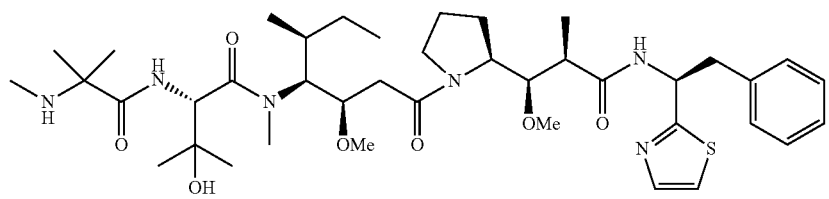

107

A reaction chamber equipped with magnetic stirbar was charged with Fmoc-pentapeptide, IIA3a (60 mg, 0.06 mmol). The material was dissolved in $CH_3CN$ (4.5 mL) and purged with Ar. Diethylamine (0.184 mL, 1.76 mmol, 25 equiv.) was then added at rt and allowed to stir for 3 h. The crude mixture was then loaded onto HP20ss (2 g) and purified using CombiFlash Rf (C18Aq 5.5 g, 18 mL/min, $CH_3CN/H_2O$ linear gradient from 0-50% $CH_3CN$ over 12 min ramp). The desired product, Compound 107 was isolated as a colorless glassy solid (40 mg, 0.052 mmol, 86%). Observed ESI HRMS: m/z 773.4659 $[M+H]^+$. Compound 107 exists as conformers in a 3:2 ratio in $CD_3OD$ solvent; the NMR chemical shifts for the major conformer are listed here. $^1H$ NMR ($CD_3OD$, 600 MHz): δ 7.79 (d, J=3.2 Hz, 1H), 7.53 (d, J=3.2 Hz, 1H), 7.31 (d, J=7.3 Hz, 2H), 7.25 (t, J=7.3 Hz, 2H), 7.21 (d, J=7.3 Hz, 1H), 5.66 (dd, J=4.1, 11.4 Hz, 1H), 5.02 (s, 1H), 4.15 (m, 1H), 3.67 (m, 1H), 3.57 (m, 1H), 3.51 (dd, J=4.5, 14 Hz, 1H), 3.42 (d, J=10.8 Hz, 1H), 3.38 (s, 3H), 3.35 (s, 3H), 3.33 (m, 1H), 3.20 (m, 1H), 3.20 (s, 3H), 3.04 (m, 1H), 2.62 (s, 3H), 2.48 (m, 1H), 2.38 (m, 1H), 2.29 (m, 1H), 1.89 (m, 1H), 1.88 (m, 1H), 1.71 (m, 1H), 1.65 (s, 3H), 1.60 (m, 1H), 1.57 (s, 3H), 1.40 (m, 1H), 1.39 (s, 3H), 1.37 (m, 1H), 1.26 (s, 3H), 1.16 (d, J=6.6 Hz, 3H), 1.04 (m, 1H), 1.01 (d, J=7.3 Hz, 3H), 0.87 (t, J=7.4, 3H). $^{13}C$ NMR ($CD_3OD$, 150 MHz): δ 175.0, 173.9, 173.4, 172.0, 170.1, 143.5, 137.5, 129.8, 129.8, 128.7, 128.7, 127.7, 120.3, 86.4, 73.0, 70.9, 63.1, 61.9, 60.3, 58.4, 58.3, 56.6, 53.0, 47.8, 45.3, 41.3, 36.8, 33.6, 33.1, 28.1, 27.2, 26.7, 26.4, 25.7, 25.3, 21.8, 21.3, 16.2, 14.8, 10.6.

Synthesis of Compound 108, 109 and 110

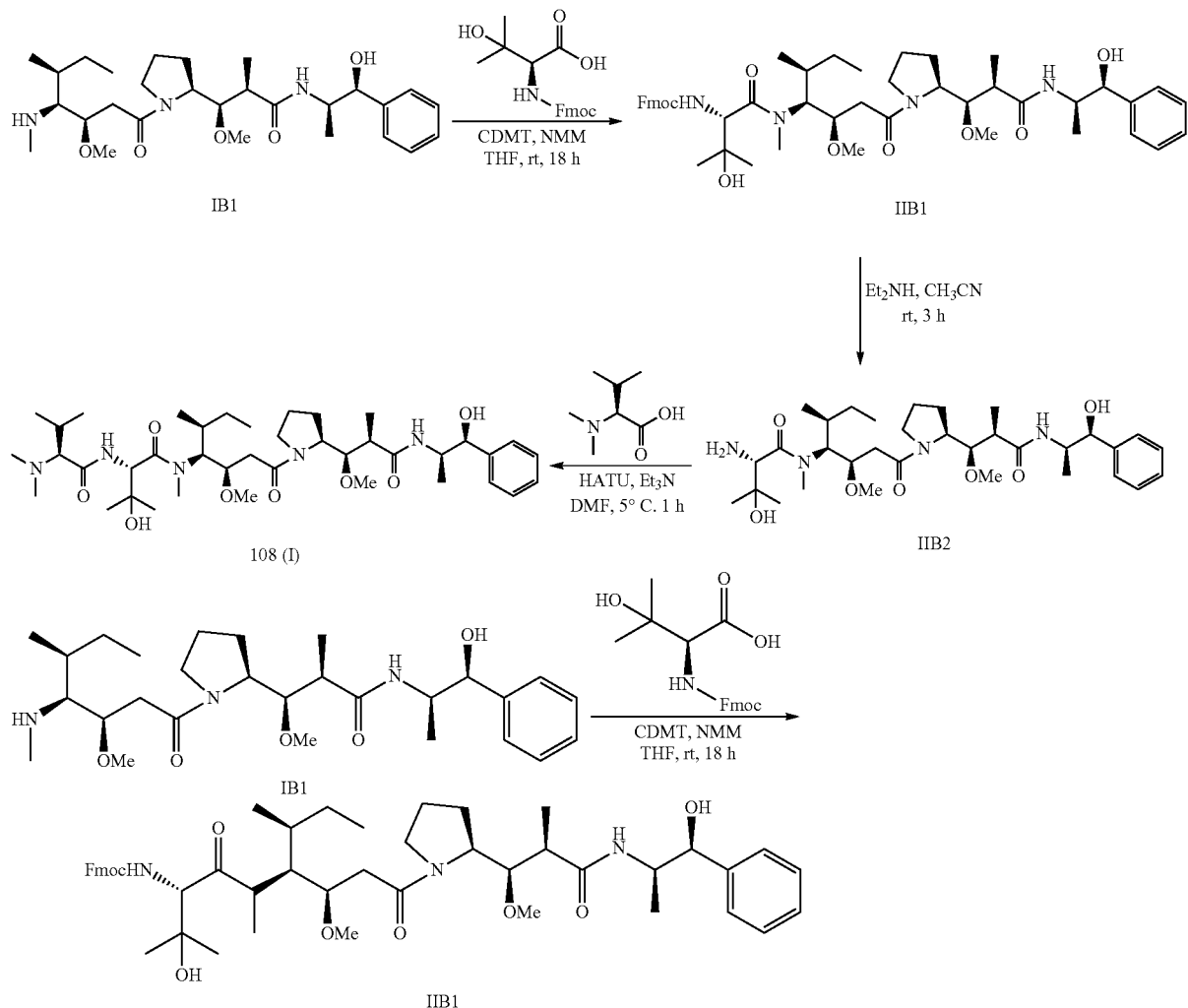

A reaction chamber equipped with magnetic stirbar was charged with IB1 (0.1 mmol), Fmoc-(S)-2-amino-3-hydroxy-3-methylbutanoic acid (0.2 mmol, 2.0 equiv.), and CDMT (2-chloro-4,6-dimethoxy-1,3,5-triazine, 0.2 mmol, 2.0 equiv.). The reaction chamber was flushed with Ar and the materials were dissolved in anhydrous THF (0.05 M) followed by slow addition of N-methylmorpholine (0.35 mmol, 3.5 equiv.) over 2 min. The pale yellow solution was allowed to stir at rt under Ar for 18 h. Subsequently, the crude mixture was loaded onto HP20ss (2 g), concentrated, and purified via Combiflash Rf (C18 15.5 g, 30 ml/min, $CH_3CN/H_2O$ linear gradient from 35-100% $CH_3CN$ over 12 min ramp). The desired product was isolated as a colorless oil (50% yield).

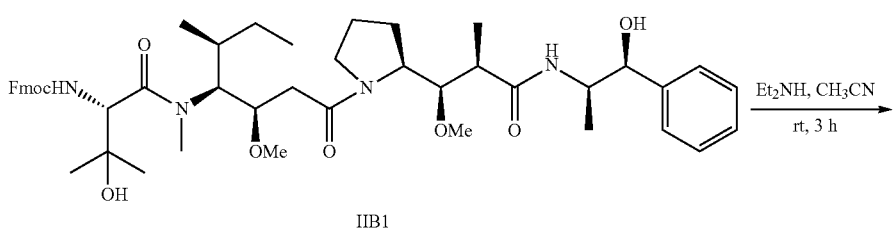

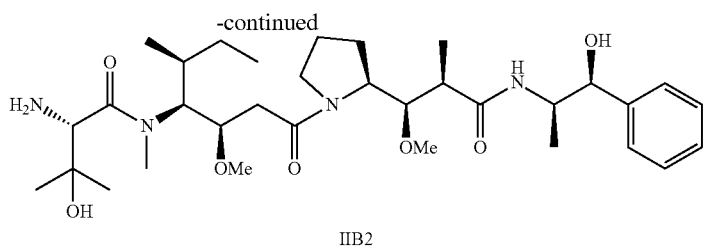

IIB2

A reaction chamber equipped with magnetic stirbar was charged with Fmoc-tetrapeptide (IIB1, 0.05 mmol). The material was dissolved in CH$_3$CN (0.01 M) followed by diethylamine (1.25 mmol, 25 equiv.) addition at rt and the resulting mixture was allowed to stir for 3 h. The mixture was extracted with pentane (3×3 mL) and concentrated to yield crude material as oil. The crude material was subjected to next step without further purification (70% yield).

HP20ss (2 g) and purified via CombiFlash Rf (C18 5.5 g, 18 mL/min, CH$_3$CN/H$_2$O linear gradient from 30-100% CH$_3$CN over 14 min ramp). The desired products were isolated as amorphous solids (80-90% yields). Observed ESI HRMS for compound 108: m/z 748.5263 [M+H]$^+$.

A reaction chamber equipped with magnetic stirbar was charged with Fmoc-pentapeptide II or III (0.05 mmol). The material was dissolved in CH$_3$CN (0.01 M) followed by

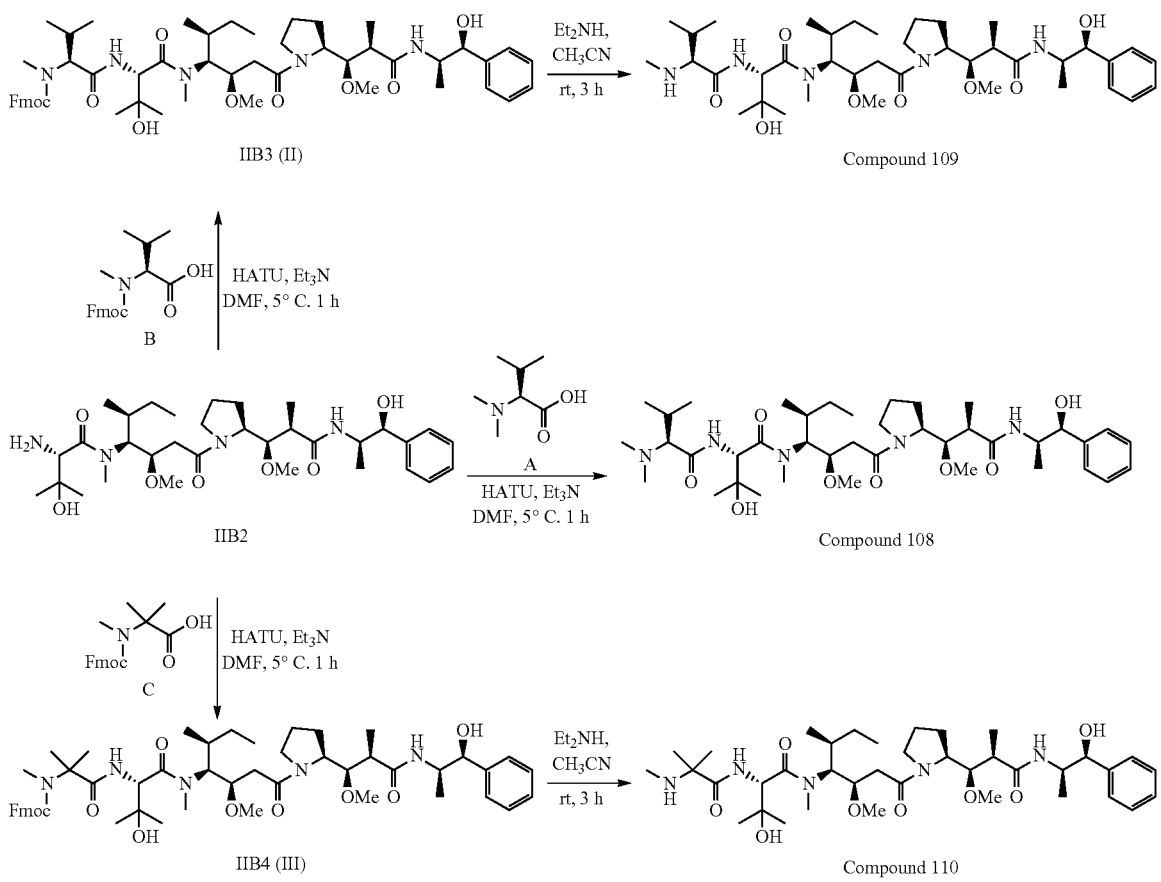

A reaction chamber equipped with magnetic stirbar was charged with free base tetrapeptide (IIB2, 0.05 mmol) and either A, B, or C amino acids (0.1 mmol, 2 equiv.). The materials were dissolved in anhydrous DMF (0.05 M) and cooled in an ice bath (~5° C.) under Ar followed by triethylamine (0.11 mmol, 2.2 equiv.) addition and the resulting mixture was allowed to stir for 5 min at 5° C. A solution of HATU (0.075 mmol, 1.5 equiv.) in anhydrous DMF (0.25 M) was slowly added into mixture at 5° C. The resulting mixture was allowed to stir in an ice bath for additional 45 min. The mixture was then loaded onto diethylamine (1.25 mmol, 25 equiv.) addition at rt and the resulting mixture was allowed to stir for 3 h. The mixture was extracted with pentane (3×3 mL) and concentrated to yield crude material as oil. The solution was then loaded onto HP20ss (2 g) and purified using CombiFlash Rf (C18Aq 5.5 g, 18 mL/min, CH$_3$CN/H$_2$O linear gradient from 0-50% CH$_3$CN over 12 min ramp). The desired product was isolated as a colorless oil (85-90% yields). Observed ESI HRMS for Compound 109: m/z 734.5100 [M+H]+; Compound 110: m/z 720.4948 [M+H]$^+$ Synthesis of Compound 111
Scheme 1-A3:
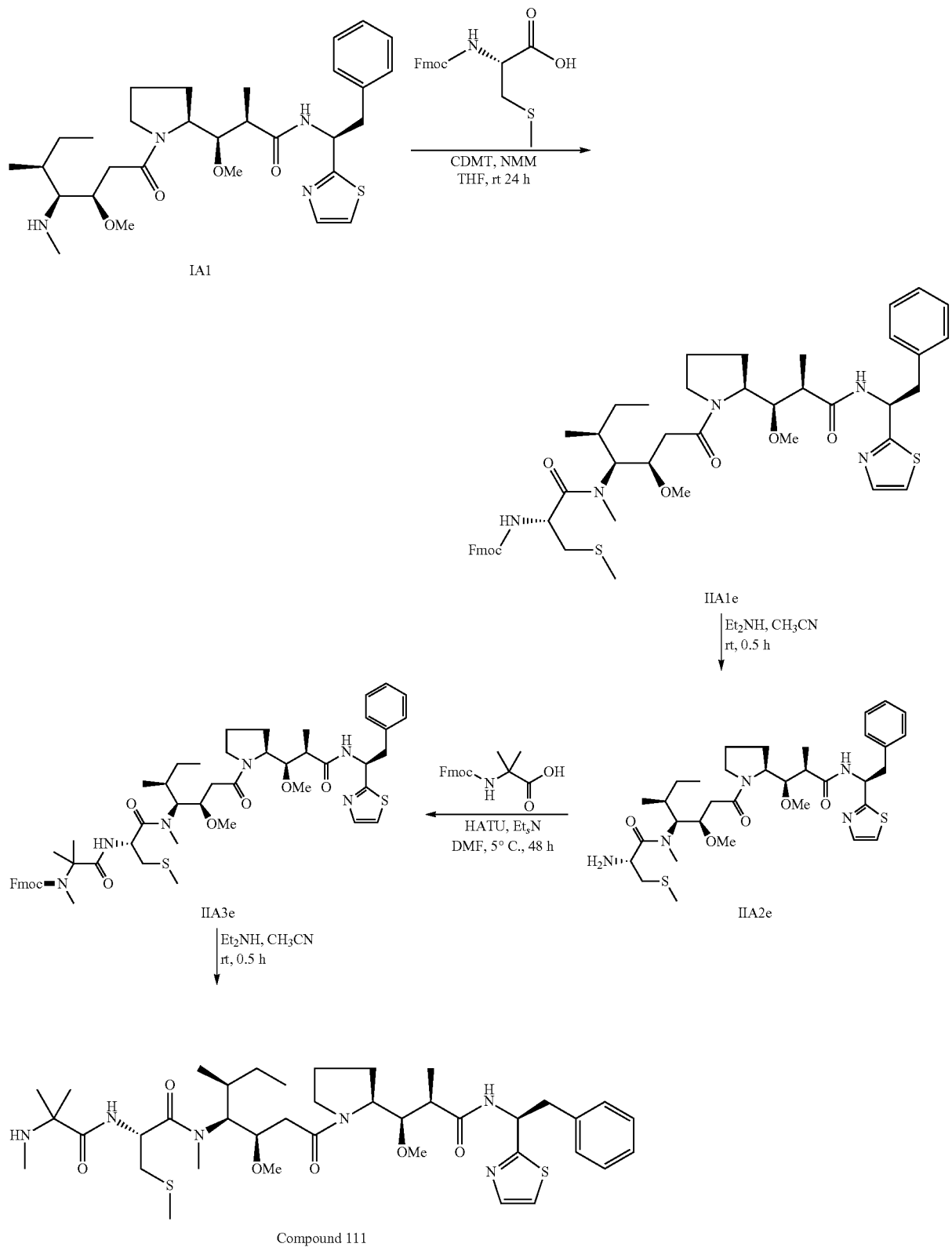
Compound 111

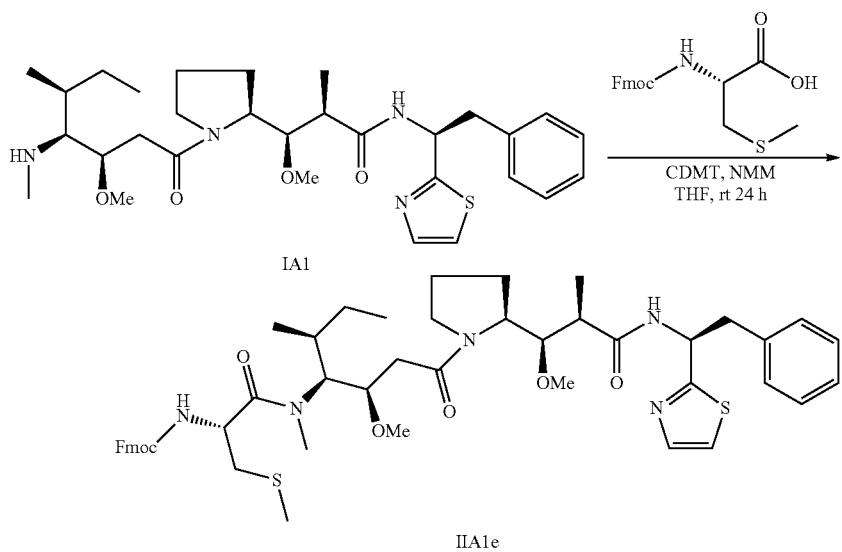

A reaction chamber equipped with magnetic stirbar was charged with IA1 (10 mg, 0.018 mmol), S-methyl-L-cysteine (13 mg, 0.036 mmol, 2.0 equiv.), and CDMT (2-chloro-4,6-dimethoxy-1,3,5-triazine, 6.28 mg, 0.036 mmol, 2.0 equiv.). The reaction chamber was flushed with Ar and the materials were dissolved in anhydrous THF (360 μL, 0.05 M) followed by slow addition of N-methylmorpholine (6.89 μL, 0.063 mmol, 3.5 equiv.) over 2 min. The pale yellow solution was allowed to stir at rt under Ar for 24 h. Subsequently, the crude mixture was concentrated, and purified via CombiFlash Rf (C18Aq 30 g, 35 mL/min, $CH_3CN/H_2O$ linear gradient from 0-100% $CH_3CN$ over 14 min ramp). The desired product, IIA1e, was isolated as a white powder (9.5 mg, 0.014 mmol, 79%). Observed ESI HRMS m/z 898.4204 $[M+H]^+$,

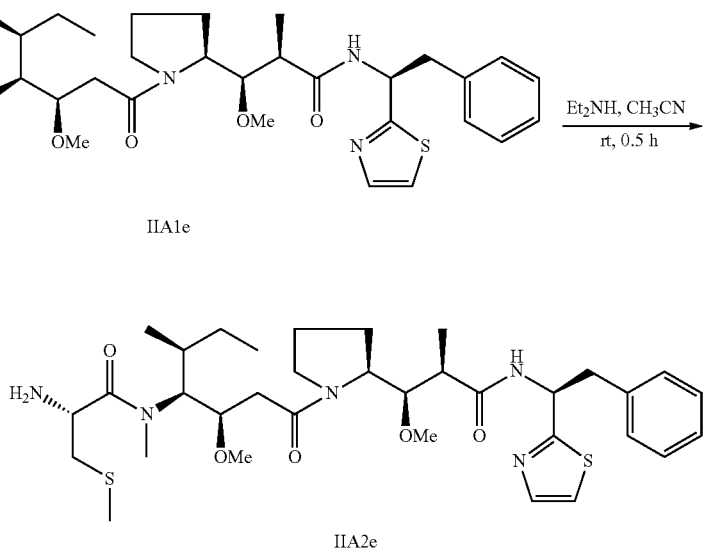

A reaction chamber equipped with magnetic stirbar was charged with Fmoc-tetrapeptide, (IIA1e, 9.5 mg, 0.0106 mmol). The material was dissolved in $CH_3CN$ (1 mL) followed by diethylamine (0.4 mL, 3.83 mmol, 362 equiv.) addition at rt and the resulting mixture was allowed to stir for 0.5 h. The crude reaction was concentrated, and purified via CombiFlash Rf (C18Aq 30 g, 35 mL/min, $CH_3CN/H_2O$ linear gradient from 0-100% $CH_3CN$ over 12 min ramp). The desired product (IIA2e) was isolated as a white solid (7 mg, 0.0104 mmol, 98%). Observed ESI HRMS m/z 676.3533 $[M+H]^+$.

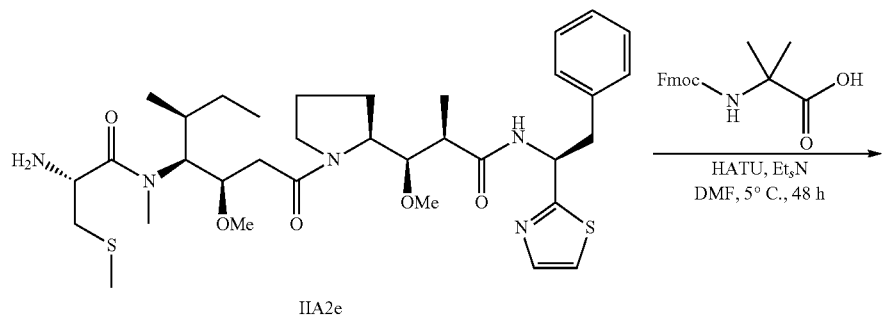

IIA2e

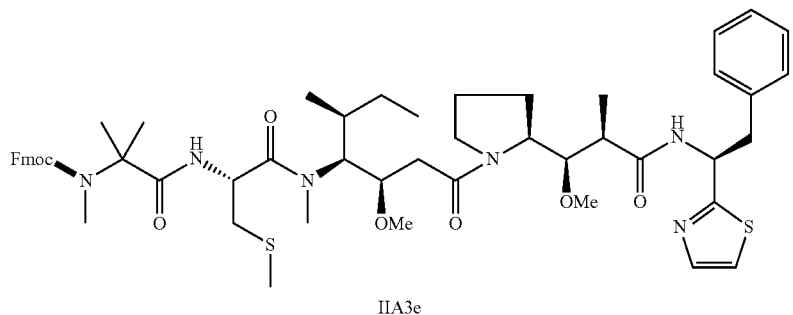

IIA3e

A reaction chamber equipped with magnetic stirbar was charged with free base tetrapeptide (IIA2e, 7 mg, 0.0104 mmol) and Fmoc-2-methylamino isobutyric acid (7.03 mg, 0.021 mol, 2 equiv.). The materials were dissolved in anhydrous DMF (0.7 mL) and cooled in an ice bath (~5° C.) under Ar followed by triethylamine (3.18 µL, 0.023 mmol, 2.2 equiv.) addition and the resulting mixture was allowed to stir for 5 min at 5° C. A solution of HATU (5.91 mg, 0.016 mmol, 1.5 equiv.) in anhydrous DMF (0.5 mL) was slowly added into the mixture at 5° C. The mixture turned pale yellow and was allowed to stir in an ice bath for additional 45 min. The mixture was concentrated and purified via CombiFlash Rf (C18Aq 30 g, 35 mL/min, CH$_3$CN/H$_2$O linear gradient from 0-100% CH$_3$CN over 15 minutes). The desired product (IIA3e) was isolated as an amorphous solid (11 mg, 0.011 mmol, 107%). Observed ESI HRMS m/z 997.4882 [M+H]$^+$.

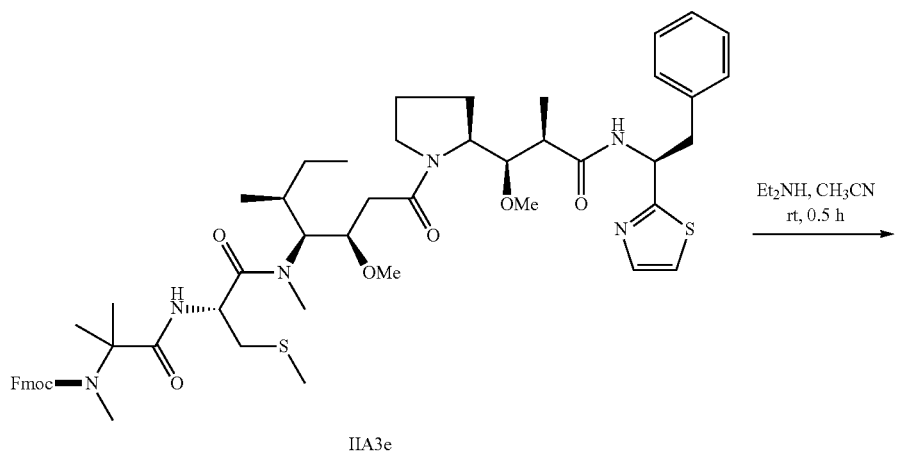

IIA3e

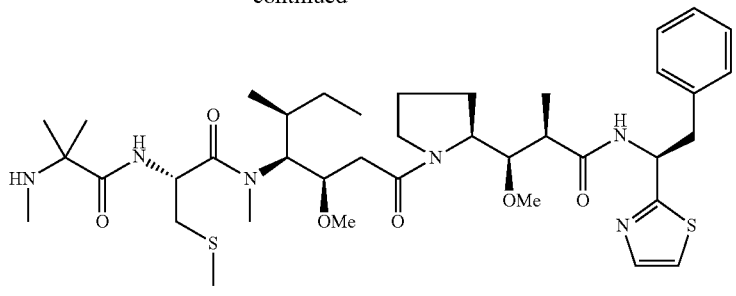

Compound 111

A reaction chamber equipped with magnetic stirbar was charged with Fmoc-pentapeptide (IIA3e, 11 mg, 0.011 mmol). The material was dissolved in CH$_3$CN (1.0 mL) and purged with Ar. Diethylamine (0.4 mL, 3.83 mmol, 347 equiv.) was then added at rt and the resulting mixture allowed to stir for 0.5 h. The mixture was concentrated and purified using CombiFlash Rf (C18Aq 30 g, 35 mL/min, CH$_3$CN/H$_2$O linear gradient from 0-100% CH$_3$CN over 15 minutes). The desired product, Compound 111, was isolated as a colorless oil (3.03 mg, 3.91 μmol, 35%). Observed ESI HRMS m/z 388.218 [M+2H]$^{2+}$.

Synthesis of Compound 112

Scheme I-A4:

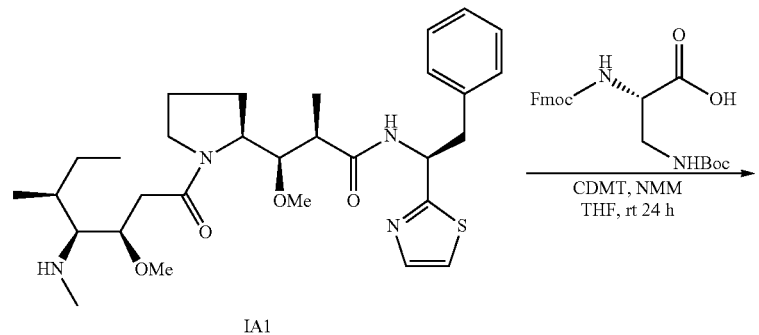

IA1

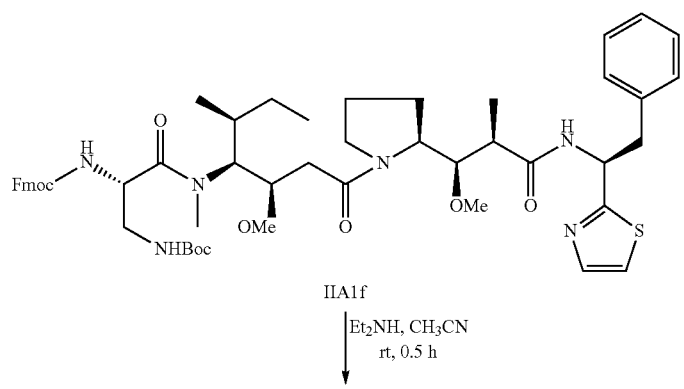

IIA1f

Et$_2$NH, CH$_3$CN
rt, 0.5 h

-continued
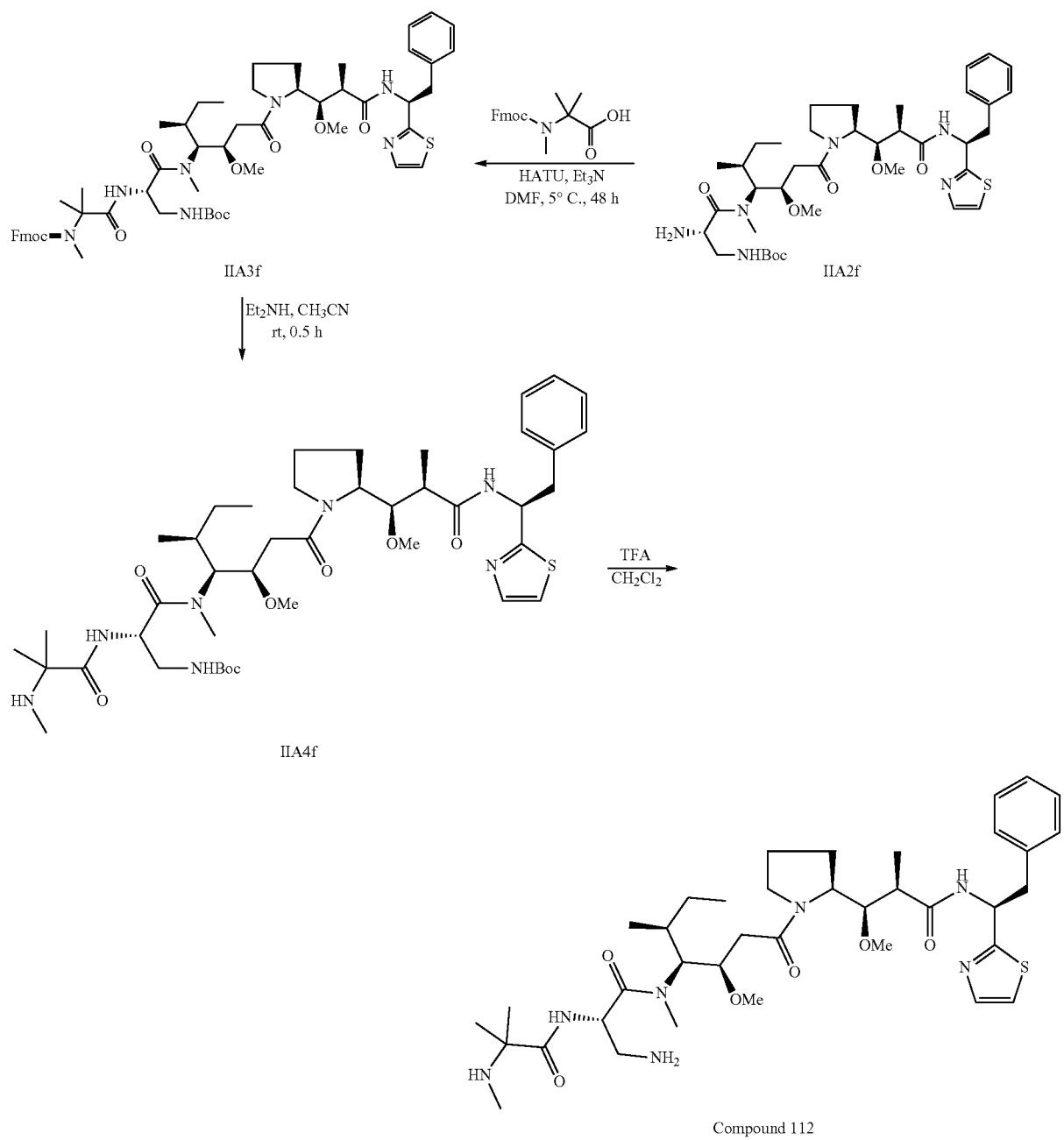
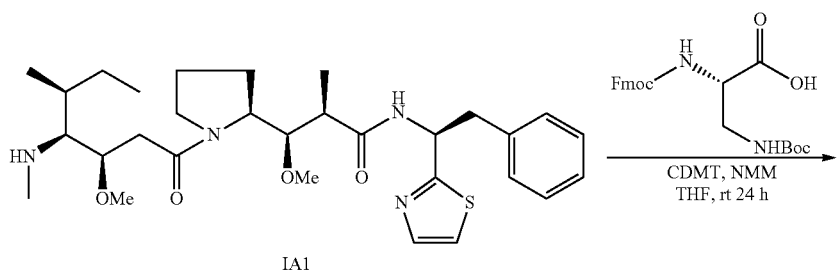

-continued

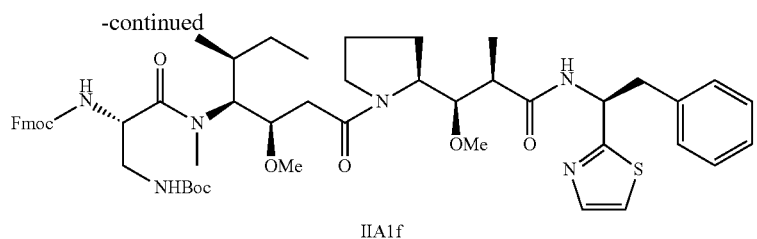

IIA1f

A reaction chamber equipped with magnetic stirbar was charged with IA1 (10 mg, 0.018 mmol), Fmoc-Dap(Boc)-OH (15 mg, 0.036 mmol, 2.0 equiv.), and CDMT (2-chloro-4,6-dimethoxy-1,3,5-triazine, 6.28 mg, 0.036 mmol, 2.0 equiv.). The reaction chamber was flushed with Ar and the materials were dissolved in anhydrous THF (180 μL, 0.05 M) followed by slow addition of N-methylmorpholine (6.89 μL, 0.063 mmol, 3.5 equiv.) over 2 min. The pale yellow solution was allowed to stir at rt under Ar for 24 h. Upon completion the crude reaction was concentrated, and purified via CombiFlash Rf (C18Aq 30 g, 35 mL/min, CH$_3$CN/H$_2$O linear gradient from 0-100% CH$_3$CN over 15 min ramp). The desired product was isolated as a white powder (9 mg, 9.30 μmol, 52%). Observed ESI HRMS m/z 967.4962 [M+H]$^+$.

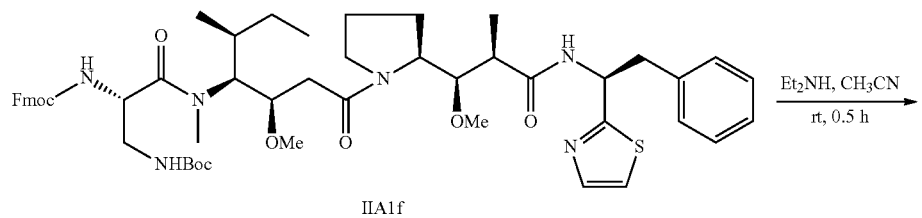

IIA1f

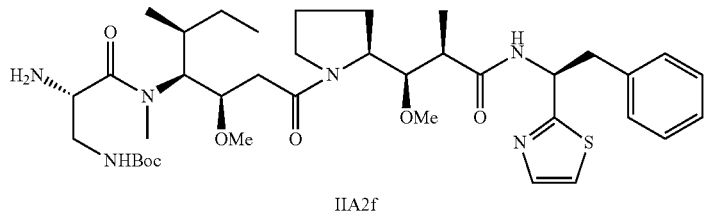

IIA2f

To a reaction chamber equipped with magnetic stirbar was charged with Fmoc-tetrapeptide (IIA1f, 9 mg, 9.30 μmol). The material was dissolved in CH$_3$CN (1 mL) followed by diethylamine (0.4 mL, 3.81 mmol, 410 equiv.) addition at rt and reaction mixture was allowed to stir for 0.5 h. The crude reaction was concentrated, and purified via CombiFlash Rf (C18Aq 30 g, 30 mL/min, CH$_3$CN/H$_2$O linear gradient from 0-100% CH$_3$CN over 12 min ramp). The desired product was isolated as a white powder (8 mg, 9.30 μmol, 115%). Observed ESI HRMS m/z 745.4278 [M+H]$^+$.

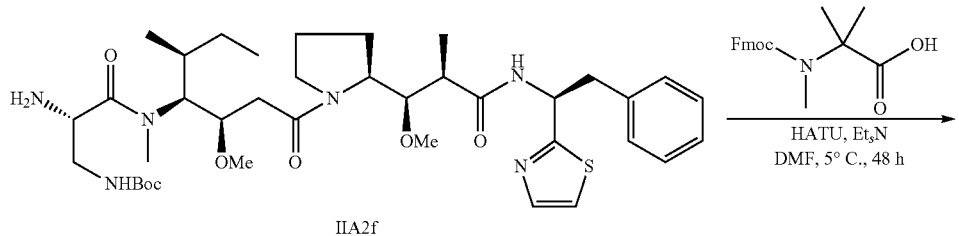

IIA2f

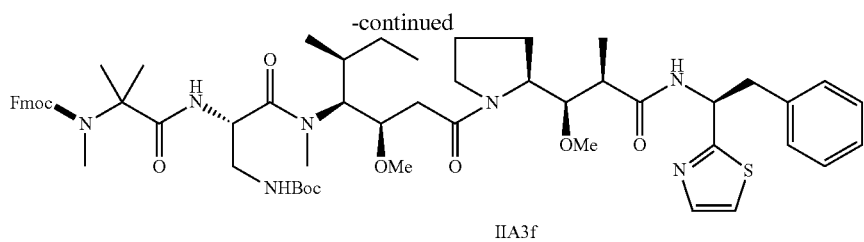

IIA3f

A reaction chamber equipped with magnetic stirbar was charged with free base tetrapeptide (IIA2f, 8 mg, 0.0107 mmol) and Fmoc-2-methylamino isobutyric acid (7.29 mg, 0.0201 mol, 2 equiv.). The materials were dissolved in anhydrous DMF (0.7 mL) and cooled in an ice bath (~5° C.) under Ar followed by triethylamine (3.29 µL, 0.024 mmol, 2.2 equiv.) addition and the reaction was allowed to stir for 5 min at 5° C. A solution of HATU (6.12 mg, 0.016 mmol, 1.5 equiv.) in anhydrous DMF (0.5 mL) was slowly added into reaction mixture at 5° C. The reaction turned pale yellow and was allowed to stir in an ice bath for additional 45 min. The reaction solution was concentrated and purified via CombiFlash Rf (C18Aq 30 g, 35 mL/min, CH$_3$CN/H$_2$O linear gradient from 0-100% CH$_3$CN over 15 minutes). The desired product was isolated as a white powder (3.8 mg, 3.56 µmol, 33%). Observed ESI HRMS m/z 1066.5639 [M+H]$^+$.

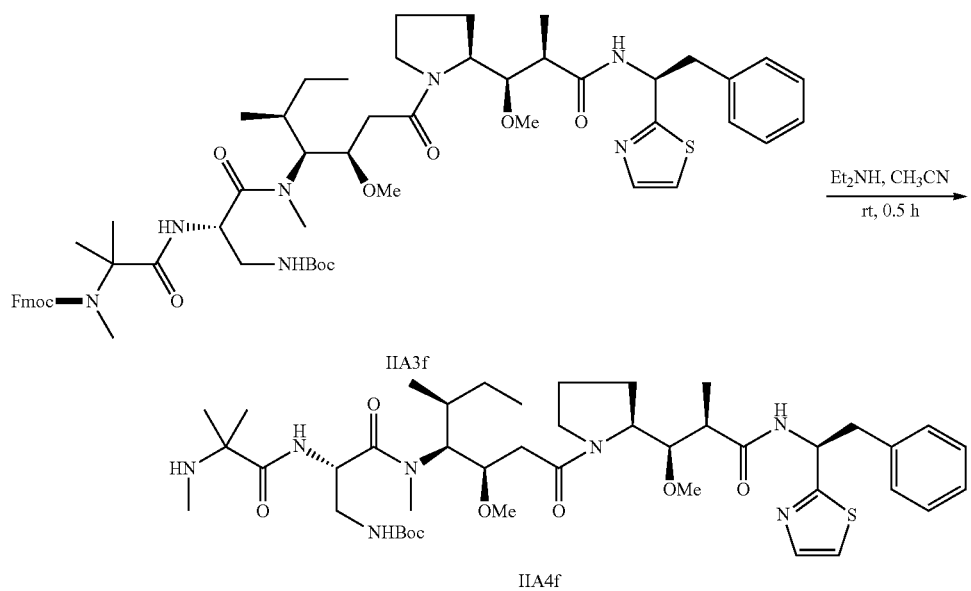

IIA4f

A reaction chamber equipped with magnetic stirbar was charged with Fmoc-pentapeptide (IIA3f, 3.8 mg, 3.56 µmol). The material was dissolved in CH$_3$CN (1.0 mL) and purged with Ar. Diethylamine (0.406 mL, 3.88 mmol, 1090 eq) was then added at rt and allowed to stir for 0.5 h. The solution was concentrated and purified using CombiFlash Rf (C18Aq 30 g, 35 mL/min, CH$_3$CN/H$_2$O linear gradient from 0-100% CH$_3$CN over 15 minutes). The desired product was isolated as white powder (2.1 mg, 2.488 µmol, 70%). Observed ESI HRMS m/z 422.7568 [M+2H]$^{2+}$.

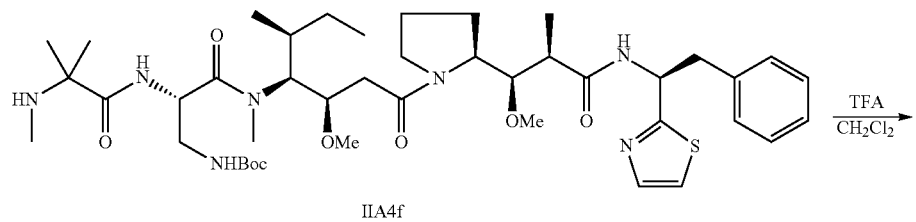

IIA4f

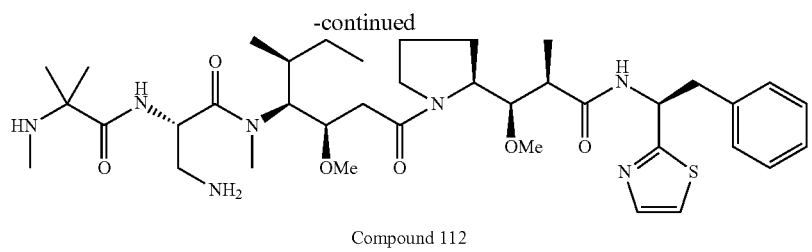

Compound 112

A reaction chamber equipped with a magnetic stirbar was charged with Boc-pentapeptide (IIA4f, 2.1 mg, 2.488 μmol). The material was dissolved in CH$_2$Cl$_2$ (1 mL) followed by the addition of trifluoroacetic acid (0.180 mL, 2.339 mmol, 940 eq) at 0° C. and allowed to stir at 0° C. for 0.5 h, then warmed to rt and allowed to stir for an additional 0.5 h. The solution was concentrated and purified using CombiFlash Rf (C18Aq 30 g, 35 mL/min, CH$_3$CN/H$_2$O linear gradient from 0-100% CH$_3$CN over 15 minutes). The desired product was isolated as a white powder (350 μg, 2.488 μmol, 20%). Observed ESI HRMS m/z 744.4502 [M+H]$^+$.

Synthesis of Compound 113

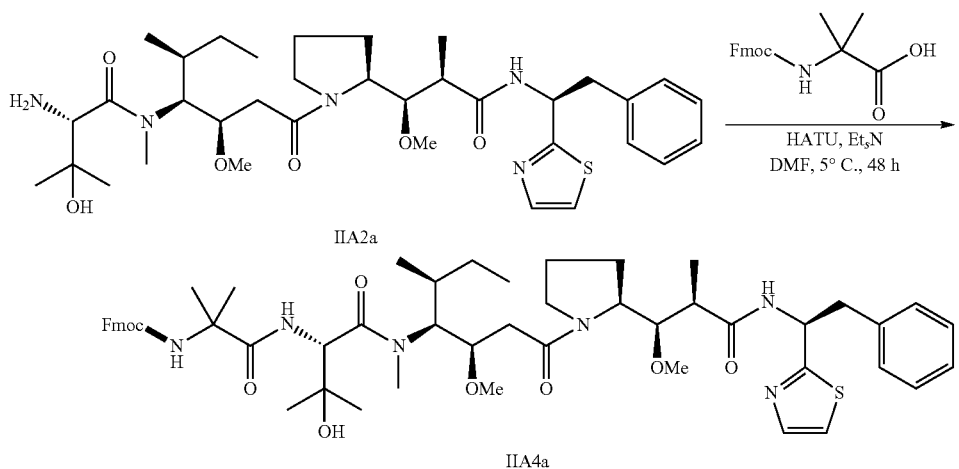

A reaction chamber equipped with magnetic stirbar was charged with tetrapeptide (IIA2a, 3 mg, 4.45 μmol) and Fmoc-2-methylamino isobutyric acid (2.90 mg, 8.90 μmol, 2 equiv.). The materials were dissolved in anhydrous DMF (0.7 mL) and cooled in an ice bath (~5° C.) under Ar followed by triethylamine (1.365 μL, 9.79 μmol, 2.2 equiv.) addition and the resulting mixture was allowed to stir for 5 min at 5° C. A solution of HATU (2.54 mg, 6.68 μmol, 1.5 equiv.) in anhydrous DMF (0.5 mL) was slowly added into the mixture at 5° C. The mixture turned pale yellow and was allowed to stir in an ice bath for additional 45 min. The mixture was concentrated and purified via CombiFlash Rf (C18Aq 30 g, 35 mL/min, CH$_3$CN/H$_2$O linear gradient from 0-100% CH$_3$CN over 15 minutes). The desired product (IIA4a) was isolated as a white powder (2.29 mg, 0.06 mmol, 66%). Observed ESI HRMS m/z m/z=981.5106 [M+H]$^+$.

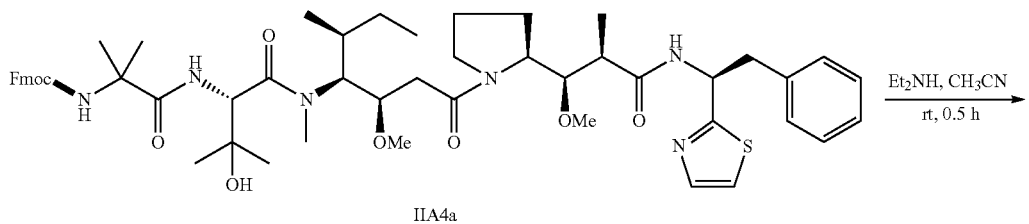

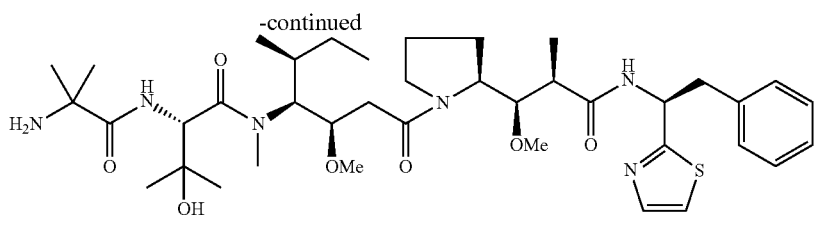

Compound 113

A reaction chamber equipped with magnetic stirbar was charged with Fmoc-pentapeptide (IIA4a, 2.9 mg, 2.96 μmol). The material was dissolved in CH$_3$CN (1.0 mL) and purged with Ar. Diethylamine (0.401 mL, 3.84 mmol, 1300 eq) was then added at rt and allowed to stir for 0.5 h. The solution was concentrated and purified using CombiFlash Rf (C18Aq 30 g, 35 mL/min, CH$_3$CN/H$_2$O linear gradient from 0-100% CH$_3$CN over 15 minutes). The desired product was isolated as a white powder (1 mg, 1.317 μmol, 45%). Observed ESI HRMS m/z m/z=380.2291 [M+2H]$^{2+}$.

Synthesis of Compound 114

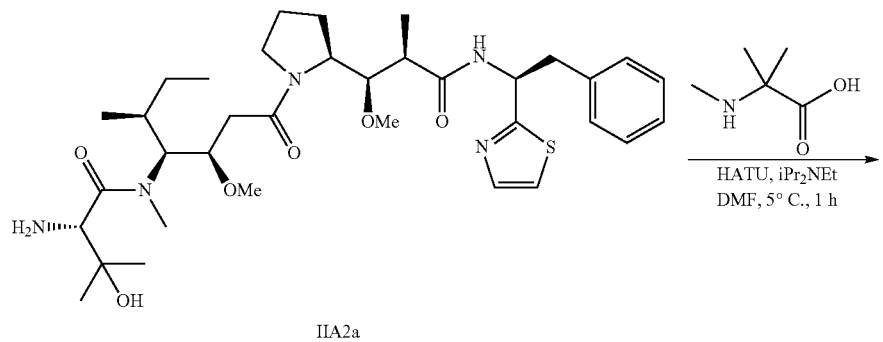

IIA2a

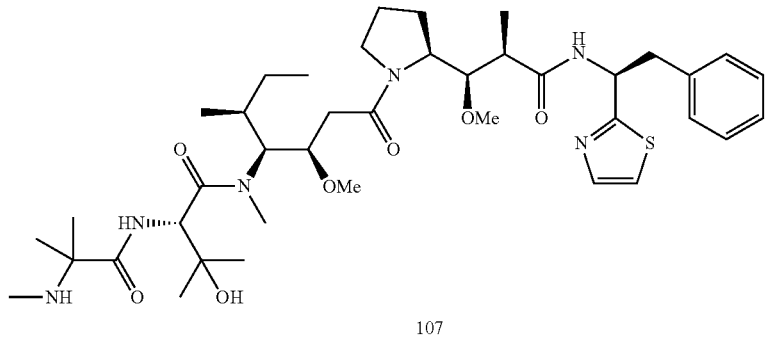

107

+

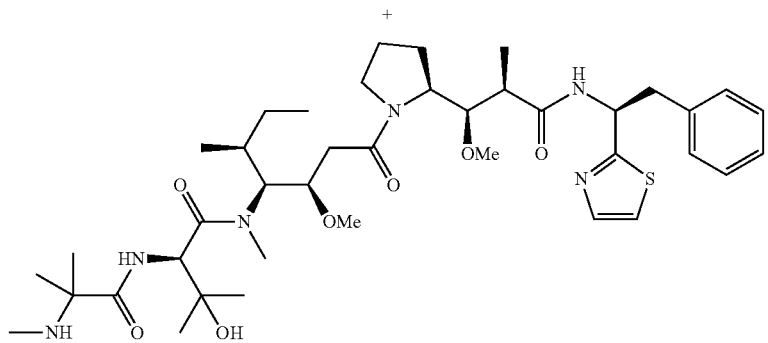

114

A reaction chamber equipped with magnetic stirbar was charged with free base tetrapeptide IIA2a (75 mg, 0.111 mmol) and 2-methylaminoisobutyric acid (13 mg, 0.111 mmol, 1 equiv.). The materials were dissolved in anhydrous DMF (1.5 mL) and cooled in an ice bath (~5° C.) under Ar followed by addition of N,N-diisopropylamine (78 µL, 0.445 mmol, 4 equiv.) and HATU (63 mg, 0.167 mmol, 1.5 equiv.). The resulting mixture was allowed to stir for 90 min at 5° C. The mixture was then loaded onto HP20ss (4 g) and purified via CombiFlash Rf (C18 15.5 g, 30 mL/min, $CH_3CN/H_2O$ linear gradient from 15-100% $CH_3CN$ over 14 minutes). Compounds 107 (13 mg, 0.017 mmol, 15%) and 114 (11 mg, 0.014 mmol, 13%) were each isolated as glassy amorphous solids. Observed ESI HRMS for compound 114: m/z 773.4696 [M+H]+; Compound 114 exists as two conformers in a 3:2 ratio in CD3OD solvent; the NMR chemical shifts for the major 114 conformer are listed here. $^1$H NMR (CD$_3$OD, 600 MHz): δ 7.79 (d, J=3.2 Hz, 1H), 7.53 (d, J=3.2 Hz, 1H), 7.31 (d, J=7.3 Hz, 2H), 7.25 (t, J=7.3 Hz, 2H), 7.21 (d, J=7.3 Hz, 1H), 5.66 (dd, J=4.1, 11.4 Hz, 1H), 5.02 (s, 1H), 4.15 (m, 1H), 3.67 (m, 1H), 3.57 (m, 1H), 3.51 (dd, J=4.5, 14 Hz, 1H), 3.42 (d, J=10.8 Hz, 1H), 3.38 (s, 3H), 3.35 (s, 3H), 3.33 (m, 1H), 3.20 (m, 1H), 3.20 (s, 3H), 3.04 (m, 1H), 2.59 (s, 3H), 2.48 (m, 1H), 2.38 (m, 1H), 2.29 (m, 1H), 1.89 (m, 1H), 1.88 (m, 1H), 1.71 (m, 1H), 1.62 (s, 3H), 1.60 (m, 1H), 1.55 (s, 3H), 1.40 (m, 1H), 1.39 (s, 3H), 1.37 (m, 1H), 1.26 (s, 3H), 1.16 (d, J=6.6 Hz, 3H), 1.04 (m, 1H), 1.01 (d, J=7.3, 3H), 0.87 (t, J=7.4, 3H).

Example 2

General Procedure B—Synthesis of Reduced Antibody (Ab(r))

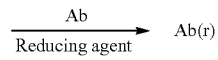

Scheme II-A

Purified antibody (Ab) may be buffer exchanged into a buffer such as PBS (pH 7.4) and then further diluted. Purified antibody (Ab) may be diluted to a final concentration, for example, 5 mg/mL in buffer and warmed in a heat block. A stock solution of reducing agent such as TCEP (tris(2-carboxyethyl)phosphine) may be added to the antibody buffer solution to provide partially reduced antibody (Ab(r)).

General Procedure C—Synthesis of Antibody Drug Conjugate (ADC)

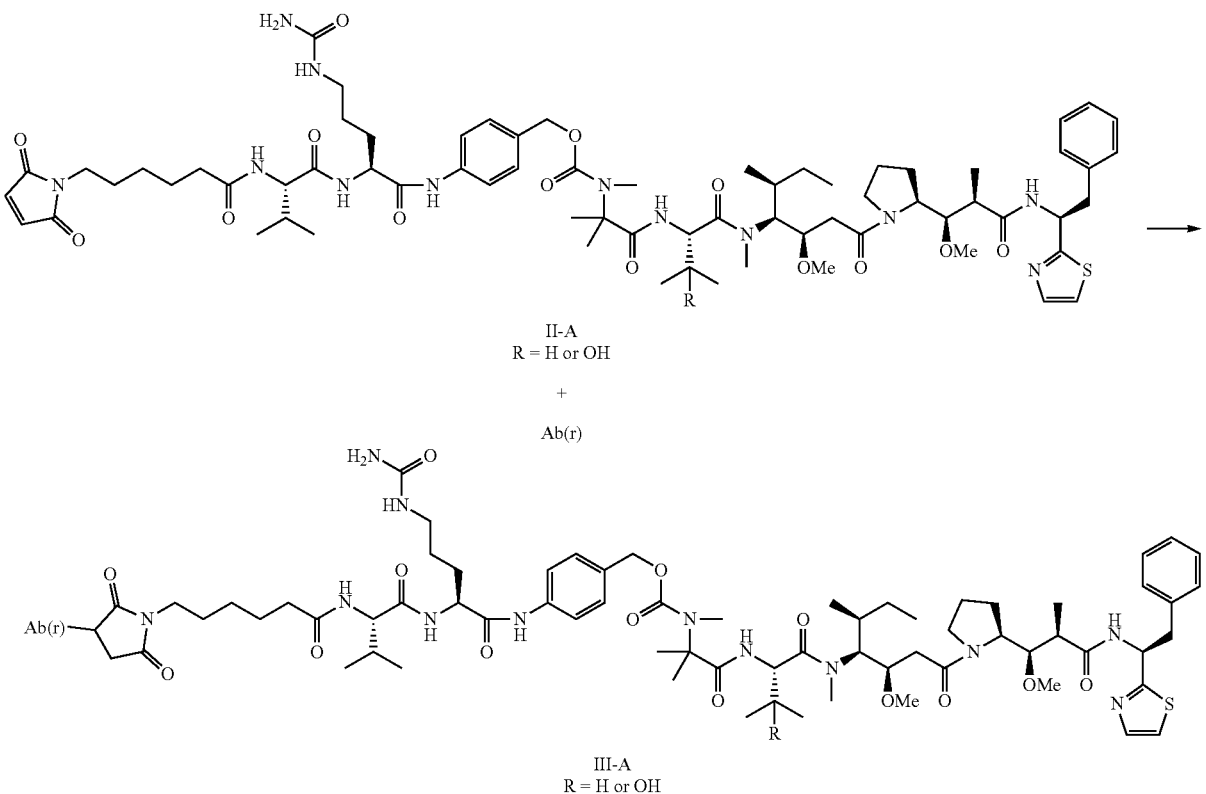

A stock solution of compound II-A in a solvent may be added to the partially reduced antibody (Ab(r)) and allowed to mix for a period of time to provide antibody drug conjugate compound III-A. After a period of time, the mixture may be buffer exchanged and stored at reduced temperature until needed. The drug to antibody ration (DAR) may be measured by Hydrophobic Interaction Chromatography (HIC) and aggregation may be measured by Size Exclusion Chromatography (SEC).

Example 2A: Synthesis of Conjugate 107-L1-Ab1 and MMAD-L1-Ab1

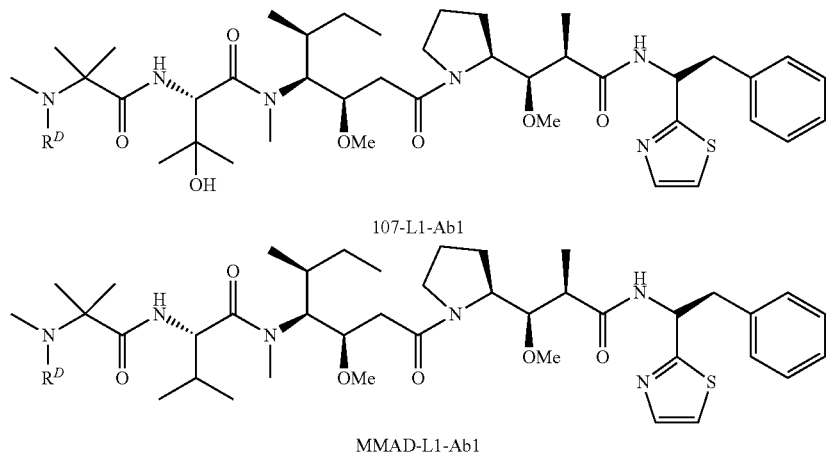

107-L1-Ab1

MMAD-L1-Ab1

Where $R^D$ is Ab1-Mc-Val-Cit-PAB-C(O)—; Ab1=Antibody

The drug-Linker 107-L1 and MMAD-L1, which corresponds to compounds 107 and MMAD respectively, where L1 is Mc-Val-Cit-PAB-, were synthesized using protocols similar to methods described previously (Ref: Doronina, S. O. et al., Bioconjugate Chem. 2008, 19 (10), 1960-1963).

The antibody-drug conjugates 107-L1-Ab1 and MMAD-L1-Ab1 which correspond to drug-likers 107-L1 and MMAD-L1 respectively, wherein Ab1 is undisclosed antibody, were synthesized using protocols similar to methods described previously (Ref: Doronina, S. O. et al, Bioconjugate Chem. 2008, 19 (10), 1960-1963). Briefly, the purified antibody, Ab1 was buffer exchanged into PBS (pH 7.4). The antibody was diluted to a final concentration of 5 mg/mL in PBS and warmed to 37° C. in a heat block. A stock solution of TCEP (tris(2-carboxyethyl)phosphine, 50 mM) was freshly prepared in water, and 2.5 molar equivalent (relative to the antibody concentration) was added. After 2 h, the partially reduced antibody was removed from the heat block and cooled to room temperature. A stock solution of drug-linker 107-L1 or MMAD-L1 (2 mM in DMSO) was freshly prepared, and 2-5 molar equivalent was added to the antibody. After 1 h, the reaction mixture was buffer exchanged into PBS using PD10 spin columns to remove small MW reagents and stored at 4° C. until needed. The drug to antibody ratio (DAR) was measured by Hydrophobic Interaction Chromatography (HIC) and aggregation was measured by Size Exclusion Chromatography (SEC).

Example 3. Inhibitory Response of Test Compounds Against MES-SA and MES-SA/Dx Cells MES-SA (human uterine sarcoma) cells were seeded in a clear polystyrene 96-well microculture plate (Corning® Costar® 96-well flat bottom plate, Cat. #3997) in a total volume of 90 µL/well. After 24 hours of incubation in a humidified incubator at 37° C. with 5% $CO_2$ and 95% air, 10 µL of 10×, serially diluted test agents in growth medium were added to each well (10 pt dose response curve, highest concentration 10 µM of test agent). After 72 hours of culture in a humidified incubator at 37° C., in an atmosphere of 5% $CO_2$ and 95% air, the plated cells and Cell Titer-Glo® (Promega G7571) reagents were brought to room temperature to equilibrate for 30 minutes. 100 µL of Cell Titer-Glo® reagent was added to each well. The plate was shaken for two minutes and then left to equilibrate for ten minutes. The media/Cell Titer-Glo® reagent was transferred to a white polystyrene 96-well microculture plate (Corning® Costar® 96-well flat bottom plate, Cat. #3917) before reading luminescence on a Tecan GENios microplate reader.

MES-SA/Dx (multidrug-resistant human uterine sarcoma) cells are seeded in a clear polystyrene 96-well microculture plate in a total volume of 90 µL/well. After 24 hours of incubation in a humidified incubator at 37° C. with 5% $CO_2$ and 95% air, 10 µL of 10×, serially diluted test agents in growth medium are added to each well. After 72 hours of culture in a humidified incubator at 37° C., in an atmosphere of 5% $CO_2$ and 95% air, the plated cells and Cell Titer-Glo® (Promega G7571) reagents are brought to room temperature to equilibrate for 30 minutes. 100 µL of Cell Titer-Glo® reagent are added to each well. The plate is shaken for two minutes and then left to equilibrate for ten minutes. The media/Cell Titer-Glo® reagent is transferred to a polystyrene 96-well microculture plate before reading luminescence on a Tecan GENios microplate reader.

Percent inhibition of cell growth is calculated relative to untreated control wells. The $IC_{50}$ value for the test agents is determined using Prism 6.05 by curve-fitting of the data using the following four parameter-logistic equation:

$$Y = \frac{\text{Top} - \text{Bottom}}{1 + (X/IC_{50})^n} + \text{Bottom},$$

where Top is the maximal % of control absorbance, Bottom is the minimal % of control absorbance at the highest agent concentration, Y is the % of control absorbance, X is the agent concentration, $IC_{50}$ is the concentration of agent that inhibits cell growth by 50% compared to the control cells, and n is the slope of the curve. Data for compounds 101, 109 and 110 is shown in Table 3.

TABLE 3

| Compound | MES SA IC$_{50}$ in nM | MES DX IC$_{50}$ in nM |
| --- | --- | --- |
| 101 | 0.03496 | 6.373 |
| 109 | 14.9 | NT |
| 110 | 4.185 | NT |

Example 4: Inhibitory Response of Test Compounds Against BT-474 Cells

BT-474 human mammary gland ductal carcinoma cells were seeded in a clear polystyrene 96-well microculture plate (Corning® Costar® 96-well flat bottom plate, Cat. #3997) in a total volume of 90 µL/well. After 24 hours of incubation in a humidified incubator at 37° C. with 5% CO$_2$ and 95% air, 10 µL of 10×, serially diluted test agents in growth medium were added to each well (10 pt dose response curve, highest concentration 10 M of test agent). After 72 hours of culture in a humidified incubator at 37° C., in an atmosphere of 5% CO$_2$ and 95% air, the plated cells and Cell Titer-Glo® (Promega G7571) reagents were brought to room temperature to equilibrate for 30 minutes. 100 µL of Cell Titer-Glo® reagent was added to each well. The plate was shaken for two minutes and then left to equilibrate for ten minutes. The media/Cell Titer-Glo® reagent was transferred to a white polystyrene 96-well microculture plate (Corning® Costar® 96-well flat bottom plate, Cat. #3917) before reading luminescence on a Tecan GENios microplate reader.

Percent inhibition of cell growth was calculated relative to untreated control wells. The IC$_{50}$ value for the test agents was determined using Prism 6.05 by curve-fitting of the data using the following four parameter-logistic equation:

$$Y = \frac{Top - Bottom}{1 + (X/IC_{50})^n} + Bottom,$$

where Top is the maximal % of control absorbance, Bottom is the minimal % of control absorbance at the highest agent concentration, Y is the % of control absorbance, X is the agent concentration, IC$_{50}$ is the concentration of agent that inhibits cell growth by 50% compared to the control cells, and n is the slope of the curve.

Inhibitory response of test compounds against HCC1954 cells was determined using a method analogous to that used for BT-474 cells. IC$_{50}$ values for various test agents in HCC1954 and/or BT-474 cells are shown in Table 4.

TABLE 4

| Compound | BT-474 IC$_{50}$ in nM | HCC1954 IC$_{50}$ in nM |
| --- | --- | --- |
| 101 | 0.0022 | 0.004 |
| 104 | 0.364 | 0.435 |
| 105 | 8.554 | 7.966 |
| 106 | 2.369 | 1.137 |
| 107 | 0.064 | 0.030 |
| 108 | 0.140 | 0.460 |
| 109 | 26.10 | 10.92 |
| 110 | 9.088 | 2.924 |
| 114 | 0.0616 | 0.017 |
| 111 | 0.8634 | 0.06556 |
| 112 | NT | NT |
| 113 | 1.221 | 1.235 |

Example 5: Inhibitory Response of Test Conjugates Against 293T Cells 293T human embryonic kidney cells were seeded in a clear polystyrene 96-well microculture plate in a total volume of 90 µL/well. After 24 hours of incubation in a humidified incubator at 37° C. with 5% CO$_2$ and 95% air, 10 µL of 10×, serially diluted test agents (e.g., conjugates, such as compounds bound to an antibody via a linker) in growth medium were added to each well. After 72 hours of culture in a humidified incubator at 37° C., in an atmosphere of 5% CO$_2$ and 95% air, the plated cells and Cell Titer-Glo® (Promega G7571) reagents were brought to room temperature to equilibrate for 30 minutes. 100 µL of Cell Titer-Glo® reagent were added to each well. The plate was shaken for two minutes and then left to equilibrate for ten minutes. The media/Cell Titer-Glo® reagent was transferred to a polystyrene 96-well microculture plate before reading luminescence on a Tecan GENios microplate reader.

Percent inhibition of cell growth was calculated relative to untreated control wells. The IC$_{50}$ value for the test agents was determined using Prism 6.05 by curve-fitting of the data using the following four parameter-logistic equation:

$$Y = \frac{Top - Bottom}{1 + (X/IC_{50})^n} + Bottom,$$

where Top is the maximal % of control absorbance, Bottom is the minimal % of control absorbance at the highest agent concentration, Y is the % of control absorbance, X is the agent concentration, IC$_{50}$ is the concentration of agent that inhibits cell growth by 50% compared to the control cells, and n is the slope of the curve. Data for antibody-drug conjugates tested is shown in Table 5.

TABLE 5

| Test Agent | DAR | % Aggregate | MES-SA IC$_{50}$ (nM) | 293T IC$_{50}$ (nM) |
| --- | --- | --- | --- | --- |
| 107-L1-Ab1 | 3.8 | 2.4 | 3293 | 0.079 |
| MMAD-L1-Ab1 | 3.6 | 12.6 | NT | 0.012 |

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

While one or more embodiments of the present disclosure have been described, it will be understood by those of ordinary skill in the art that various changes in form and details may be made therein without departing from the spirit and scope of the present embodiments as defined by the following claims.

What is claimed is:

1. A compound having the structure of Formula I:

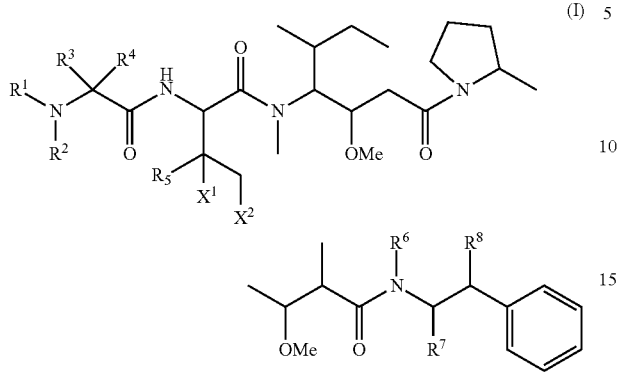

(I)

or pharmaceutically acceptable salts or solvates thereof, wherein:

$R^1$ is hydrogen;

$R^2$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^3$ is selected from the group consisting of optionally substituted $C_1$-$C_6$ alkyl, an optionally substituted hydroxyl, an optionally substituted $C_1$-$C_6$ alkoxy, an optionally substituted $C_3$-$C_7$ cycloalkyl, an optionally substituted aryl, and an optionally substituted heteroaryl;

$R^4$ is an optionally substituted $C_1$-$C_6$ alkyl;

$R^5$ is hydrogen, deuterium or an optionally substituted $C_1$-$C_6$ alkyl;

$R^6$ is hydrogen, deuterium or an optionally substituted $C_1$-$C_6$ alkyl;

$X^1$ and $X^2$ are each independently selected from the group consisting of hydrogen, deuterium, an optionally substituted $C_1$-$C_6$ alkyl, an optionally substituted aryl, an optionally substituted heteroaryl, halogen, —CN, —$N_3$, —COOR$^B$, —NR$^A$R$^B$, —OR$^B$, and —SR$^B$, where at least one of $X^1$ and $X^2$ is selected from the group consisting of an optionally substituted aryl, an optionally substituted heteroaryl, halogen, —CN, —$N_3$, —COOR$^B$, —NR$^A$R$^B$, —OR$^B$, and —SR$^B$;

$R^A$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^B$ is selected from the group consisting of hydrogen, deuterium, an optionally substituted $C_1$-$C_6$ alkyl, an optionally substituted $C_3$-$C_7$ cycloalkyl, an optionally substituted aryl, and an optionally substituted heteroaryl;

$R^7$ is an unsubstituted $C_1$-$C_6$ alkyl, an optionally substituted heteroaryl, or —C(=O)R$^C$;

$R^C$ is selected from the group consisting of an unsubstituted $C_1$-$C_6$ alkyl, optionally substituted $C_1$-$C_6$ alkoxy, an optionally substituted $C_3$-$C_7$ cycloalkyl, an optionally substituted aryl, and an optionally substituted heteroaryl, and hydroxyl; and $R^8$ is hydrogen, deuterium or hydroxyl.

2. The compound of claim 1 having the structure of Formula Ia, Ib or Ic:

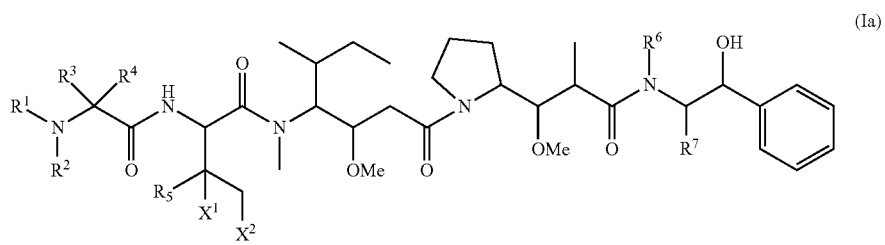

(Ia)

or pharmaceutically acceptable salts or solvates thereof,

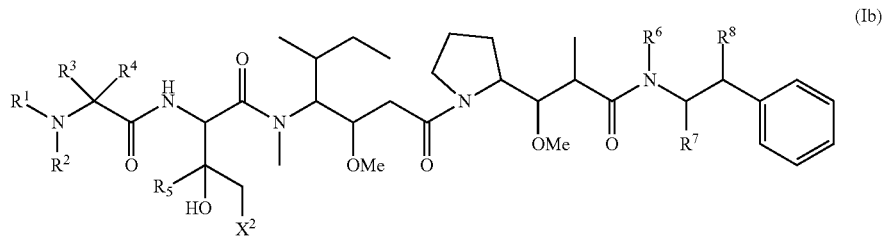

(Ib)

or pharmaceutically acceptable salts or solvates thereof, or

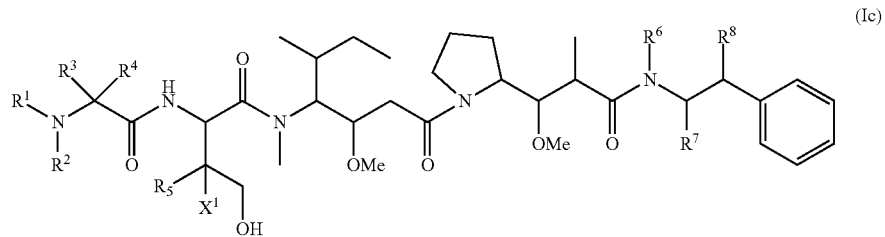

(Ic)

or pharmaceutically acceptable salts or solvates thereof.

3. The compound of claim 1, wherein $R^5$ is an optionally substituted $C_1$-$C_6$ alkyl.

4. The compound of claim 1, wherein $R^3$ is optionally substituted $C_1$-$C_6$ alkyl; and $R^4$ is $C_1$-$C_6$ alkyl.

5. The compound claim 1, wherein $R^7$ is an optionally substituted thiazolyl.

6. A compound having the structure of

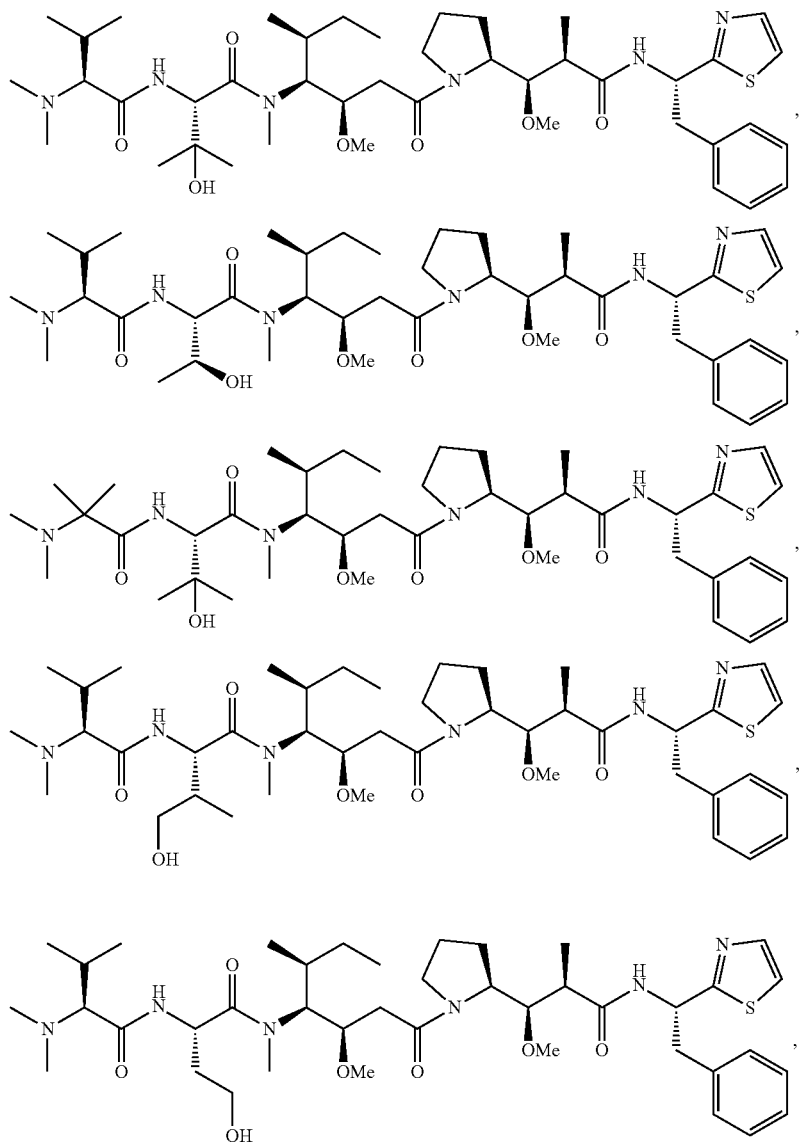

-continued
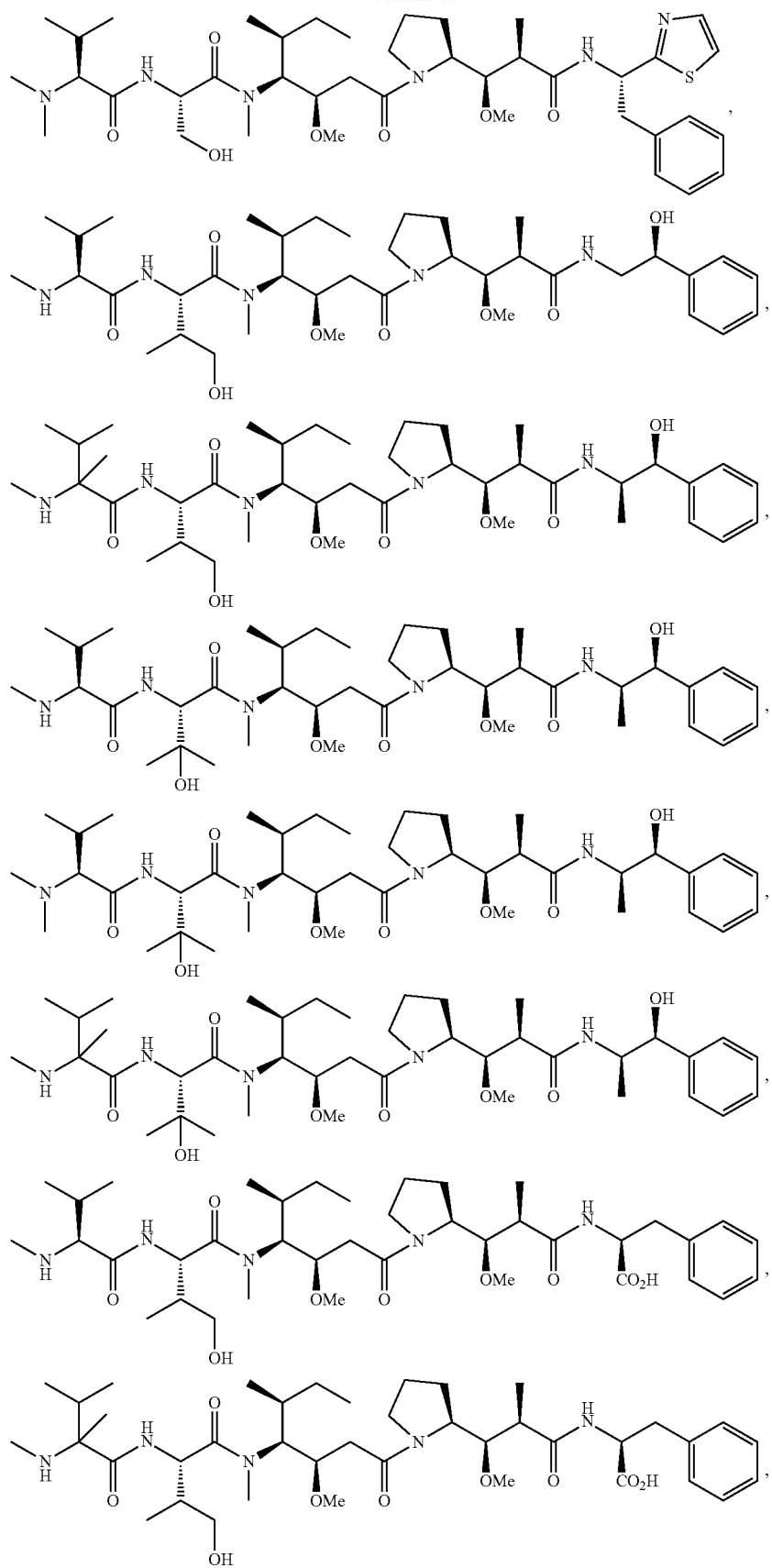

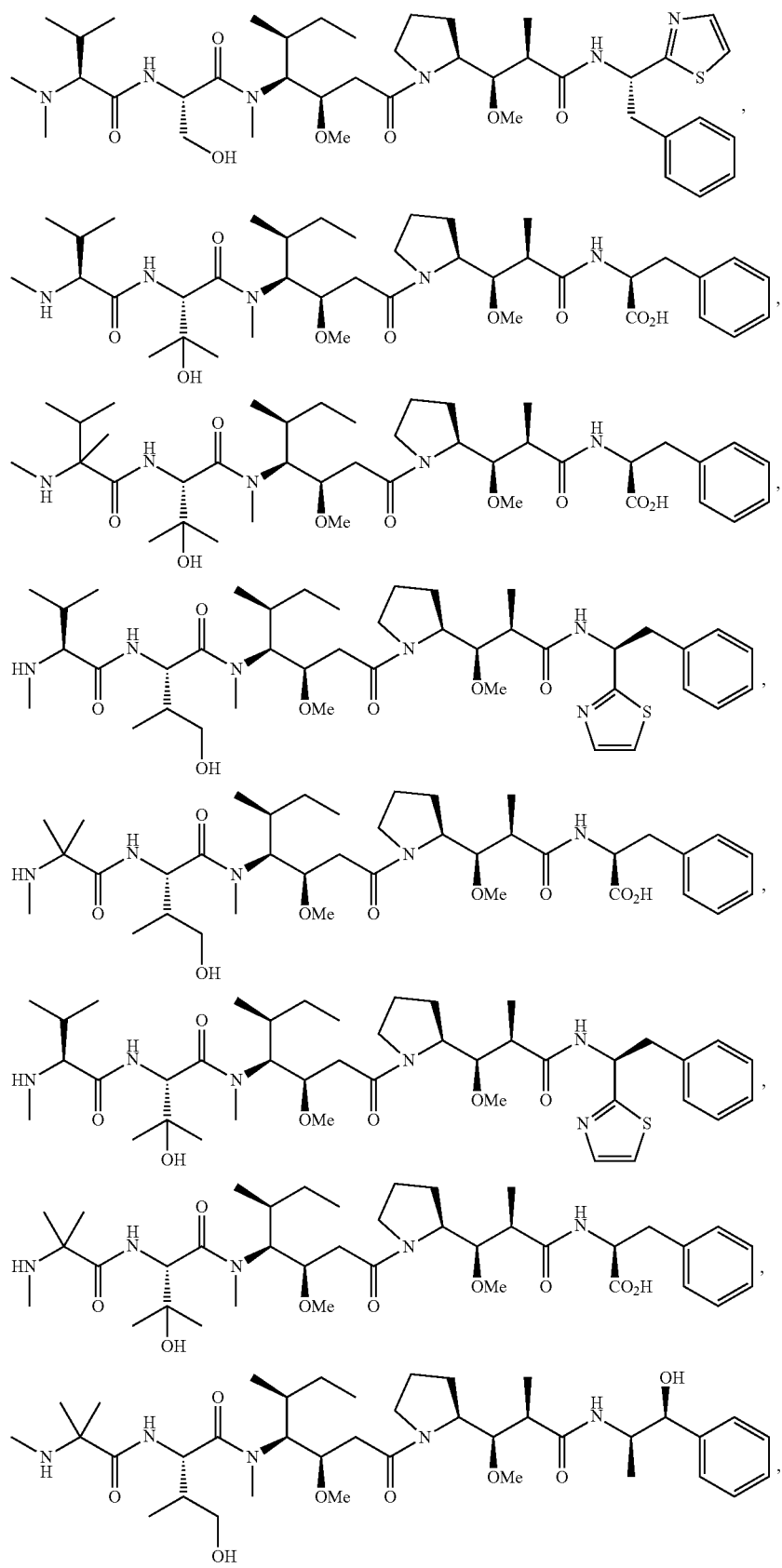

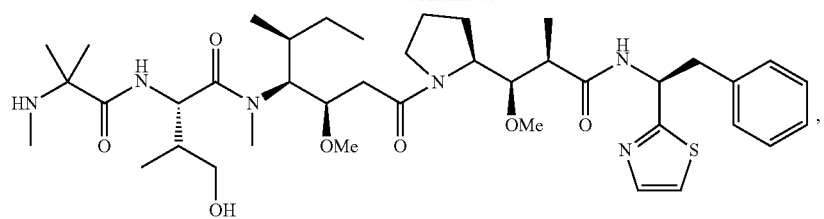
,
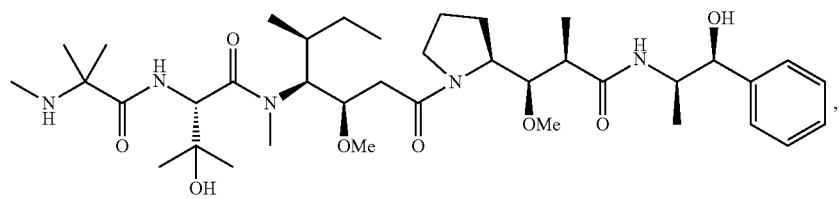
,
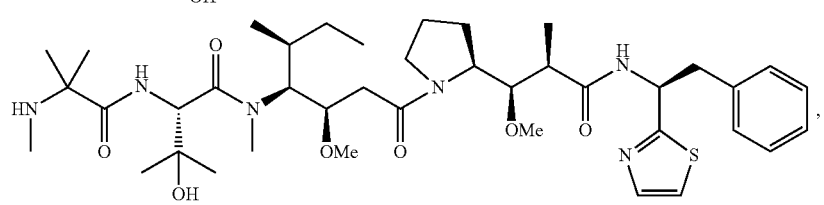
,
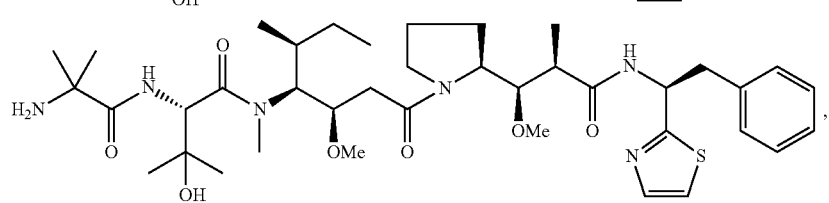
,
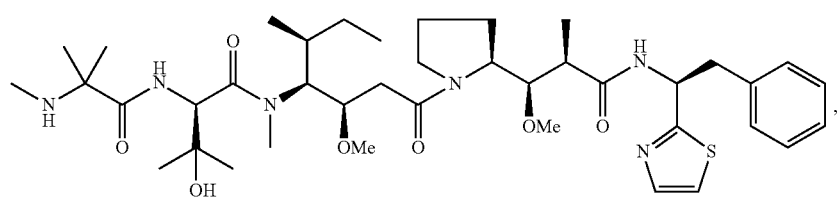
,
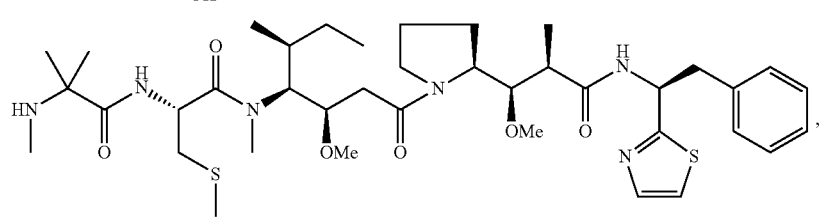
,
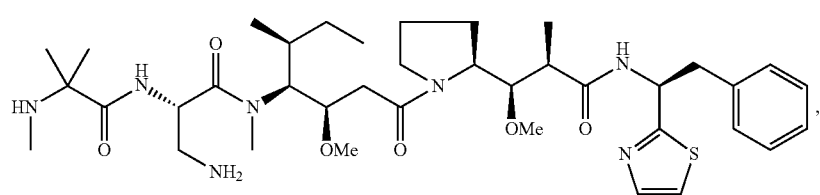
,
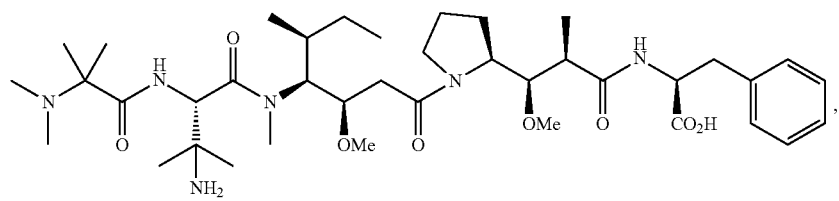
, -continued
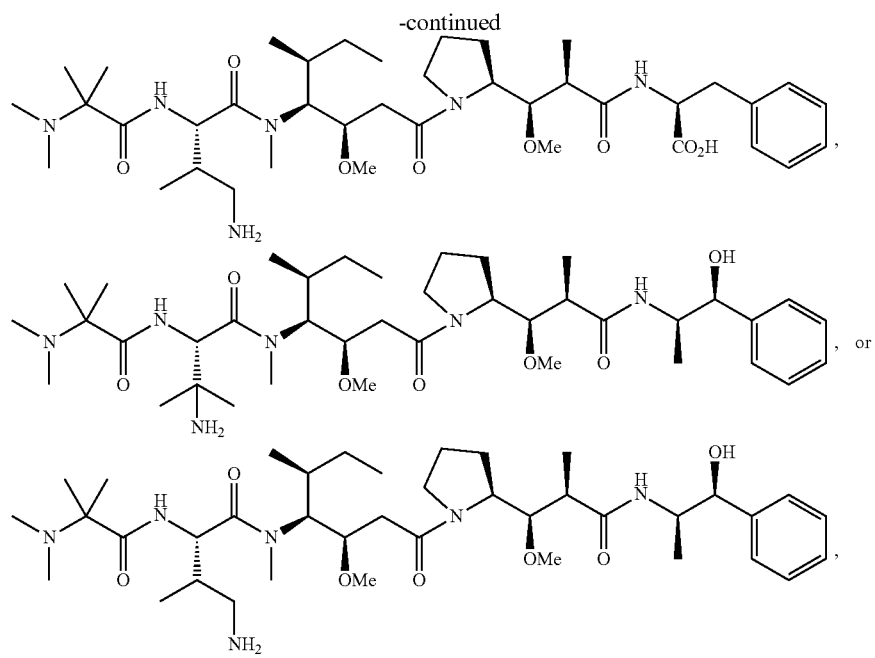
or pharmaceutically acceptable salts or solvates thereof.
7. A compound having the structure of
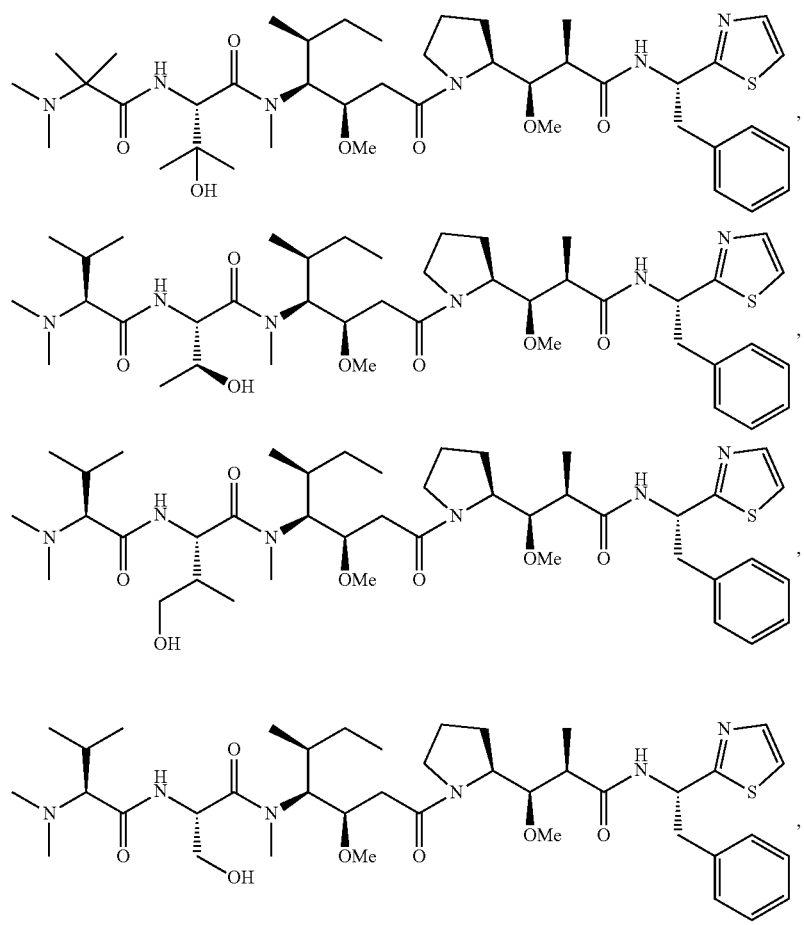

-continued

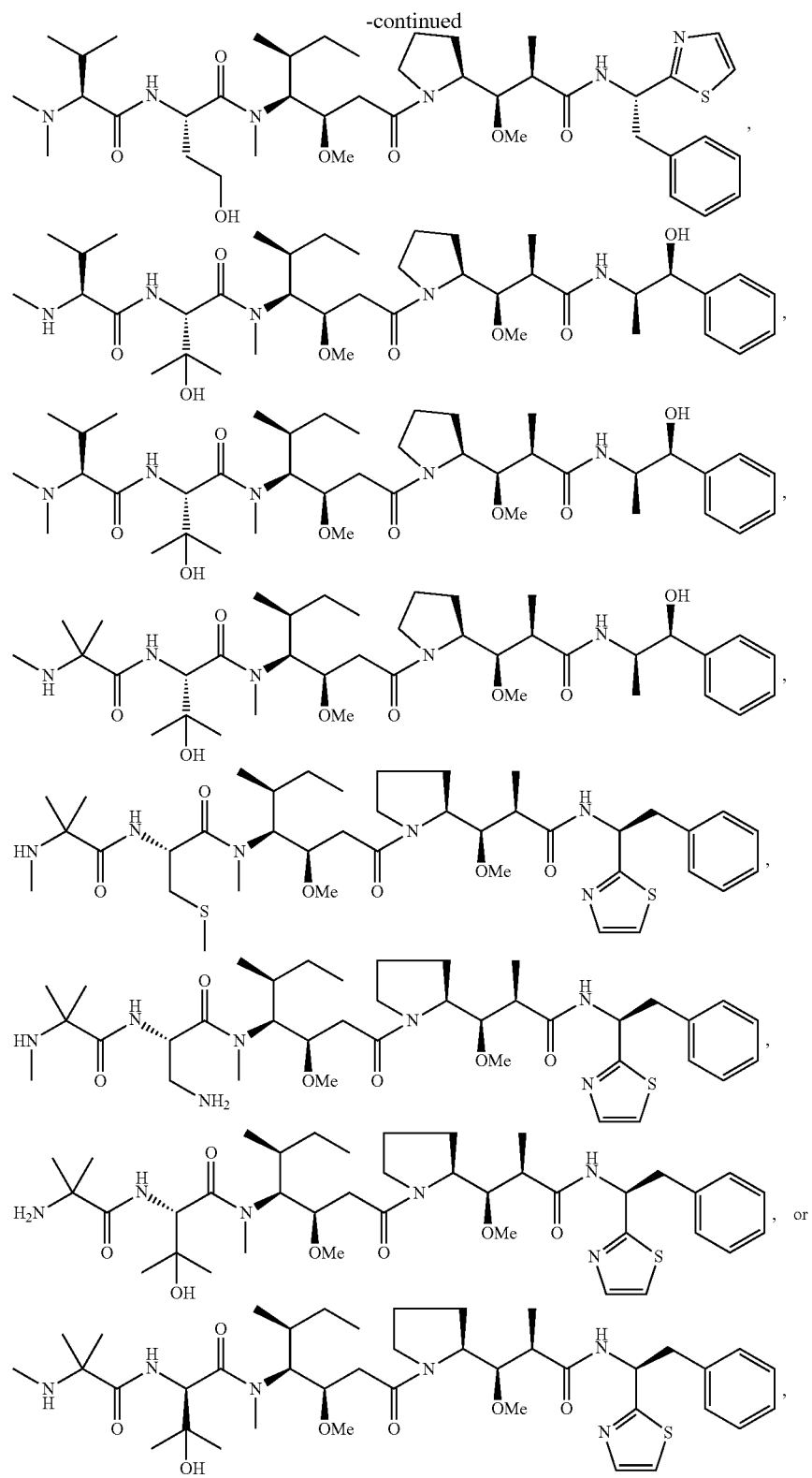

or pharmaceutically acceptable salts or solvates thereof.

8. A method of treating cancer, comprising administering a compound of claim 1 to a subject in need thereof, wherein the cancer is selected from the group consisting of a carcinoma, a sarcoma, a lymphoma, and a blastoma.

9. A method of treating cancer, comprising administering a compound of claim 1 to a subject in need thereof, wherein the cancer is selected from the group consisting of uterine sarcoma cancer, bladder cancer, breast cancer, colon cancer, rectal cancer, endometrial cancer, kidney cancer, lung cancer, melanoma, non-Hodgkin lymphoma, glioblastoma, pancreatic cancer, prostate cancer, and thyroid cancer.

* * * * *